(12) United States Patent
Gerspacher et al.

(10) Patent No.: US 8,030,497 B2
(45) Date of Patent: Oct. 4, 2011

(54) BENZIMIDAZOLE DERIVATIVES

(75) Inventors: Marc Gerspacher, Kappel (CH); Sven Weiler, Lörrach (DE)

(73) Assignee: Novartis AG, Basel (CH)

( * ) Notice: Subject to any disclaimer, the term of this patent is extended or adjusted under 35 U.S.C. 154(b) by 1465 days.

(21) Appl. No.: 10/585,480

(22) PCT Filed: Jan. 13, 2005

(86) PCT No.: PCT/EP2005/000291
§ 371 (c)(1),
(2), (4) Date: Jul. 31, 2006

(87) PCT Pub. No.: WO2005/068433
PCT Pub. Date: Jul. 28, 2005

(65) Prior Publication Data
US 2009/0170921 A1      Jul. 2, 2009

(30) Foreign Application Priority Data
Jan. 14, 2004   (GB) .................................. 0400781.1

(51) Int. Cl.
*C07D 235/00*      (2006.01)
*C07D 235/12*      (2006.01)
*C07D 235/18*      (2006.01)

(52) U.S. Cl. ................. 548/304.4; 548/310.1; 548/310.7

(58) Field of Classification Search ............... 548/304.4, 548/310.1, 310.7
See application file for complete search history.

(56) References Cited

U.S. PATENT DOCUMENTS

| 2,500,487 | A | * | 3/1950 | Craig ........................... 430/388 |
| 3,080,282 | A | * | 3/1963 | Shunk .......................... 514/394 |
| 3,162,574 | A | * | 12/1964 | Forsyth ........................ 514/224.8 |
| 3,294,542 | A | * | 12/1966 | Sus et al. ...................... 430/181 |
| 5,626,875 | A | * | 5/1997 | Ballester Rodes et al. ... 424/464 |
| 6,184,235 | B1 | * | 2/2001 | Connor et al. ................ 514/322 |
| 6,696,437 | B1 | * | 2/2004 | Lubisch et al. .......... 514/217.09 |
| 6,855,714 | B2 | * | 2/2005 | Blume et al. ............. 514/253.01 |
| 2004/0170689 | A1 | * | 9/2004 | Odink et al. .................. 424/471 |

FOREIGN PATENT DOCUMENTS

WO      03/099776 A1    12/2003
WO      03/099814        12/2003

OTHER PUBLICATIONS

Andre Mauricio de Oliveira, et al, QSAR and Molecular Modelling Studies on B-DNA Recognition of Minor Groove Binders, 38 Eur. J. Med. Chem. 141 (2003).*
George Patani & Edmond LaVoie, Bioisosterism: A Rational Approach in Drug Design, 96 Chem. Rev. 3147 (1996).*
Gowen M et al., "Antagonizing the Parathyroid Calcium Receptor Stimulates Parathyroid Hormone Secretion and Bone Formation in Osteopenic Rats", Journal of Clinical Investigation, NY, vol. 105, No. 11, pp. 1595-1604, (2000).

* cited by examiner

*Primary Examiner* — Karlheinz R Skowronek
*Assistant Examiner* — Sean Basquill
(74) *Attorney, Agent, or Firm* — John B. Alexander

(57) ABSTRACT

A compound of formula (I) or a pharmaceutically acceptable salt or prodrug ester thereof:

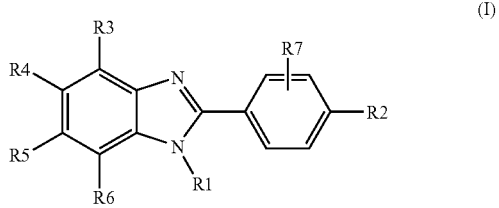

wherein R1-R7 are as disclosed in the specification.

4 Claims, No Drawings

BENZIMIDAZOLE DERIVATIVES

The present invention relates to bicyclic compounds, in particular to benzimidazole derivatives and to pharmaceutical uses thereof.

Accordingly the invention provides compounds of formula (I) or a pharmaceutically acceptable salt or prodrug ester thereof:

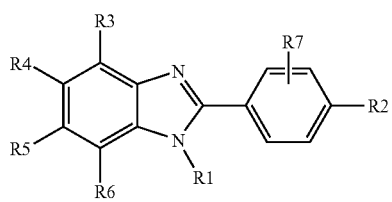

(I)

wherein
R1 is selected from the group consisting of optionally substituted ($C_1$-$C_6$ alkyl, lower alkoxy, lower alkoxy-lower alkyl, cycloalkyloxy-lower alkyl, lower thioalkyl, lower alkylthio-lower alkyl, cycloalkyl, cycloalkyl-lower alkyl, lower alkenyl and lower alkynyl);
R2 is selected from the group consisting of optionally substituted (lower alkyl, cycloalkyl, cycloalkyl-lower alkyl, aryl, heteroaryl, aryl-lower alkyl, heteroaryl-lower alkyl);
R3 is selected from the group consisting of halo, cyano, optionally substituted (lower alkyl, lower alkoxy, lower thioalkyl, lower thioalkenyl, aryl, aryl-lower alkyl, heteroaryl, lower alkenyl, lower alkynyl, heteroaryl, aryl-lower alkyl and heteroaryl-lower alkyl and amino);
R4 is selected from the group consisting of H, halo, cyano, hydroxy, optionally substituted (lower alkyl, lower alkoxy, lower thioalkyl, lower thioalkenyl, aryl, heteroaryl, aryl-lower alkyl, heteroaryl-lower alkyl, alkenyl, alkynyl and amino) and the group having the formula R8-Z-$(CH_2)_n$—;
wherein Z represents a direct bond or is selected from the group consisting of O, NH, $CH_2$, CO, SO, $SO_2$ or S;
wherein R8 is selected from the group consisting of optionally substituted (aryl, heteroaryl, carbocyclic aryl, cycloalkyl, heterocycloalkyl);
and wherein n is 0, 1, 2 or 3;
R5 is selected from the group consisting of H, halo, cyano, hydroxyl, optionally substituted (lower alkyl, lower alkoxy, lower alkoxy-lower alkyl, aryl, heteroaryl, aryl-lower alkyl, heteroaryl-lower alkyl, alkenyl, alkynyl and amino);
R6 is selected from the group consisting of halo, cyano, optionally substituted (lower alkyl, lower alkoxy, lower thioalkyl, lower alkenyl, lower alkynyl, lower alkoxy-lower alkyl, aryl, heteroaryl, aryl-lower alkyl, heteroaryl-lower alkyl and amino).
R7 represents one or more substituents independently selected from the group consisting of H, halo, hydroxyl, optionally substituted (lower alkyl, lower alkoxy, amino, cyano, and carbonyl).

The optional substituent or substituents on R1-R8 are independently selected from the group consisting of halogen, hydroxy, lower alkyl, mono or di-lower alkylamino, aminocarbonyl, sulfinyl, sulfonyl, sulfanyl, mono or di-lower alkylaminocarbonyl, amino, carboxy, lower alkoxy; $C_3$-$C_{12}$ cycloalkyl, $C_3$-$C_{18}$ heterocycloalkyl, lower alkylcarbonyl, lower alkoxycarbonyl, nitryl, aryl; all of which, except halogen, are independently optionally substituted by one or more substituents, selected from the group consisting of halogen, hydroxy, lower alkyl, mono or di-lower alkylamino, aminocarbonyl, sulfinyl, sulfonyl, sulfanyl, mono or di-lower alkylaminocarbonyl, amino, carboxy, lower alkoxy, $C_3$-$C_{12}$ cycloalkyl, $C_3$-$C_{18}$-heterocycloalkyl, lower alkylcarbonyl, lower alkoxycarbonyl, nitryl, aryl.

For the avoidance of doubt, the terms listed below are to be understood to have the following meaning throughout the present description and claims:

The term "lower", when referring to organic radicals or compounds means a compound or radical with may be branched or unbranched with up to and including 7 carbon atoms.

A lower alkyl group may be branched, unbranched or cyclic and contains 1 to 7 carbon atoms, preferably 1 to 4 carbon atoms. Lower alkyl represents, for example: methyl, ethyl, propyl, butyl, isopropyl, isobutyl, tertiary butyl or 2,2-dimethylpropyl.

A lower alkoxy group may be branched or unbranched and contains 1 to 7 carbon atoms, preferably 1 to 6 carbon atoms. Lower alkoxy represents, for example: methoxy, ethoxy, propoxy, butoxy, isopropoxy, isobutoxy or tertiary butoxy. Lower alkoxy includes cycloalkyloxy and cycloalkyl-lower alkyloxy.

A lower alkene, alkenyl or alkenoxy group is branched or unbranched and contains 2 to 7 carbon atoms, preferably 1 to 4 carbon atoms and contains at least one carbon-carbon double bond. Lower alkene, lower alkenyl or lower alkenyloxy represents for example vinyl, prop-1-enyl, allyl, butenyl, isopropenyl or isobutenyl and the oxy equivalents thereof.

A lower alkyne or alkynyl group is branched or unbranched and contains 2 to 7 carbon atoms, preferably 1 to 4 carbon atoms and contains at least one carbon-carbon triple bond. Lower alkyne or lower alkynyl or lower alkenyloxy represents for example ethynyl or propynyl.

In the present application, oxygen containing substituents, e.g. alkoxy, alkenyloxy, alkynyloxy, carbonyl, etc. encompass their sulphur containing homologues, e.g. thioalkyl, alkyl-thioalkyl, thioalkenyl, alkenyl-thioalkyl, thioalkynyl, thiocarbonyl, sulphone, sulphoxide etc.

Halo or halogen represents chloro, fluoro, bromo or iodo.
Aryl represents carbocyclic aryl, heterocyclic aryl or biaryl.

Carbocyclic aryl is an aromatic cyclic hydrocarbon containing from 6 to 18 ring atoms. It can be monocyclic, bicyclic or tricyclic, for example naphthyl, phenyl, or phenyl mono-, di- or trisubstituted by one, two or three substituents.

Heterocyclic aryl is an aromatic monocyclic or bicyclic hydrocarbon containing from 5 to 18 ring atoms one or more of which are heteroatoms selected from O, N or S. Preferably there are one or two heteroatoms. Heterocyclic aryl represents, for example: pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, oxadiazolyl, benzimidazolyl. Heterocyclic aryl also includes such substituted radicals.

Cycloalkyl represents a cyclic hydrocarbon containing from 3 to 12 ring atoms preferably from 3 to 6 ring atoms. Cycloalkyl represents, for example: cyclopropyl, cyclobutyl, cyclopentyl, or cyclohexyl. The cycloalkyl may optionally be substituted.

Heterocycloalkyl represents a mono-, di- or tricyclic hydrocarbon which may be saturated or unsaturated and which contains one or more, preferably one to three heteroatoms selected from O, N or S. Preferably it contains between three and 18 ring atoms. The term heterocycloalkyl is intended also to include bridged heterocycloalkyl groups such as 3-hyroxy-8-aza-bicyclo[3.2.1]oct-8-yl.

Pharmaceutically acceptable salts include acid addition salts with conventional acids, for example mineral acids, e.g. hydrochloric acid, sulfuric or phosphoric acid, or organic acids, for example aliphatic or aromatic carboxylic or sulfonic acids, e.g. acetic, trifluoroacetic, propionic, succinic, glycolic, lactic, malic, tartaric, citric, ascorbic, maleic, fumaric, hydroxylmaleic, pyruvic, pamoic, methanesulfonic, toluenesulfonic, naphthalenesulfonic, sulfanilic or cyclohexylsulfamic acid; also amino acids, such as arginine and lysine. For compounds of the invention having acidic groups, for example a free carboxy group, pharmaceutically acceptable salts also represent metal or ammonium salts, such as alkali metal or alkaline earth metal salts, e.g. sodium, potassium, magnesium or calcium salts, as well as ammonium salts, which are formed with ammonia or suitable organic amines.

The agents of the invention which comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding agents of the invention which comprise free hydroxyl groups. Suitable pharmaceutically acceptable prodrug esters are those derived from a carboxylic acid, a carbonic acid monoester or a carbamic acid, advantageously esters derived from an optionally substituted lower alkanoic acid or an arylcarboxylic acid.

A second aspect of the invention provides a compound of formula (I') or a pharmaceutically acceptable salt, or prodrug ester thereof:

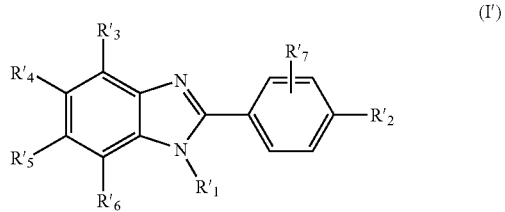

(I')

wherein $R'_1$ is selected from the group consisting of optionally substituted ($C_1$-$C_6$ alkyl, lower alkoxy-lower alkyl, lower alkynyl, lower thioalkyl-lower alkyl, cycloalkyl-lower alkyl);

$R'_2$ is lower alkyl;

$R'_3$ is selected from the group consisting of halo, cyano, optionally substituted (lower alkyl, lower alkoxy, lower thioalkyl, lower thioalkenyl, lower alkynyl, aryl and aryl-lower alkyl);

$R'_4$ is selected from the group consisting of H, halo, cyano, optionally substituted (lower alkyl, aryl, aryl-lower alkyl, heteroaryl, heteroaryl-lower alkyl) and the group having the formula $R'_8$-Z(CH$_2$)$_n$—;

wherein Z represents a direct bond or is selected from the group consisting of O, NH, CH$_2$, CO, SO, SO$_2$ or S;

wherein $R'_8$ is selected from the group consisting of optionally substituted (aryl, pyrazolyl, thiazolyl, cyclobutyl, tetrazolyl, pyridyl, indazolyl, pyrazinyl, furanyl, isoxazolyl, pyrrolidinyl, benzimidazolyl, imidazolyl, oxazolyl);

and wherein n is 0, 1, 2 or 3;

$R'_5$ is H, halo, or lower alkyl;

$R'_6$ is selected from the group consisting of halo, optionally substituted (lower alkyl, lower alkoxy, lower alkenyl, lower alkynyl);

$R'_7$ represents one or more substituents independently selected from the group consisting of H, halo, hydroxyl, optionally substituted (lower alkyl, lower alkoxy, amino, cyano, and carbonyl);

the optional substituent or substituents on $R'_1$-$R'_8$ being independently selected from the group consisting of halogen, hydroxy, lower alkyl, mono or di-lower alkylamino, aminocarbonyl, sulfinyl, sulfonyl, sulfanyl, mono or di-lower alkylaminocarbonyl, amino, carboxy, lower alkoxy, $C_3$-$C_{12}$ cycloalkyl, $C_3$-$C_{18}$ heterocycloalkyl, lower alkylcarbonyl, lower alkoxycarbonyl, nitryl, aryl; all of which, except halogen, are independently optionally substituted by one or more substituents, selected from the group consisting of halogen, hydroxy, lower alkyl, mono or di-lower alkylamino, aminocarbonyl, sulfinyl, sulfonyl, sulfanyl, mono or di-lower alkylaminocarbonyl, amino, carboxy, lower alkoxy, $C_3$-$C_{12}$ cycloalkyl, $C_3$-$C_{18}$ heterocycloalkyl, lower alkylcarbonyl, lower alkoxycarbonyl, nitryl, aryl.

With reference to formula I and I', preferably R3 or $R'_3$ is halo, ethyl or substituted methyl. For example, R3 or $R'_3$ may be Br, I or CF$_3$. More preferably, R3 or $R'_3$ is Br. Alternatively preferably, R3 or $R'_3$ is trifluoromethyl. Alternatively preferably, R3 or $R'_3$ is ethynyl.

R7 or $R'_7$ is preferably located at the 2 and/or 2' position of the phenyl ring.

Preferred compounds of formula I are:

4-Bromo-2-(4-isopropyl-phenyl)-7-methoxy-1-(2-methoxy-ethyl)-1H-benzoimidazole

4-Iodo-2-(4-isopropyl-phenyl)-7-methoxy-1-(2-methoxy-ethyl)-1H-benzoimidazole

4-Iodo-2-(4-isopropyl-phenyl)-7-methoxy-1-(2-methylsulfanyl-ethyl)-1H-benzoimidazole 4-Bromo-2-(4-isopropyl-phenyl)-7-methoxy-1-(2-methylsulfanyl-ethyl)-1H-benzoimidazole 4-Bromo-1-cyclopropylmethyl-2-(4-isopropyl-phenyl)-7-methoxy-1H-benzoimidazole 4-Bromo-1-propyl-2-(4-isopropyl-phenyl)-7-methoxy-1H-benzoimidazole 4-Bromo-1-butyl-2-(4-isopropyl-phenyl)-7-methoxy-1H-benzoimidazole 4-Bromo-1-ethyl-2-(4-isopropyl-phenyl)-7-methoxy-1H-benzoimidazole {2-[4-Bromo-2-(4-isopropyl-phenyl)-7-methoxy-benzoimidazol-1-yl]-ethyl}-dimethyl-amine 4-Chloro-2-(4-isopropyl-phenyl)-7-methoxy-1-(2-methoxy-ethyl)-1H-benzoimidazole 4-Ethynyl-2-(4-isopropyl-phenyl)-7-methoxy-1-(2-methoxy-ethyl)-1H-benzoimidazole 2-(4-Isopropyl-phenyl)-7-methoxy-1-(2-methoxy-ethyl)-4-phenyl-1H-benzoimidazole 3-[2-(4-Isopropyl-phenyl)-7-methoxy-1-(2-methoxy-ethyl)-1H-benzoimidazol-4-yl]-phenol 2-(4-Isopropyl-phenyl)-7-methoxy-4-[3-(2-methoxy-ethoxy)-phenyl]-1-(2-methoxy-ethyl)-1H-benzoimidazole 4-(3,5-Dimethoxy-phenyl)-2-(4-isopropyl-phenyl)-7-methoxy-1-(2-methoxy-ethyl)-1H-benzoimidazole 4-Methyl-2-(4-isopropyl-phenyl)-7-methoxy-1-(2-methoxy-ethyl)-1H-benzoimidazole 4-Ethyl-2-(4-isopropyl-phenyl)-7-methoxy-1-(2-methoxy-ethyl)-1H-benzoimidazole 4-Ethylsulfanyl-2-(4-isopropyl-phenyl)-7-methoxy-1-(2-methoxy-ethyl)-1H-benzoimidazole
4-Bromo-2-(4-cyclopropyl-phenyl)-7-methoxy-1-(2-methoxy-ethyl)-1H-benzoimidazole
4-Bromo-2-(4-cyclopropyl-phenyl)-7-methoxy-1-(2-methylsulfanyl-ethyl)-1H-benzoimidazole
4-Bromo-1-cyclopropylmethyl-2-(4-cyclopropyl-phenyl)-7-methoxy-1H-benzoimidazole
5-Bromo-2-(4-isopropyl-phenyl)-7-methoxy-1-(2-methoxy-ethyl)-1H-benzoimidazole
4,5-Dibromo-2-(4-isopropyl-phenyl)-7-methoxy-1-(2-methoxy-ethyl)-1H-benzoimidazole
4,5-Dibromo-2-(4-cyclopropyl-phenyl)-7-methoxy-1-(2-methoxy-ethyl)-1H-benzoimidazole
4,5-Dibromo-2-(4-isopropyl-2-methoxy-phenyl)-7-methoxy-(2-methoxy-ethyl)-1H-benzoimidazole
4-Iodo-5-bromo-2-(4-isopropyl-phenyl)-7-methoxy-1-(2-methoxy-ethyl)-1H-benzoimidazole
5-Bromo-4-iodo-2-(4-isopropyl-2-methoxy-phenyl)-7-methoxy-1-(2-methoxy-ethyl)-1H-benzoimidazole
4-Bromo-2-(4-isopropyl-phenyl)-7-methoxy-1-(2-methoxy-ethyl)-5-trifluoromethyl-1H-benzoimidazole
4-Bromo-1-cyclopropylmethyl-2-(4-isopropyl-phenyl)-7-methoxy-5-trifluoromethyl-1H-benzoimidazole
4-Bromo-5-iodo-2-(4-isopropyl-phenyl)-7-methoxy-1-(2-methoxy-ethyl)-1H-benzoimidazole
5-Bromo-4-ethynyl-2-(4-isopropyl-phenyl)-7-methoxy-1-(2-methoxy-ethyl)-1H-benzoimidazole
2-(4-Isopropyl-phenyl)-7-methoxy-1-(2-methoxy-ethyl)-1H-benzoimidazole-5-carbonitrile
4-Bromo-2-(4-isopropyl-phenyl)-7-methoxy-1-(2-methoxy-ethyl)-1H-benzoimidazole-5-carbonitrile
4-Bromo-5-fluoro-2-(4-isopropyl-phenyl)-7-methoxy-1-(2-methoxy-ethyl)-1H-benzoimidazole
5-Benzyl-4-bromo-2-(4-isopropyl-phenyl)-7-methoxy-1-(2-methoxy-ethyl)-1H-benzoimidazole
5-Benzyl-4-iodo-2-(4-isopropyl-phenyl)-7-methoxy-1-(2-methoxy-ethyl)-1H-benzoimidazole
5-Benzyl-4-ethynyl-2-(4-isopropyl-phenyl)-7-methoxy-1-(2-methoxy-ethyl)-1H-benzoimidazole
4-Ethynyl-2-(4-isopropyl-phenyl)-7-methoxy-5-(2-methoxy-benzyl)-1-(2-methoxy-ethyl)-1H-benzoimidazole
4-Bromo-5-ethyl-2-(4-isopropyl-phenyl)-7-methoxy-1-(2-methoxy-ethyl)-1H-benzoimidazole
4-Bromo-5-cyclobutylmethyl-2-(4-isopropyl-phenyl)-7-methoxy-1-(2-methoxy-ethyl)-1H-benzoimidazole
4-Bromo-5-(3-fluoro-benzyl)-2-(4-isopropyl-phenyl)-7-methoxy-1-(2-methoxy-ethyl)-1H-benzoimidazole
4-Bromo-5-(3-chloro-benzyl)-2-(4-isopropyl-phenyl)-7-methoxy-1-(2-methoxy-ethyl)-1H-benzoimidazole
4-Bromo-2-(4-isopropyl-phenyl)-7-methoxy-1-(2-methoxy-ethyl)-5-thiazol-2-ylmethyl-1H-benzoimidazole
4-Bromo-5-(3,5-difluoro-benzyl)-2-(4-isopropyl-phenyl)-7-methoxy-1-(2-methoxy-ethyl)-1H-benzoimidazole
4-Bromo-2-(4-isopropyl-phenyl)-7-methoxy-1-(2-methoxy-ethyl)-5-pyridin-3-ylmethyl-1H-benzoimidazole
4-Bromo-2-(4-isopropyl-phenyl)-7-methoxy-1-(2-methoxy-ethyl)-5-(2-methylsulfanyl-benzyl)-1H-benzoimidazole
4-Bromo-2-(4-isopropyl-phenyl)-5-(2-methanesulfinyl-benzyl)-7-methoxy-1-(2-methoxy-ethyl)-1H-benzoimidazole
4-Bromo-2-(4-isopropyl-phenyl)-5-(2-methanesulfonyl-benzyl)-7-methoxy-1-(2-methoxy-ethyl)-1H-benzoimidazole
4-Bromo-2-(4-isopropyl-phenyl)-7-methoxy-1-(2-methoxy-ethyl)-5-pyridin-2-ylmethyl-1H-benzoimidazole
4-Iodo-2-(4-isopropyl-phenyl)-7-methoxy-5-(2-methoxy-benzyl)-1-(2-methoxy-ethyl)-1H-benzoimidazole
4-Bromo-2-(4-isopropyl-phenyl)-7-methoxy-5-(2-methoxy-benzyl)-1-(2-methoxy-ethyl)-1H-benzoimidazole
4-Bromo-5-(3,4-dimethoxy-benzyl)-2-(4-isopropyl-phenyl)-7-methoxy-1-(2-methoxy-ethyl)-1H-benzoimidazole
4-Bromo-2-(4-isopropyl-phenyl)-7-methoxy-1-(2-methoxy-ethyl)-5-(3-methoxy-pyridin-2-ylmethyl)-1H-benzoimidazole
5-Benzyl-4-ethyl-2-(4-isopropyl-phenyl)-7-methoxy-1-(2-methoxy-ethyl)-1H-benzoimidazole
4-Bromo-2-(4-isopropyl-phenyl)-7-methoxy-5-(3-methoxy-benzyl)-1-(2-methoxy-ethyl)-1H-benzoimidazole
[4-Bromo-2-(4-isopropyl-phenyl)-7-methoxy-1-(2-methoxy-ethyl)-1H-benzoimidazol-5-yl]-(3-methoxy-phenyl)-methanone
[4-Bromo-2-(4-isopropyl-phenyl)-7-methoxy-1-(2-methoxy-ethyl)-1H-benzoimidazol-5-yl]-(2-methoxy-phenyl)-methanone
4-Bromo-2-(4-isopropyl-phenyl)-7-methoxy-1-(2-methoxy-ethyl)-5-(1-phenyl-ethyl)-1H-benzoimidazole
4-Iodo-2-(4-isopropyl-phenyl)-7-methoxy-1-(2-methoxy-ethyl)-1H-benzoimidazole-5-carbonitrile
2-(4-Isopropyl-phenyl)-7-methoxy-1-(2-methoxy-ethyl)-1H-benzoimidazole-4-carbonitrile
4-Isobutyl-2-(4-isopropyl-phenyl)-7-methoxy-1-(2-methoxy-ethyl)-1H-benzoimidazole
4-Benzyl-2-(4-isopropyl-phenyl)-7-methoxy-1-(2-methoxy-ethyl)-1H-benzoimidazole
4,7-Dibromo-2-(4-isopropyl-phenyl)-1-(2-methoxy-ethyl)-1H-benzoimidazole
4,7-Dibromo-2-(4-isopropyl-phenyl)-1-(2-methoxy-ethyl)-1H-benzoimidazole
4-Bromo-2-(4-isopropyl-phenyl)-7-methoxy-1-(2-methoxy-ethyl)-5-phenyl-1H-benzoimidazole
4-Bromo-5-(3,4-dimethoxy-phenyl)-2-(4-isopropyl-phenyl)-7-methoxy-1-(2-methoxy-ethyl)-1H-benzoimidazole
3-[4-Bromo-2-(4-isopropyl-phenyl)-7-methoxy-1-(2-methoxy-ethyl)-1H-benzoimidazol-5-yl]-phenol
4-Bromo-2-(4-isopropyl-phenyl)-7-methoxy-1-(2-methoxy-ethyl)-5-(3-methoxy-phenyl)-1H-benzoimidazole
3-[4-Bromo-2-(4-isopropyl-phenyl)-7-methoxy-1-(2-methoxy-ethyl)-1H-benzoimidazol-5-yl]-benzoic acid ethyl ester
4-[4-Bromo-2-(4-isopropyl-phenyl)-7-methoxy-1-(2-methoxy-ethyl)-1H-benzoimidazol-5-yl]-benzoic acid ethyl ester
4-Bromo-2-(4-isopropyl-phenyl)-7-methoxy-1-(2-methoxy-ethyl)-5-pyridin-3-yl-1H-benzoimidazole
3-[4-Bromo-2-(4-isopropyl-phenyl)-7-methoxy-1-(2-methoxy-ethyl)-1H-benzoimidazol-5-yl]-benzonitrile
1-{5-[4-Bromo-2-(4-isopropyl-phenyl)-7-methoxy-1-(2-methoxy-ethyl)-1H-benzoimidazol-5-yl]-2-methoxy-phenyl}-ethanone
2-[4-Bromo-2-(4-isopropyl-phenyl)-7-methoxy-1-(2-methoxy-ethyl)-1H-benzoimidazol-5-yl]-benzonitrile
2-(4-Isopropyl-phenyl)-7-methoxy-1-(2-methoxy-ethyl)-5-(3-methoxy-phenyl)-1H-benzoimidazole
4-Iodo-2-(4-isopropyl-phenyl)-7-methoxy-1-(2-methoxy-ethyl)-5-pyridin-4-yl-1H-benzoimidazole
4-Bromo-2-(4-isopropyl-phenyl)-7-methoxy-1-(2-methoxy-ethyl)-5-(4-methyl-pyrazol-1-ylmethyl)-1H-benzoimidazol
4-Bromo-5-imidazol-1-ylmethyl-2-(4-isopropyl-phenyl)-7-methoxy-1-(2-methoxy-ethyl)-1H-benzoimidazole
4-Bromo-5-(4-bromo-5-methyl-pyrazol-1-ylmethyl)-2-(4-isopropyl-phenyl)-7-methoxy-1-(2-methoxy-ethyl)-1H-benzoimidazole 4-Bromo-5-(4-bromo-3-methyl-pyrazol-1-ylmethyl)-2-(4-isopropyl-phenyl)-7-methoxy-1-(2-methoxy-ethyl)-1H-benzoimidazole 4-Bromo-5-(3,5-dimethyl-pyrazol-1-ylmethyl)-2-(4-isopropyl-phenyl)-7-methoxy-1-(2-methoxy-ethyl)-1H-benzoimidazole 1-[4-Bromo-1-(2-hydroxy-ethyl)-2-(4-isopropyl-phenyl)-7-methoxy-1H-benzoimidazol-5-ylmethyl]-1H-imidazole-2-carboxylic acid ethyl ester 4-Bromo-2-(4-isopropyl-phenyl)-7-methoxy-1-(2-methoxy-ethyl)-5-(2-methoxymethyl-imidazol-1-ylmethyl)-1H-benzoimidazole 4-Bromo-2-(4-isopropyl-phenyl)-7-methoxy-1-(2-methoxy-ethyl)-5-(2-methylsulfanyl-imidazol-1-ylmethyl)-1H-benzoimidazole 1-[4-Bromo-2-(4-isopropyl-phenyl)-7-methoxy-1-(2-methoxy-ethyl)-1H-benzoimidazol-5-ylmethyl]-1H-benzoimidazol-2-ol 4-Bromo-2-(4-isopropyl-phenyl)-7-methoxy-1-(2-methoxy-ethyl)-5-(2-methylsulfanyl-benzoimidazol-1-ylmethyl)-1H-benzoimidazole 4-Bromo-2-(4-isopropyl-phenyl)-5-(2-methanesulfinyl-benzoimidazol-1-ylmethyl)-7-methoxy-1-(2-methoxy-ethyl)-1H-benzoimidazole 4-Bromo-2-(4-isopropyl-phenyl)-7-methoxy-5-(2-methoxy-benzoimidazol-1-ylmethyl)-1-(2-methoxy-ethyl)-1H-benzoimidazole 3-[4-Bromo-1-(2-hydroxy-ethyl)-2-(4-isopropyl-phenyl)-7-methoxy-1H-benzoimidazol-5-ylmethyl]-3H-imidazole-4-carboxylic acid methyl ester 2-[4-Bromo-5-imidazo[4,5-b]pyridin-3-ylmethyl-2-(4-isopropyl-phenyl)-7-methoxy-benzoimidazol-1-yl]-ethanol 2-[4-Bromo-5-indazol-1-ylmethyl-2-(4-isopropyl-phenyl)-7-methoxy-benzoimidazol-1-yl]-ethanol 2-[4-Bromo-2-(4-isopropyl-phenyl)-7-methoxy-5-(5-methyl-tetrazol-2-ylmethyl)-benzoimidazol-1-yl]-ethanol 4-Bromo-5-(4-bromo-5-methyl-pyrazol-1-ylmethyl)-2-(4-cyclopropyl-phenyl)-7-methoxy-1-(2-methoxy-ethyl)-1H-benzoimidazole 4-Bromo-2-(4-isopropyl-phenyl)-7-methoxy-5-(4-methyl-pyrazol-1-ylmethyl)-1-(2-methylsulfanyl-ethyl)-1H-benzoimidazole 4-Bromo-5-isopropoxymethyl-2-(4-isopropyl-phenyl)-7-methoxy-1-(2-methoxy-ethyl)-1H-benzoimidazole 1-[4-Bromo-2-(4-isopropyl-phenyl)-7-methoxy-1-(2-methoxy-ethyl)-1H-benzoimidazol-5-ylmethyl]-pyrrolidin-2-one 4-Bromo-2-(4-isopropyl-phenyl)-7-methoxy-1-(2-methoxy-ethyl)-5-phenylsulfanyl-1H-benzoimidazole 5-Benzenesulfinyl-4-bromo-2-(4-isopropyl-phenyl)-7-methoxy-1-(2-methoxy-ethyl)-1H-benzoimidazole 5-Benzyl-2-(4-isopropyl-phenyl)-7-methoxy-1-(2-methoxy-ethyl)-4-trifluoromethyl-1H-benzoimidazole 2-(4-Isopropyl-phenyl)-7-methoxy-5-(2-methoxy-benzyl)-1-(2-methoxy-ethyl)-4-trifluoromethyl-1H-benzoimidazole 2-(4-Isopropyl-phenyl)-7-methoxy-1-(2-methoxy-ethyl)-5-pyridin-2-ylmethyl-4-trifluoromethyl-1H-benzoimidazole 2-(4-Isopropyl-phenyl)-7-methoxy-1-(2-methoxy-ethyl)-5-pyrazol-1-ylmethyl-4-trifluoromethyl-1H-benzoimidazole 4-Bromo-2-(4-isopropyl-phenyl)-7-methoxy-1-(2-methoxy-ethyl)-5-phenoxy methyl-1H-benzoimidazole 2-{2-[4-Bromo-2-(4-isopropyl-phenyl)-7-methoxy-1-(2-methoxy-ethyl)-1H-benzoimidazol-5-ylmethoxy]-phenyl}-ethanol 2-{2-[4-Bromo-2-(4-isopropyl-phenyl)-7-methoxy-1-(2-methoxy-ethyl)-1H-benzoimidazol-5-ylmethoxy]-phenoxy}-ethanol {2-[4-Bromo-2-(4-isopropyl-phenyl)-7-methoxy-1-(2-methoxy-ethyl)-1H-benzoimidazol-5-ylmethoxy]-phenyl}-methanol N-{2-[4-Bromo-2-(4-isopropyl-phenyl)-7-methoxy-1-(2-methoxy-ethyl)-1H-benzoimidazol-5-ylmethoxy]-phenyl}-acetamide 2-[4-Bromo-2-(4-isopropyl-phenyl)-7-methoxy-1-(2-methoxy-ethyl)-1H-benzoimidazol-5-ylmethoxy]-benzamide 2-[4-Bromo-2-(4-isopropyl-phenyl)-7-methoxy-1-(2-methoxy-ethyl)-1H-benzoimidazol-5-ylmethoxy]-benzenesulfonamide 2-[4-Bromo-2-(4-isopropyl-phenyl)-7-methoxy-1-(2-methoxy-ethyl)-1H-benzoimidazol-5-ylmethoxy]-phenylamine 1-{2-[4-Bromo-2-(4-isopropyl-phenyl)-7-methoxy-1-(2-methoxy-ethyl)-1H-benzoimidazol-5-ylmethoxy]-phenyl}-ethanone 2-[4-Bromo-2-(4-isopropyl-phenyl)-7-methoxy-1-(2-methoxy-ethyl)-1H-benzoimidazol-5-ylmethoxy]-phenol 2-[4-Bromo-2-(4-isopropyl-phenyl)-7-methoxy-1-(2-methoxy-ethyl)-1H-benzoimidazol-5-ylmethoxy]-pyridin-3-ol 4-Bromo-2-(4-isopropyl-phenyl)-7-methoxy-1-(2-methoxy-ethyl)-5-(pyridin-2-yloxymethyl)-1H-benzoimidazole 4-Bromo-2-(4-isopropyl-phenyl)-7-methoxy-1-(2-methoxy-ethyl)-5-(2-methoxy-phenoxymethyl)-1H-benzoimidazole {3-[4-Bromo-2-(4-isopropyl-phenyl)-7-methoxy-1-(2-methoxy-ethyl)-1H-benzoimidazol-5-ylmethoxy]-2-methyl-phenyl}-methanol 4-Bromo-2-(4-isopropyl-phenyl)-7-methoxy-1-(2-methoxy-ethyl)-5-(pyridin-3-yloxymethyl)-1H-benzoimidazole 4-Bromo-2-(4-isopropyl-phenyl)-5-(2-methanesulfonyl-phenoxymethyl)-7-methoxy-1-(2-methoxy-ethyl)-1H-benzoimidazole 2-{3-[4-Bromo-2-(4-isopropyl-phenyl)-7-methoxy-1-(2-methoxy-ethyl)-1H-benzoimidazol-5-ylmethoxy]-phenoxy}-ethanol 2-{2-[4-Bromo-2-(4-isopropyl-phenyl)-7-methoxy-1-(2-methoxy-ethyl)-1H-benzoimidazol-5-ylmethoxy]-phenyl}-acetamide 2-{2-[2-(4-Isopropyl-phenyl)-7-methoxy-1-(2-methoxy-ethyl)-4-trifluoromethyl-1H-benzoimidazol-5-ylmethoxy]-phenoxy}-ethanol 2-{2-[2-(4-Isopropyl-phenyl)-7-methoxy-1-(2-methoxy-ethyl)-4-trifluoromethyl-1H-benzoimidazol-5-ylmethoxy]-phenyl}-ethanol

[4-Bromo-2-(4-isopropyl-phenyl)-7-methoxy-1-(2-methoxy-ethyl)-1H-benzoimidazol-5-ylmethyl]-phenyl-amine

[4-Bromo-2-(4-isopropyl-phenyl)-7-methoxy-1-(2-methoxy-ethyl)-1H-benzoimidazol-5-ylmethyl]-(2-methanesulfonyl-phenyl)-amine

[4-Bromo-2-(4-isopropyl-phenyl)-7-methoxy-1-(2-methoxy-ethyl)-1H-benzoimidazol-5-ylmethyl]-[2-(2-methanesulfonyl-ethyl)-phenyl]-amine 2-(2{[4-Bromo-2-(4-isopropyl-phenyl)-7-methoxy-1-(2-methoxy-ethyl)-1H-benzoimidazol-5-ylmethyl]-amino}-phenyl)-acetamide 2-{[4-Bromo-2-(4-isopropyl-phenyl)-7-methoxy-1-(2-methoxy-ethyl)-1H-benzoimidazol-5-ylmethyl]-amino}-benzenesulfonic acid

[4-Bromo-2-(4-isopropyl-phenyl)-7-methoxy-1-(2-methoxy-ethyl)-1H-benzoimidazol-5-ylmethyl]-(2-fluoro-phenyl)-amine

[4-Bromo-2-(4-isopropyl-phenyl)-7-methoxy-1-(2-methoxy-ethyl)-1H-benzoimidazol-5-ylmethyl]-pyridin-2-yl-amine
2-{[4-Bromo-2-(4-isopropyl-phenyl)-7-methoxy-1-(2-methoxy-ethyl)-1H-benzoimidazol-5-ylmethyl]-amino}benzoic acid methyl ester
[4-Bromo-2-(4-isopropyl-phenyl)-7-methoxy-1-(2-methoxy-ethyl)-1H-benzoimidazol-5-ylmethyl]-pyridin-3-yl-amine
[4-Bromo-2-(4-isopropyl-phenyl)-7-methoxy-1-(2-methoxy-ethyl)-1H-benzoimidazol-5-ylmethyl]-methyl-phenyl-amine
[4-Bromo-2-(4-isopropyl-phenyl)-7-methoxy-1-(2-methoxy-ethyl)-1H-benzoimidazol-5-ylmethyl]-(3-methanesulfonyl phenyl)-amine
2-(2-{[2-(4-Isopropyl-phenyl)-7-methoxy-1-(2-methoxy-ethyl)-4-trifluoromethyl-1H-benzoimidazol-5-ylmethyl]-amino}-phenyl)-acetamide
[2-(4-isopropyl-phenyl)-7-methoxy-1-(2-methoxy-ethyl)-4-trifluoromethyl-1H-benzoimidazol-5-ylmethyl]-(2-methanesulfonyl-phenyl)-amine
[2-(4-Isopropyl-phenyl)-7-methoxy-1-(2-methoxy-ethyl)-4-trifluoromethyl-1H-benzoimidazol-5-ylmethyl]-[2-(2-methanesulfonyl-ethyl)-phenyl]-amine
1-[4-Bromo-2-(4-isopropyl-phenyl)-7-methoxy-1-(2-methoxy-ethyl)-1H-benzoimidazol-5-ylmethyl]-1H-imidazole-2-carboxylic acid methyl ester
1-[4-Bromo-2-(4-isopropyl-phenyl)-7-methoxy-1-(2-methoxy-ethyl)-1H-benzoimidazol-5-ylmethyl]-1H-imidazole-2-carboxylic acid dimethylamide
1-{1-[4-Bromo-2-(4-isopropyl-phenyl)-7-methoxy-1-(2-methoxy-ethyl)-1H-benzoimidazol-5-ylmethyl]-1H-imidazol-2-yl}-ethanone
1-[4-Bromo-2-(4-isopropyl-phenyl)-7-methoxy-1-(2-methoxy-ethyl)-1H-benzoimidazol-5-ylmethyl]-1H-indole-2,3-dione
4-Bromo-2-(4-isopropyl-phenyl)-7-methoxy-1-(2-methoxy-ethyl)-5-oxazol-2-ylmethyl-1H-benzoimidazole
1-[4-Bromo-2-(4-isopropyl-phenyl)-7-methoxy-1-(2-methoxy-ethyl)-1H-benzoimidazol-5-ylmethyl]-1H-imidazole-2-carbonitrile
1-[4-Bromo-2-(4-isopropyl-phenyl)-7-methoxy-1-(2-methoxy-ethyl)-1H-benzoimidazol-5-ylmethyl]-1H-imidazole-2-carboxylic acid methylamide
2-(4-Isopropyl-phenyl)-7-methoxy-1-(2-methoxy-ethyl)-5-bromo-4-trifluoromethyl-1H-benzoimidazole
[2-(4-Isopropyl-phenyl)-7-methoxy-1-(2-methoxy-ethyl)-4-trifluoromethyl-1H-benzoimidazol-5-ylmethyl]-phenyl-amine
[2-(4-Isopropyl-phenyl)-7-methoxy-1-(2-methoxy-ethyl)-4-trifluoromethyl-1H-benzoimidazol-5-ylmethyl]-pyridin-2-yl-amine
2-{[2-(4-Isopropyl-phenyl)-7-methoxy-1-(2-methoxy-ethyl)-4-trifluoromethyl-1H-benzoimidazol-5-ylmethyl]-amino}-benzenesulfonamide
2-(4-Isopropyl-phenyl)-7-methoxy-1-(2-methoxy-ethyl)-5-phenoxymethyl-4-trifluoromethyl-1H-benzoimidazole
2-(4-Isopropyl-phenyl)-7-methoxy-1-(2-methoxy-ethyl)-5-(pyridin-2-yloxymethyl)-4-trifluoromethyl-1H-benzoimidazole
2-[2-(4-Isopropyl-phenyl)-7-methoxy-1-(2-methoxy-ethyl)-4-trifluoromethyl-1H-benzoimidazol-5-ylmethoxy]-benzenesulfonamide
4-Bromo-2-(4-isopropyl-phenyl)-7-methoxy-1-(2-methoxy-ethyl)-5-(pyridin-2-yloxy)-1H-benzoimidazole According to a third aspect of the invention there is provided a pharmaceutical composition comprising a compound of formula (I) in association with a pharmaceutically acceptable excipient, diluent or carrier.

According to a fourth aspect of the invention there is provided a compound of formula (I) for promoting the release of parathyroid hormone.

It is now well established that controlled treatment of patients with parathyroid hormone (PTH) and analogues and fragments thereof can have a pronounced anabolic effect on bone formation. Thus compounds which promote PTH release, such as the compounds of the present invention may be used for preventing or treating conditions of bone which are associated with increased calcium depletion or resorption or in which stimulation of bone formation and calcium fixation in the bone is desirable.

Thus in a fifth aspect the invention includes a method for preventing or treating bone conditions which are associated with increased calcium depletion or resorption or in which stimulation of bone formation and calcium fixation in the bone is desirable in which an effective amount of a compound of formula (I) as defined above, or a pharmaceutically-acceptable and—cleavable ester, or acid addition salt thereof is administered to a patient in need of such treatment.

In a sixth aspect the invention provides a process for preparation of a compound of formula (I) in free or salt form, comprising:

(a) introducing a group R4 into a corresponding compound of formula II, R4 being as defined above:

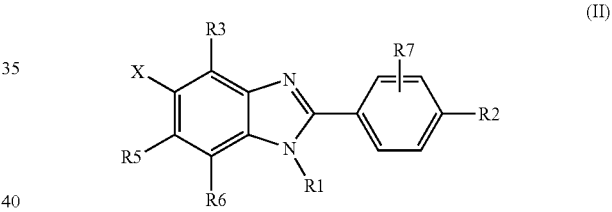

wherein X is any suitable group capable of substitution by R4 and wherein R1, R2, R3, R5, R6 and R7 are as defined above; or (b) for the preparation of compounds wherein R4 is an aryl-CH$_2$ group, appropriately introducing such aryl group by reaction with a compound of formula III:

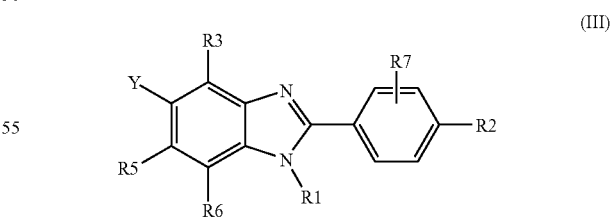

wherein Y denotes either:

(i) a leaving group-CH$_2$— and R1, R2, R3, R5, R6 and R7 are as defined above; or (ii) the group —CH=O; or (c) introducing a group R3 into a corresponding compound of formula IV, R3 being as defined above:

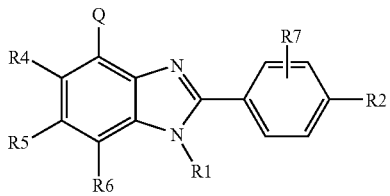

(IV)

wherein Q is any suitable group capable of substitution by R3 and wherein R1, R2, R4, R5, R6 and R7 are as defined above; or
(d) appropriately N-substituting a corresponding compound of formula V by a group R1 as defined above:

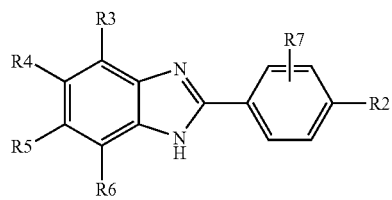

(V)

wherein R2-R7 are as defined above; or
(e) for the preparation of compounds wherein R4 is aryl-CO—, oxidizing a compound of formula (VI):

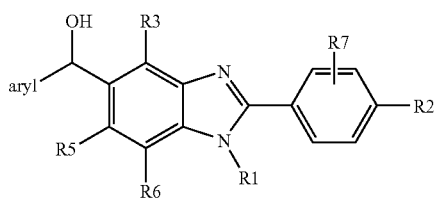

(VI)

with a suitable oxidizing agent, R1, R2, R3, R5, R6 and R7 being as defined above;
(f) treating a compound of formula (VII):

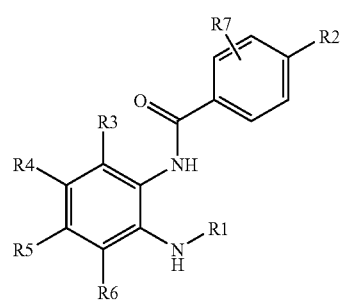

(VII)

under suitable conditions to effect ring closure, R1-R7 being as defined above;
[***Marc, can we use this reaction for all cpds of formula (I), or only when certain substituents are present?**]
transforming the resultant compound into further compound of formula I if appropriate;
and recovering the resultant compounds of formula I in free or salt form.

The process of the invention is effected in a conventional manner. In process variant (a), X is conveniently an iodide group and the transformation is suitably performed by Suzuki coupling, for example by reacting compound II with aryl or heteroaryl-B(OH)$_2$ in the presence of a palladium catalyst. In process variant (b), Y is conveniently a methanesulfonic acid methyl ester group and compound III may be reacted with the desired aryl or heteroaryl R4 group in the presence of a base such as sodium hydride in a suitable solvent such as DMF. Alternatively in process variant (b), when Y denotes the group —CH=O, the compound of formula (III) may be reacted with a Grignard reagent denoted by arylMgBr in a suitable solvent e.g. THF to produce, after subsequent treatment with phosphinic acid and iodine, the corresponding compound of formula (I). In process variant (c), R3 may for example represent a bromo group which may be introduced by reacting N-bromosuccinimide or Br$_2$/acetic acid in a suitable solvent with a compound of formula IV wherein Q denotes H. Process variant (d) is an N-alkylation in which R1 is conveniently an alkyl group and may be introduced by reacting a corresponding bromoalkyl with a compound of formula V in the presence of a base such as sodium hydride in suitable solvent, for example DMF. A suitable oxidizing agent in process (e) is for example oxalyl chloride in DMSO in a Swern oxidation reaction. In process variant (f), ring closure is conveniently effected by heating to 100° C. with acetic acid.

If desired, the compound obtained may be further transformed into another compound of formula I. For example, an aryl ring substituent OH may be transformed to a 2-methoxy-ethoxy group conveniently by reaction with 2-(bromoethyl)-methyl ether in the presence of a base.

The compounds of formula I in free form may be converted into salt forms in conventional manner and vice-versa.

The compounds of the invention can be recovered from the reaction mixture and purified in conventional manner. Isomers, such as enantiomers, may be obtained in conventional manner, e.g. by fractional crystallization or asymmetric synthesis from corresponding asymmetrically substituted, e.g. optically active starting materials.

In a seventh aspect invention includes the use of a compound of formula (I) in the manufacture of a medicament for preventing or treating bone conditions which are associated with increased calcium depletion or resorption or in which stimulation of bone formation and calcium fixation in the bone is desirable.

Agents of the invention may be prepared by processes described below:

EXAMPLE 1

4-Bromo-2-(4-isopropyl-phenyl)-7-methoxy-1-(2-methoxy-ethyl)-1H-benzoimidazole

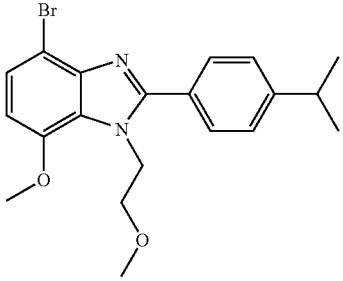

To a stirred solution of 500 mg (1.45 mmol) 4-bromo-2-(4-isopropyl-phenyl)-7-methoxy-1H-benzoimidazole in 11 ml DMF, NaH (38 mg, 1.6 mmol) is added and stirring is continued for 1 h at RT, and then the reaction mixture is heated to 60° C. 0.152 ml (0.175 mmol) (2-bromoethyl)-methyl ether is added and stirring is continued at this temperature for another 6 h. The reaction mixture is cooled to room temperature, poured into water and extracted (3×) with ethyl acetate. The combined organic layers are washed with water (2×) and brine, dried over MgSO$_4$, filtered and concentrated in vacuo. The residue is purified by flash-chromatography on silica gel (hexane:EtOAc=3:1) to afford 398 mg of the title compound as colorless oil.

R$_t$=2.23 min (Waters Symmetry C8, 2.1×50 mm, detection 210-250 nM, 10% to 95% CH$_3$CN in H$_2$O in 2 min+0.05% TFA, flow rate 1.0 ml/min)

MS: 403 (M+1)$^+$ ($^{79}$Br), 405 (M+1)$^+$ ($^{81}$Br)

The starting materials can be prepared as follows:

a) 4-Bromo-2-(4-isopropyl-phenyl)-7-methoxy-1H-benzoimidazole

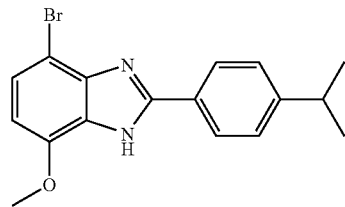

A solution of 1.44 g (3.97 mmol) N-(2-amino-3-bromo-6-methoxy-phenyl)-4-isopropyl-benzamide in 25 ml glacial acetic acid is stirred at 100° C. for 3 h. The reaction mixture is cooled to room temperature 200 ml ethyl acetate is added. The solution is washed with 4N NaOH (2×) and with water and brine, dried over MgSO$_4$, filtered and concentrated in vacuo. The residue is purified by flash-chromatography on silica gel (hexane:EtOAc=2:1) to afford 1.12 g of the title compound as slightly reddish solid.

b) N-(2-Amino-3-bromo-6-methoxy-phenyl)-4-isopropyl-benzamide

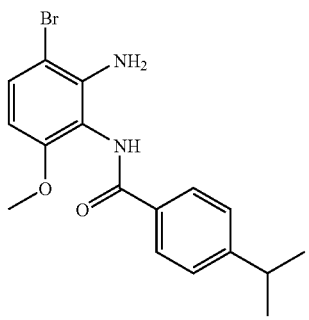

A solution of 870 mg (4.01 mmol) 3-bromo-6-methoxy-benzene-1,2-diamine, 1.16 g (6.0 mmol) EDC, 744 mg (6.0 mmol) DMAP and 707 mg (4.01 mmol) 4-isopropylbenzoic acid in 20 ml dichloromethane is stirred at room temperature for 72 h. The reaction mixture is concentrated in vacuo. The residue is purified by flash-chromatography on silica gel (hexane:EtOAc=2:1) to afford 1.44 g of the title compound as a slightly reddish solid.

c) 3-bromo-6-methoxy-benzene-1,2-diamine

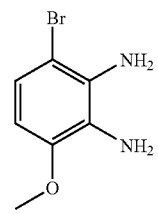

A solution of 1.12 g (4.04 mmol) 1-bromo-4-methoxy-2,3-dinitro-benzene in 25 ml THF is hydrogenated in the presence of 100 mg Raney-Nickel (B113W Degussa) at normal pressure for 3 h. The catalyst is filtered off and the filtrate is concentrated in vacuo to afford 871 mg of the title compound as a grey crystalline solid.

d) 1-Bromo-4-methoxy-2,3-dinitro-benzene

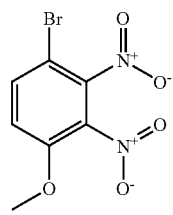

1.0 g (4.3 mmol) 4-bromo-3-nitroanisole is nitrated by dropwise addition of 1.0 ml of a mixture of 0.4 ml nitric acid (100%) and 0.6 ml concentrated sulfuric acid. Stirring is continued for 1 h. After that the reaction mixture is poured on water and extracted (3×) with ethyl acetate. The combined organic layers are washed with water and brine (2×), dried over MgSO$_4$, filtered and concentrated in vacuo. The residue is purified by flash-chromatography on silica gel (hexane:EtOAc=1:1) to afford 630 mg of the title compound as yellow crystals.

EXAMPLE 2

4-Iodo-2-(4-isopropyl-phenyl)-7-methoxy-1-(2-methoxy-ethyl)-1H-benzoimidazole

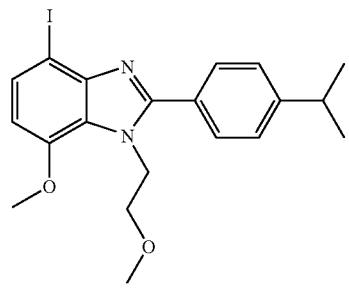

The title compound is prepared starting from 4-iodo-2-(4-isopropyl-phenyl)-7-methoxy-1H-benzoimidazole and (2-bromoethyl)-methyl ether using the same reaction conditions as described in Example 1. The title compound is obtained as a colorless oil.

$R_t$=2.31 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 451 (M+1)$^+$

The starting material 4-iodo-2-(4-isopropyl-phenyl)-7-methoxy-1H-benzoimidazole is prepared from 4-iodo-3-nitro-anisole using exactly the same methodology as described for in Example 1a)-d).

EXAMPLE 3

4-Iodo-2-(4-isopropyl-phenyl)-7-methoxy-1-(2-methylsulfanyl-ethyl)-1H-benzoimidazole

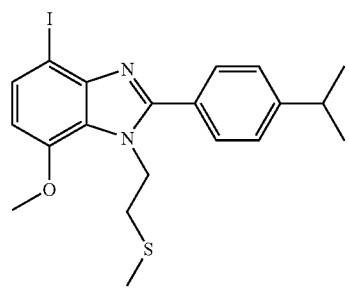

Using 1-bromo-2-methylsulfanyl-ethane instead of (2-bromoethyl)-methyl ether the title compound is prepared using the same reaction conditions as described for the preparation of Example 1.

$R_t$=2.47 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 467 (M+1)$^+$

EXAMPLE 4

4-Bromo-2-(4-isopropyl-phenyl)-7-methoxy-1-(2-methylsulfanyl-ethyl)-1H-benzoimidazole

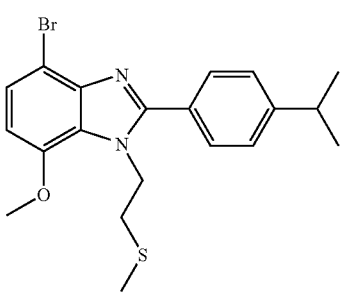

Using 1-bromo-2-methylsulfanyl-ethane instead of (2-bromoethyl)-methyl ether the title compound is prepared using the same reaction conditions as described for the preparation of Example 1.

$R_t$=2.36 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 419 (M+1)$^+$ ($^{79}$Br), 421 (M+1)$^+$ ($^{81}$Br)

EXAMPLE 5

4-Bromo-1-cyclopropylmethyl-2-(4-isopropyl-phenyl)-7-methoxy-1H-benzoimidazole

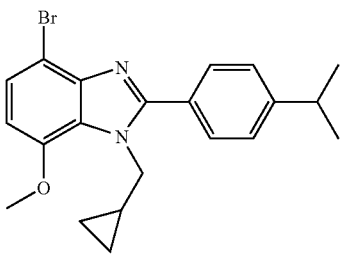

Using bromomethyl-cyclopropane instead of (2-bromoethyl)-methyl ether the title compound is prepared using the same reaction conditions as described for the preparation of Example 1.

$R_t$=2.34 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 399 (M+1)$^+$ ($^{79}$Br), 401 (M+1)$^+$ ($^{81}$Br)

EXAMPLE 6

4-Bromo-1-propyl-2-(4-isopropyl-phenyl)-7-methoxy-1H-benzoimidazole

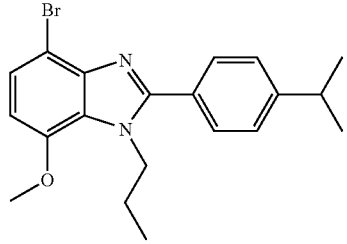

Using 1-bromo-propane instead of (2-bromoethyl)-methyl ether the title compound is prepared using the same reaction conditions as described for the preparation of Example 1.

$R_t$=2.31 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 387 (M+1)$^+$ ($^{79}$Br), 389 (M+1)$^+$ ($^{81}$Br)

EXAMPLE 7

4-Bromo-1-butyl-2-(4-isopropyl-phenyl)-7-methoxy-1H-benzoimidazole

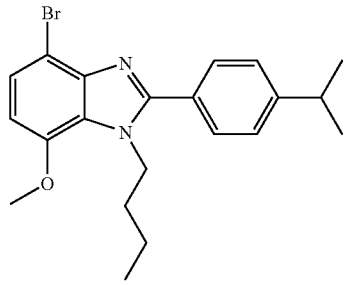

Using 1-bromo-butane instead of (2-bromoethyl)-methyl ether the title compound is prepared using the same reaction conditions as described for the preparation of Example 1.

$R_t$=2.41 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 401 (M+1)$^+$ ($^{79}$Br), 403 (M+1)$^+$ ($^{81}$Br)

EXAMPLE 8

4-Bromo-1-ethyl-2-(4-isopropyl-phenyl)-7-methoxy-1H-benzoimidazole

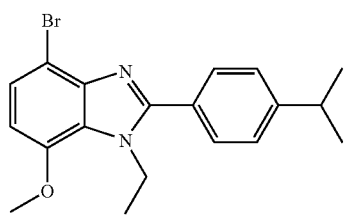

Using 1-bromo-ethane instead of (2-bromoethyl)-methyl ether the title compound is prepared using the same reaction conditions as described for the preparation of Example 1.

$R_t$=2.23 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 373 (M+1)$^+$ ($^{79}$Br), 375 (M+1)$^+$ ($^{81}$Br)

EXAMPLE 9

{2-[4-Bromo-2-(4-isopropyl-phenyl)-7-methoxy-benzoimidazol-1-yl]-ethyl}-dimethyl-amine

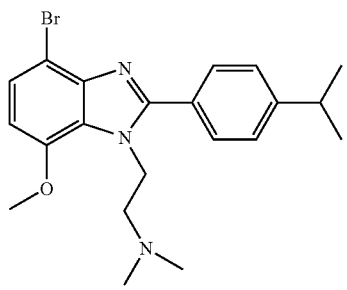

Using (2-Bromo-ethyl)-dimethyl-amine instead of (2-bromoethyl)-methyl ether the title compound is prepared using the same reaction conditions as described for the preparation of Example 1.

$R_t$=1.86 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 416 (M+1)$^+$ ($^{79}$Br), 418 (M+1)$^+$ ($^{81}$Br)

EXAMPLE 10

4-Chloro-2-(4-isopropyl-phenyl)-7-methoxy-1-(2-methoxy-ethyl)-1H-benzoimidazole

The title compound is prepared starting from 4-chloro-2-(4-isopropyl-phenyl)-7-methoxy-1H-benzoimidazole and (2-bromoethyl)-methyl ether using the same reaction conditions as described in Example 1. The title compound is obtained as a colorless oil.

$R_t$=2.18 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 359 (M+1)$^+$

The starting material 4-chloro-2-(4-isopropyl-phenyl)-7-methoxy-1H-benzoimidazole is prepared from 4-chloro-3-nitro-anisole using exactly the same methodology as described in Example 1a)-d).

EXAMPLE 11

4-Ethynyl-2-(4-isopropyl-phenyl)-7-methoxy-1-(2-methoxy-ethyl)-1H-benzoimidazole

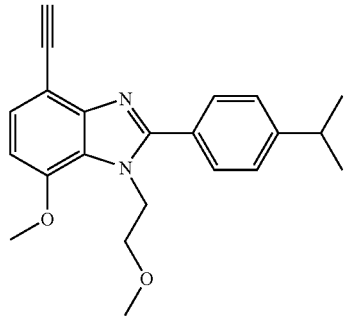

A mixture of 17 mg (0.04 mmol) 2-(4-isopropyl-phenyl)-7-methoxy-1-(2-methoxy-ethyl)-4-trimethylsilanylethynyl-1H-benzoimidazole and 0.5 ml 1N NaOH in 2 ml THF/methanol (1:1) is stirred for 1 hour at 60° C. The reaction mixture is cooled to room temperature and poured on water and extracted (3×) with ethyl acetate. The combined organic layers are washed with water and brine, dried over MgSO$_4$, filtered and concentrated in vacuo. The residue is purified on 0.5 mm silica gel plates (hexane:EtOAc=3:1) to afford 7 mg of the title compound as yellow oil.

$R_t$=2.11 min (Waters Symmetry C8, 2.1×50 mm, detection 210-250 nM, 10% to 95% CH$_3$CN in H$_2$O in 2 min+0.05% TFA, flow rate 1.0 mL/min)

MS: 349 (M+1)$^+$ 2-(4-Isopropyl-phenyl)-7-methoxy-1-(2-methoxy-ethyl)-4-trimethylsilanylethynyl-1H-benzoimidazole can be prepared using the following procedure:

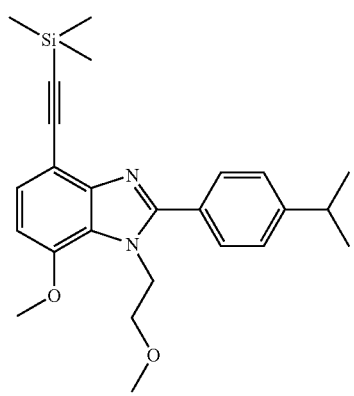

A mixture of 50 mg (0.111 mmol) 4-iodo-2-(4-isopropyl-phenyl)-7-methoxy-1-(2-methoxy-ethyl)-1H-benzoimidazole, 0.1 ml (0.77 mmol) triethylamine, 0.1 ml (0.7 mmol) ethinyltrimethylsilane and 5 mg palladium-II-acetate in 1 ml acetonitrile is stirred at 50° C. for 3 hours. Then the reaction mixture is cooled to room temperature and poured on water and extracted (3×) with ethyl acetate. The combined organic layers are washed with water and brine, dried over MgSO$_4$, filtered and concentrated in vacuo. The residue is purified by flash-chromatography on silica gel (hexane:EtOAc=3:1) to afford 17 mg of the title compound as colorless oil.

EXAMPLE 12

2-(4-Isopropyl-phenyl)-7-methoxy-1-(2-methoxy-ethyl)-4-phenyl-1H-benzoimidazole

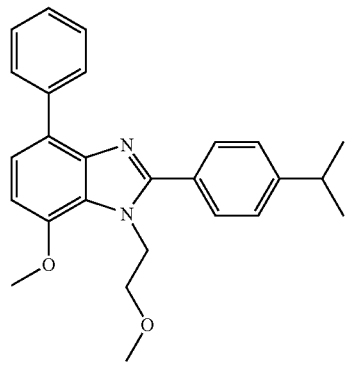

A mixture of 100 mg (0.25 mmol) 4-bromo-2-(4-isopropyl-phenyl)-7-methoxy-1-(2-methoxy-ethyl)-1H-benzoimidazole, 45 mg (0.424 mmol) sodium carbonate, 34 mg (0.275 mmol) phenyl-boronic acid and 10 mg tetrakis(triphenylphosphine) palladium in 10 ml toluene/water (3:1) is stirred at 100° C. for 9 hours. Then the reaction mixture is cooled to room temperature and poured on water and extracted (3×) with ethyl acetate. The combined organic layers are washed with water (2×) and brine, dried over MgSO$_4$, filtered and concentrated in vacuo. The residue is purified by flash-chromatography on silica gel (hexane:EtOAc=4:1) to afford 53 mg of the title compound as a white crystalline solid.

$R_t$=2.21 min (Waters Symmetry C8, 2.1×50 mm, detection 210-250 nM, 10% to 95% CH$_3$CN in H$_2$O in 2 min+0.05% TFA, flow rate 1.0 ml/min)

MS: 401 (M+1)$^+$

EXAMPLE 13

3-[2-(4-Isopropyl-phenyl)-7-methoxy-1-(2-methoxy-ethyl)-1H-benzoimidazol-4-yl]-phenol

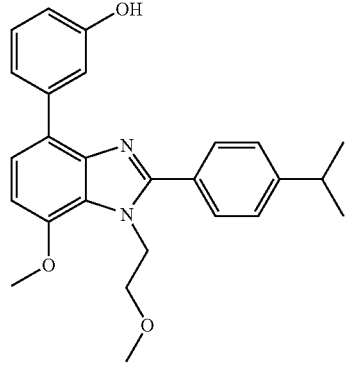

The title compound is obtained using 3-hydroxyphenyl-boronic acid instead of phenyl-boronic acid using the same procedure as described for the preparation of Example 12 as a white crystalline solid.

$R_t$=2.07 min (Waters Symmetry C8, 2.1×50 mm, detection 210-250 nM, 10% to 95% CH$_3$CN in H$_2$O in 2 min+0.05% TFA, flow rate 1.0 ml/min)

MS: 417 (M+1)$^+$

EXAMPLE 14

2-(4-Isopropyl-phenyl)-7-methoxy-4-[3-(2-methoxy-ethoxy)-phenyl]-1-(2-methoxy-ethyl)-1H-benzoimidazole

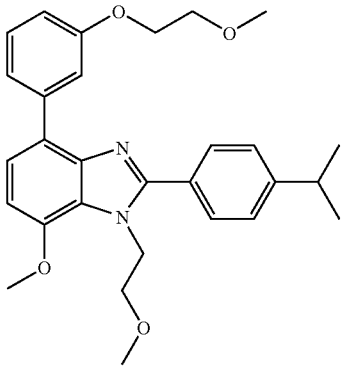

5 mg (0.2 mmol) NaH is added to a solution of 70 mg (0.173 mmol) 3-[2-(4-isopropyl-phenyl)-7-methoxy-1-(2-methoxy-ethyl)-1H-benzoimidazol-4-yl]-phenol in 2 ml DMF. This mixture is stirred at room temperature for 1 h. After that 28 mg (0.207 mmol) 2-(bromoethyl)-methyl ether is added and stirring is continued for another 3 h. The reaction mixture is poured on water and extracted (3×) with ethyl acetate. The combined organic layers are washed with water (2×) and brine, dried over MgSO$_4$, filtered and concentrated in vacuo. The residue is purified by flash-chromatography on silica gel (hexane:EtOAc=3:1) to afford 70 mg of the title compound as a colorless oil.

$R_t$=2.18 min (Waters Symmetry C8, 2.1×50 mm, detection 210-250 nM, 10% to 95% CH$_3$CN in H$_2$O in 2 min+0.05% TFA, flow rate 1.0 ml/min)

MS: 475 (M+1)$^+$

EXAMPLE 15

4-(3,5-Dimethoxy-phenyl)-2-(4-isopropyl-phenyl)-7-methoxy-1-(2-methoxy-ethyl)-1H-benzoimidazole

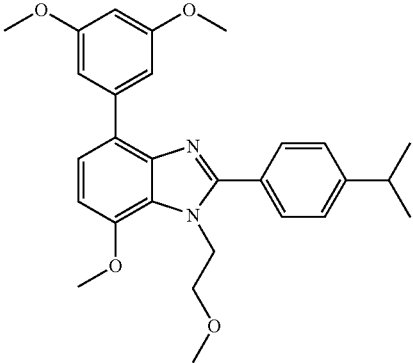

The title compound is obtained using 3,5-dimethoxyphenyl-boronic acid instead of phenyl-boronic acid using the same procedure as described for the preparation of Example 12 as a colorless oil.

$R_t$=2.20 min (Waters Symmetry C8, 2.1×50 mm, detection 210-250 nM, 10% to 95% CH$_3$CN in H$_2$O in 2 min+0.05% TFA, flow rate 1.0 ml/min)

MS: 461 (M+1)$^+$

EXAMPLE 16

4-Methyl-2-(4-isopropyl-phenyl)-7-methoxy-1-(2-methoxy-ethyl)-1H-benzoimidazole

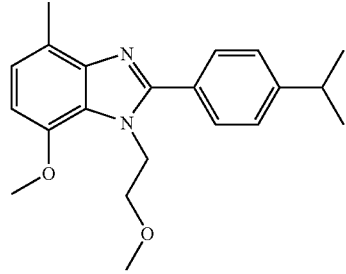

The title compound is prepared starting from 4-methyl-2-(4-isopropyl-phenyl)-7-methoxy-1H-benzoimidazole and (2-bromoethyl)-methyl ether using the same reaction conditions as described in Example 1. The title compound is obtained as a colorless oil.

$R_t$=2.01 min (Waters Symmetry C8, 2.1×50 mm, detection 210-250 nM, 10% to 95% CH$_3$CN in H$_2$O in 2 min+0.05% TFA, flow rate 1.0 ml/min)

MS: 339 (M+1)$^+$

The starting material 4-methyl-2-(4-isopropyl-phenyl)-7-methoxy-1H-benzoimidazole is prepared from 4-methyl-3-nitro-anisole using the same method as described in Example 1 a)-d).

EXAMPLE 17

4-Ethyl-2-(4-isopropyl-phenyl)-7-methoxy-1-(2-methoxy-ethyl)-1H-benzoimidazole

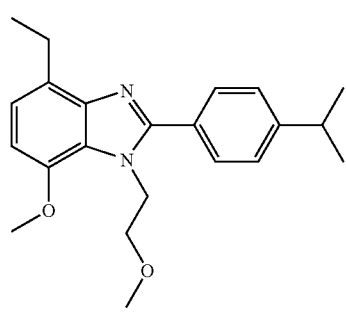

To a solution of 150 mg (0.223 mmol) 4-bromo-2-(4-isopropyl-phenyl)-7-methoxy-1-(2-methoxy-ethyl)-1H-benzoimidazole in 8 ml THF, 0.289 ml tert-butyllithium (1.7M in pentane) is slowly added at −78° C. This mixture is stirred for 1 h at −78° C. then 54 μl (0.669 mmol) ethyl iodide is added. The reaction mixture is warmed to room temperature and stirring is continued for 12 h. The reaction mixture is cooled to room temperature, poured on water and extracted (3×) with ethyl acetate. The combined organic layers are washed with water (2×) and brine, dried over MgSO$_4$, filtered and concentrated in vacuo. The residue is purified by flash-chromatography on silica gel (hexane:EtOAc=2:1) to afford 25 mg of the title compound as a colorless oil.

R$_t$=2.05 min (Waters Symmetry C8, 2.1×50 mm, detection 210-250 nM, 10% to 95% CH$_3$CN in H$_2$O in 2 min+0.05% TFA, flow rate 1.0 ml/min)

MS: 353 (M+1)$^+$

EXAMPLE 18

4-Ethylsulfanyl-2-(4-isopropyl-phenyl)-7-methoxy-1-(2-methoxy-ethyl)-1H-benzoimidazole

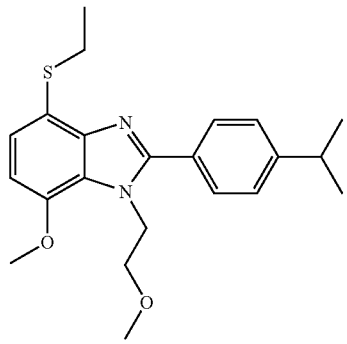

NaH (2.4 mg, 0.1 mmol) is added to a solution of 7-ethylsulfanyl-2-(4-isopropyl-phenyl)-3-(2-methoxy-ethyl)-3H-benzoimidazol-4-ol (35 mg, 0.094 mmol) in 1 ml DMF. The mixture is stirred at room temperature for 1 h and methyl iodide (6 μl, 0.1 mmol) is added. Stirring is continued for 1 h, then the reaction mixture is poured on water and extracted (3×) with ethyl acetate.

The combined organic layers are washed with water (2×) and brine, dried over MgSO$_4$, filtered and concentrated in vacuo. The residue is purified by flash-chromatography on silica gel (hexane:EtOAc=4:1) to afford 11 mg of the title compound as a colorless oil.

R$_t$=2.13 min (Waters Symmetry C8, 2.1×50 mm, detection 210-250 nM, 10% to 95% CH$_3$CN in H$_2$O in 2 min+0.05% TFA, flow rate 1.0 ml/min)

MS: 385 (M+1)$^+$

The starting material is prepared as follows:

7-Ethylsulfanyl-2-(4-isopropyl-phenyl)-3-(2-methoxy-ethyl)-3H-benzoimidazol-4-ol

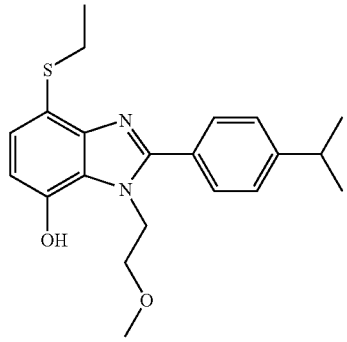

A mixture of 300 mg (0.744 mmol) 4-bromo-2-(4-isopropyl-phenyl)-7-methoxy-1-(2-methoxy-ethyl)-1H-benzoimidazole (example 1) and 313 mg (3.72 mmol) EtSNa in 2 ml DMF is stirred at reflux temperature for 4 h. after that the reaction mixture is poured on 10 ml conc. HCl, stirred for 10 min, diluted with water 25 ml and extracted (3×) with ethyl acetate. The combined organic layers are washed with water (2×) and brine, dried over MgSO$_4$, filtered and concentrated in vacuo. The residue is purified by flash-chromatography on silica gel (hexane:EtOAc=3:1) to afford 35 mg of the title compound as a colorless oil.

EXAMPLE 19

4-Bromo-2-(4-cyclopropyl-phenyl)-7-methoxy-1-(2-methoxy-ethyl)-1H-benzoimidazole

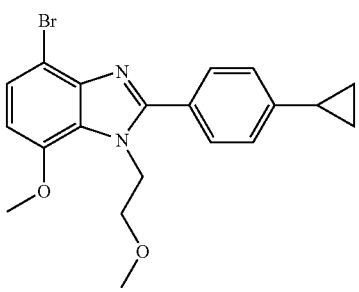

The title compound and the precursors can be prepared using the same synthesis sequence as described in example 1. Instead of 4-isopropylbenzoic acid, 4-cyclopropyl-benzoic acid is used in step b).

R$_t$=2.06 min (Waters Symmetry C8, 2.1×50 mm, detection 210-250 nM, 10% to 95% CH$_3$CN in H$_2$O in 2 min+0.05% TFA, flow rate 1.0 ml/min)

MS: 401 (M+1)$^+$ ($^{79}$Br), 403 (M+1)$^+$ ($^{81}$Br)

Similarly, by using the appropriate alkyl-bromides, the following compounds can be prepared:

EXAMPLE 20

4-Bromo-2-(4-cyclopropyl-phenyl)-7-methoxy-1-(2-methylsulfanyl-ethyl)-1H-benzoimidazole

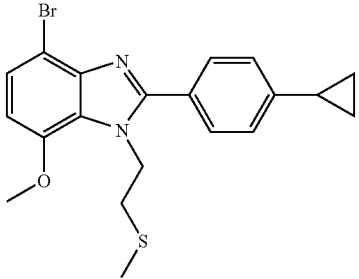

R$_t$=2.169 min (Waters Symmetry C8, 2.1×50 mm, detection 210-250 nM, 10% to 95% CH$_3$CN in H$_2$O in 2 min+0.05% TFA, flow rate 1.0 ml/min)

MS: 417 (M+1)$^+$ ($^{79}$Br), 419 (M+1)$^+$ ($^{81}$Br)

EXAMPLE 21

4-Bromo-1-cyclopropylmethyl-2-(4-cyclopropyl-phenyl)-7-methoxy-1H-benzoimidazole

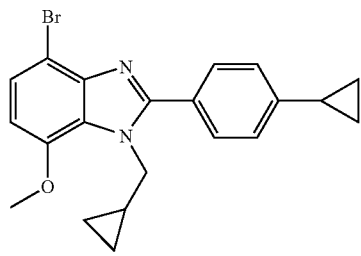

$R_t$=2.174 min (Waters Symmetry C8, 2.1×50 mm, detection 210-250 nM, 10% to 95% $CH_3CN$ in $H_2O$ in 2 min+ 0.05% TFA, flow rate 1.0 ml/min)

MS: 397 $(M+1)^+$ ($^{79}Br$), 399 $(M+1)^+$ ($^{81}Br$)

EXAMPLE 22

5-Bromo-2-(4-isopropyl-phenyl)-7-methoxy-1-(2-methoxy-ethyl)-1H-benzoimidazole

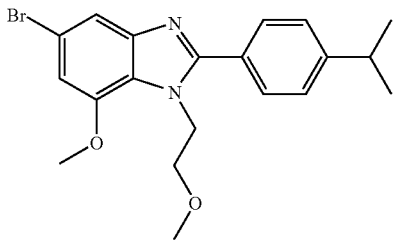

The title compound and the precursors can be prepared using the same synthesis sequence as described in example 1 from 5-Bromo-3-methoxy-benzene-1,2-diamine.

$R_t$=2.13 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 403 $(M+1)^+$ ($^{79}Br$), 405 $(M+1)^+$ ($^{81}Br$)

a) 5-Bromo-3-methoxy-benzene-1,2-diamine

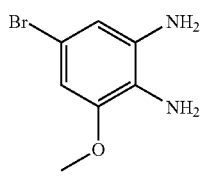

A solution of 2.0 g (8.1 mmol) 4-Bromo-2-methoxy-6-nitro-phenylamine [Zhou, Q-T., et al. *Huaxue Xuebao* 1980, 38(5), 507-10] in 50 ml methanol/water (2:1) is hydrogenated in the presence of 200 mg Pt/C (Engelhard 4709) at normal pressure for 3 h. Then the catalyst is filtered off and the filtrate is concentrated in vacuo to afford 1.5 g of the title compound as an oil.

An alternative way for the preparation of the compound described in example 22 is outlined below:

a) 2-Methoxy-6-nitro-phenylamine

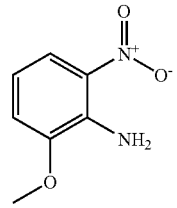

To a stirred solution of 20 g (129.9 mmol) 2-hydroxy-6-nitroaniline in 150 ml DMF, NaH (3.42 g, 143 mmol, 95%) is added at 0° C. and stirring is continued for 1.5 h. MeI (9.3 ml, 150 mmol) is added and the reaction mixture is stirred at room temperature for 1 h. After that the reaction mixture is poured on water and extracted (3×) with ethyl acetate. The combined organic layers are washed with water (2×) and brine, dried over $MgSO_4$, filtered and concentrated in vacuo. To the residue 50 ml of hexane:diethyl ether=4:1 is added and the resulting suspension is stirred for 5 minutes. 20 g of the title compound are obtained after filtration of the mixture as a brown crystalline solid.

b) 2-Chloro-1-methoxy-3-nitro-benzene

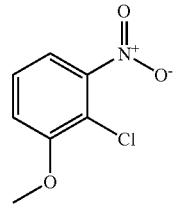

To a mixture consisting of 15.5 g (92.26 mmol) 2-methoxy-6-nitro-phenylamine, 31 ml water and 31 ml conc. HCl, a solution of 6.36 g (92.26 mmol) $NaNO_2$ in 38 ml water is slowly added dropwise at –10° C.-0° C. After stirring for 0.5 h the mixture is slowly added to a solution of 11.88 g (120 mmol) CuCl in 93 ml conc. HCl. After completion of the addition stirring is continued for 1.5 h at room temperature and for 0.5 h at reflux temperature. The reaction mixture is allowed to cool to room temperature and is poured on water and extracted (3×) with ethyl acetate. The combined organic layers are washed with water (2×) and brine, dried over $MgSO_4$, filtered and concentrated in vacuo. The residue is purified by flash-chromatography on silica gel (hexane:EtOAc=3:1) to afford 12.69 of the title compound as a crystalline solid.

c) (2-Methoxy-ethyl)-(2-methoxy-6-nitro-phenyl)-amine

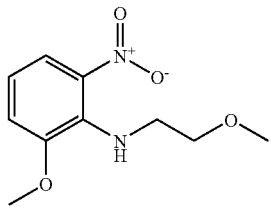

A mixture of 7.5 g (40 mmol) 2-chloro-1-methoxy-3-nitro-benzene, 14 ml diisopropylethylamine and 35 ml 2-methoxy-ethyl amine is heated (180° C. oil bath temperature) in a closed steel reactor for 25 min. Then the reaction mixture is cooled to room temperature and is concentrated in vacuo (3× coevaporation with toluene) to obtain ca. 20 g (which contains 85% of the title compound) of a red oil which is used without further purification in the next step.

d) (4-Bromo-2-methoxy-6-nitro-phenyl)-(2-methoxy-ethyl)-amine

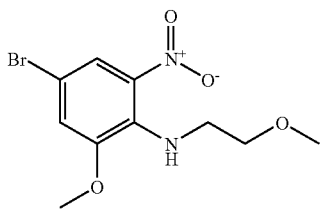

To a solution of ca. 20 g (contains 15.65 g, 58.9 mmol) (2-methoxy-ethyl)-(2-methoxy-6-nitro-phenyl)-amine in 150 ml glacial acetic acid, 3.0 ml (58.9 mmol) bromine is slowly added at room temperature. The reaction mixture is stirred at room temperature for 3 h. 600 ml EtOAc are added and this solution is washed with 4n NaOH (2×), water and brine, dried over MgSO₄, filtered and concentrated in vacuo. The residue is recrystallized from diethyl ether/hexane to afford 13 g of the pure title compound as orange crystals and 6.6 g of an orange oil which contained 50% of the starting material.

e) 5-Bromo-3-methoxy-N*2*-(2-methoxy-ethyl)-benzene-1,2-diamine

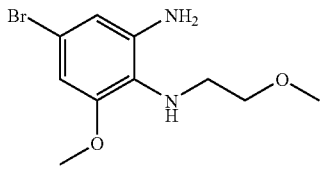

A solution of 6.19 (20 mmol) (4-bromo-2-methoxy-6-nitro-phenyl)-(2-methoxy-ethyl)-amine in 140 ml THF is hydrogenated in the presence of 1.4 g Raney-Nickel (B113W Degussa) at normal pressure for 25 h. The catalyst is filtered off and the filtrate is concentrated in vacuo. The residue is purified by flash-chromatography on silica gel (hexane:EtOAc=2:1) to afford 4.95 g of the title compound as a as a reddish oil.

f) N-[5-Bromo-3-methoxy-2-(2-methoxy-ethylamino)-phenyl]-4-isopropyl-benzamide

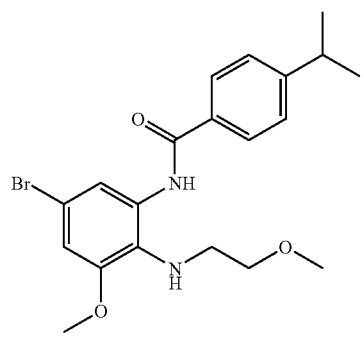

A solution of 4.95 g (18 mmol) 5-bromo-3-methoxy-N*2*-(2-methoxy-ethyl)-benzene-1,2-diamine, 5.15 g (27 mmol) EDC, 3.3 g (27 mmol) 4-dimethylamino-pyridine and 2.94 g (18 mmol) 4-isopropyl benzoic acid in 150 ml dichloromethane is stirred at room temperature for 14 h. After that 400 ml EtOAc are added and the organic phase washed with water (2×) and brine, dried over MgSO₄, filtered and concentrated in vacuo. The residue is purified by flash-chromatography on silica gel (hexane:EtOAc=3:1) to afford 7.48 g of the title compound as a reddish oil.

g) 5-Bromo-2-(4-isopropyl-phenyl)-7-methoxy-1-(2-methoxy-ethyl)-1H-benzoimidazole

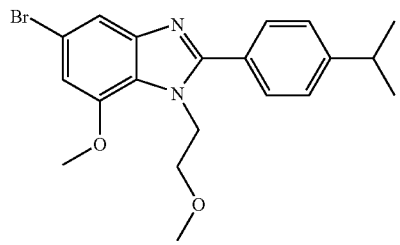

A solution of 748 mg (1.77 mmol) N-[5-bromo-3-methoxy-2-(2-methoxy-ethylamino)-phenyl]-4-isopropyl-benzamide in 10 ml AcOH is stirred at 100° C. for 2 h. The reaction mixture is cooled to room temperature 200 ml ethyl acetate is added. The solution is washed with 4N NaOH (2×) and with water and brine, dried over MgSO₄, filtered and concentrated in vacuo. The residue is purified by flash-chromatography on silica gel (hexane:EtOAc=3:1) to afford 625 mg of the title compound as a colorless solid.

EXAMPLE 23

4,5-Dibromo-2-(4-isopropyl-phenyl)-7-methoxy-1-(2-methoxy-ethyl)-1H-benzoimidazole

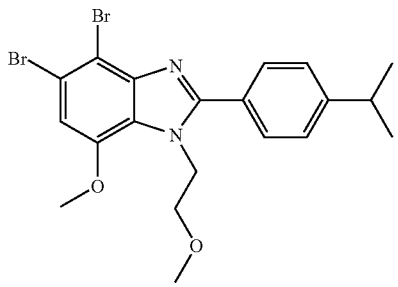

To a solution of 403 mg (1.0 mmol) 5-bromo-2-(4-isopropyl-phenyl)-7-methoxy-1-(2-methoxy-ethyl)-1H-benzoimidazole in 8 ml glacial acetic acid, 240 mg (1.5 mmol) bromine is slowly added at 10° C. The reaction mixture is allowed to warm to room temperature and is stirred for 3 h. 250 ml EtOAc are added and this solution is washed 1 n NaOH (2×), water and brine, dried over MgSO$_4$, filtered and concentrated in vacuo. The residue is recrystallized from EtOAc/hexane to afford 30 mg of the title compound as colorless crystals.

$R_f$=0.23 (hexane/EtOAc=3:1)

MS: 481 (M+1)$^+$ (2×$^{79}$Br), 483 (M+1)$^+$ ($^{79}$Br, $^{81}$Br), 485 (M+1)$^+$ (2×$^{81}$Br)

EXAMPLE 24

4,5-Dibromo-2-(4-cyclopropyl-phenyl)-7-methoxy-1-(2-methoxy-ethyl)-1H-benzoimidazole

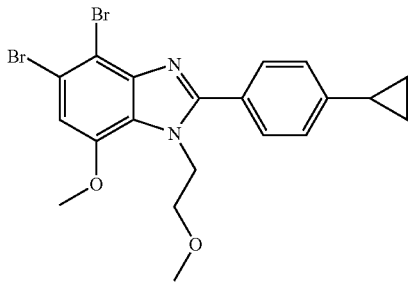

The compound is prepared as described in example 23 by using 4-cyclpropyl-benzoic acid instead of 4-isopropyl-benzoic acid.

$R_t$=2.455 min (Waters Symmetry C8, 2.1×50 mm, detection 210-250 nM, 10% to 95% CH$_3$CN in H$_2$O in 2 min+0.05% TFA, flow rate 1.0 ml/min)

MS: 479 (M+1)$^+$ (2×$^{79}$Br), 481 (M+1)$^+$ ($^{79}$Br, $^{81}$Br), 483 (M+1)$^+$ (2×$^{81}$Br)

Using the methods described for the preparation of examples 1 and 23 the following compound can be prepared (using 2-methoxy-4-isopropyl-benzoic acid in the appropriate step):

EXAMPLE 25

4,5-Dibromo-2-(4-isopropyl-2-methoxy-phenyl)-7-methoxy-1-(2-methoxy-ethyl)-1H-benzoimidazole

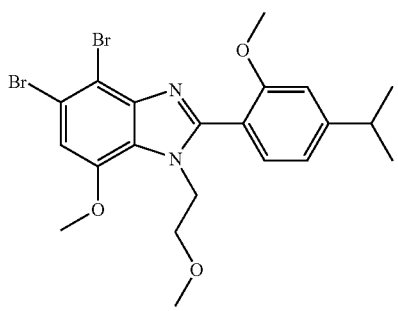

$R_t$=2.34 min (Waters Symmetry C8, 2.1×50 mm, detection 210-250 nM, 10% to 95% CH$_3$CN in H$_2$O in 2 min+0.05% TFA, flow rate 1.0 ml/min)

MS: 511 (M+1)$^+$ (2×$^{79}$Br), 513 (M+1)$^+$ ($^{79}$Br, $^{81}$Br), 515 (M+1)$^+$ (2×$^{81}$Br)

EXAMPLE 26

4-Iodo-5-bromo-2-(4-isopropyl-phenyl)-7-methoxy-1-(2-methoxy-ethyl)-1H-benzoimidazole

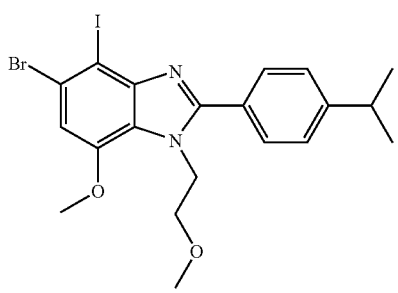

A solution of 100 mg (0.248 mmol) 5-bromo-2-(4-isopropyl-phenyl)-7-methoxy-1-(2-methoxy-ethyl)-1H-benzoimidazole and 61 mg (0.273 mmol) N-iodosuccinimide in 3 ml acetonitrile is refluxed for 12 h. The reaction mixture is cooled to room temperature and concentrated in vacuo. The residue is purified by flash-chromatography on silica gel (hexane:EtOAc=4:1) and recrystallisation from hexane/diethyl ether afforded 82 mg of the title compound as colorless crystals.

$R_t$=2.60 min (Waters Symmetry C8, 2.1×50 mm, detection 210-250 nM, 10% to 95% CH$_3$CN in H$_2$O in 2 min+0.05% TFA, flow rate 1.0 ml/min)

MS: 529 (M+1)$^+$ ($^{79}$Br), 531 (M+1)$^+$ ($^{81}$Br)

Using the methods described for the preparation of examples 1 and 26 the following compound can be prepared (using 2-methoxy-4-isopropyl-benzoic acid in the appropriate step):

EXAMPLE 27

5-Bromo-4-iodo-2-(4-isopropyl-2-methoxy-phenyl)-7-methoxy-1-(2-methoxy-ethyl)-1H-benzoimidazole

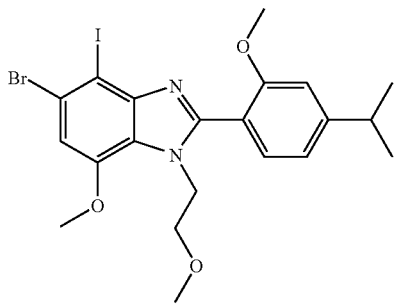

$R_t$=2.38 min (Waters Symmetry C8, 2.1×50 mm, detection 210-250 nM, 10% to 95% CH$_3$CN in H$_2$O in 2 min+0.05% TFA, flow rate 11.0 ml/min)

MS: 559 (M+1)$^+$ ($^{79}$Br), 561 (M+1)$^+$ ($^{81}$Br)

EXAMPLE 28

4-Bromo-2-(4-isopropyl-phenyl)-7-methoxy-1-(2-methoxy-ethyl)-5-trifluoromethyl-1H-benzoimidazole

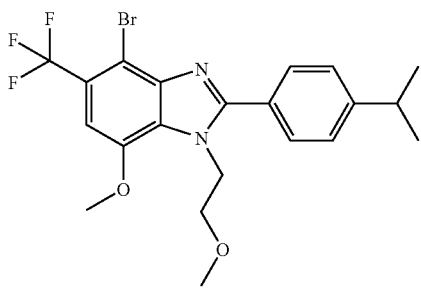

The title compound and the precursors can be prepared using the same synthesis sequence as described in example 1 and 23 from 5-trifluoromethyl-3-methoxy-benzene-1,2-diamine.

$R_t$=2.73 min (Waters Symmetry C8, 2.1×50 mm, detection 210-250 nM, 10% to 95% CH$_3$CN in H$_2$O in 2 min+0.05% TFA, flow rate 1.0 ml/min)

MS: 471 (M+1)$^+$ ($^{79}$Br), 473 (M+1)$^+$ ($^{81}$Br)

EXAMPLE 29

4-Bromo-1-cyclopropylmethyl-2-(4-isopropyl-phenyl)-7-methoxy-5-trifluoromethyl-1H-benzoimidazole

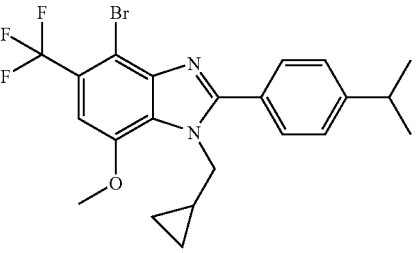

The title compound can be prepared using the same synthesis sequence as described in example 28 by using bromomethyl-cyclopropane instead of 1-bromo-2-methoxy-ethane.

$R_t$=2.79 min (Waters Symmetry C8, 2.1×50 mm, detection 210-250 nM, 10% to 95% CH$_3$CN in H$_2$O in 2 min+0.05% TFA, flow rate 11.0 ml/min)

MS: 467 (M+1)$^+$ ($^{79}$Br), 469 (M+1)$^+$ ($^{81}$Br)

a) 5-Trifluoro-3-methoxy-benzene-1,2-diamine can be prepared starting from 1-methoxy-3-nitro-5-trifluoromethyl-benzene using the same reaction sequence as described for the preparation of 3-bromo-6-methoxy-benzene-1,2-diamine as described in example 1 (steps c and d).

EXAMPLE 30

4-Bromo-5-iodo-2-(4-isopropyl-phenyl)-7-methoxy-1-(2-methoxy-ethyl)-1H-benzoimidazole

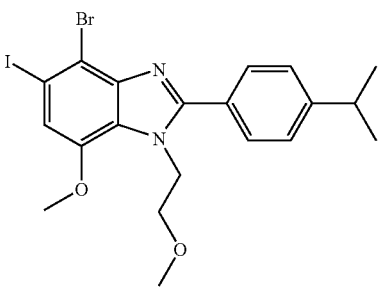

The title compound is prepared starting from 4-bromo-5-iodo-2-(4-isopropyl-phenyl)-7-methoxy-1H-benzoimidazole using the same reaction conditions as described for the preparation of example 1.

$R_t$=2.52 min (Waters Symmetry C8, 2.1×50 mm, detection 210-250 nM, 10% to 95% CH$_3$CN in H$_2$O in 2 min+0.05% TFA, flow rate 1.0 ml/min)

MS: 529 (M+1)$^+$ ($^{79}$Br), 531 (M+1)$^+$ ($^{81}$Br)

The starting material can be prepared as follows:

a) 4-Bromo-5-iodo-2-(4-isopropyl-phenyl)-7-methoxy-1H-benzoimidazole

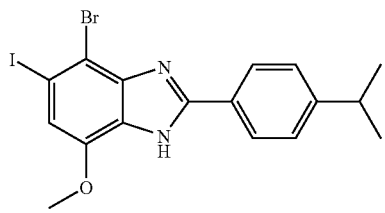

To a solution of 200 mg (0.51 mmol) 5-iodo-2-(4-isopropyl-phenyl)-7-methoxy-1H-benzoimidazole in 3 ml glacial acetic acid is slowly added 82 mg (0.51 mmol) bromine. The reaction mixture is stirred for 45 min. 30 ml EtOAc are added and this solution is washed 2n NaOH, water and brine, dried over MgSO$_4$, filtered and concentrated in vacuo. The residue is purified by flash-chromatography on silica gel (hexane:EtOAc=3:1) and recrystallized from EtOAc/diethyl ether to afford 126 mg of the title compound as off-white crystals.

b) 5-Iodo-2-(4-isopropyl-phenyl)-7-methoxy-1H-benzoimidazole is prepared starting from 4 iodo-2-methoxy-6-nitro-phenylamine using the same reaction sequence as described in examples 1 and 23.

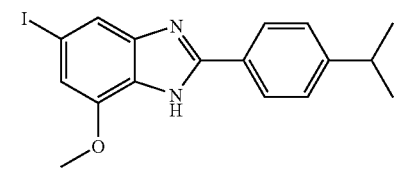

c) 4-Iodo-2-methoxy-6-nitro-phenylamine

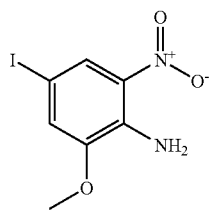

A mixture of 6.2 g (36.9 mmol) 2-methoxy-6-nitro-phenylamine, 9.4 g (37 mmol) iodine and 5.8 g (18.5 mmol) silver sulfate in 90 ml glacial acetic acid is stirred at 60° C. for 12 h. The reaction mixture is cooled to room temperature, poured on water and extracted (3×) with ethyl acetate. The combined organic layers are washed with water (2×) and brine, dried over MgSO$_4$, filtered and concentrated in vacuo. The residue is purified by flash-chromatography on silica gel (hexane:EtOAc=2:1) to afford 8.57 g of the title compound as bright red crystals.

EXAMPLE 31

5-Bromo-4-ethynyl-2-(4-isopropyl-phenyl)-7-methoxy-1-(2-methoxy-ethyl)-1H-benzoimidazole

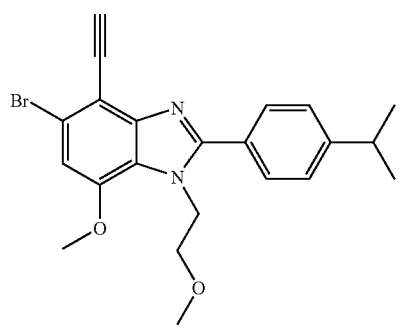

The title compound is prepared starting from 5-Bromo-2-(4-isopropyl-phenyl)-7-methoxy-1-(2-methoxy-ethyl)-1H-benzoimidazole using the same methodology as described for the preparation of example 11.

$R_t$=2.24 min (Waters Symmetry C8, 2.1×50 mm, detection 210-250 nM, 10% to 95% CH$_3$CN in H$_2$O in 2 min+0.05% TFA, flow rate 1.0 ml/min)

MS: 427 (M+1)$^+$ ($^{79}$Br), 429 (M+1)$^+$ ($^{81}$Br)

EXAMPLE 32

2-(4-Isopropyl-phenyl)-7-methoxy-1-(2-methoxy-ethyl)-1H-benzoimidazole-5-carbonitrile

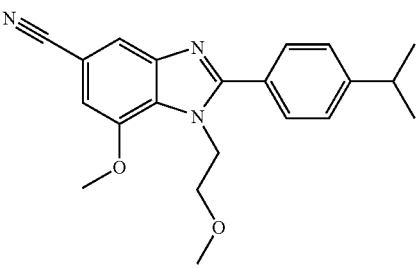

A mixture of 430 mg (1.07 mmol) 5-bromo-2-(4-isopropyl-phenyl)-7-methoxy-1-(2-methoxy-ethyl)-1H-benzoimidazole (example 22), 125 mg (1.07 mmol) zinc cyanide and 20 mg tetrakis(triphenylphosphine) palladium in 5 ml DMF is heated in a microwave oven for 75 min (180° C.). After that the reaction mixture is poured on water and extracted (3×) with ethyl acetate. The combined organic layers are washed with water (3×) and brine, dried over MgSO$_4$, filtered and concentrated in vacuo. The residue is purified by flash-chromatography on silica gel (hexane:EtOAc=3:1) to afford 250 mg of the title compound as a colorless solid.

EXAMPLE 33

4-Bromo-2-(4-isopropyl-phenyl)-7-methoxy-1-(2-methoxy-ethyl)-1H-benzoimidazole-5-carbonitrile

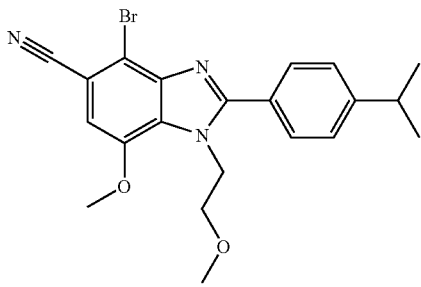

A mixture of 110 mg (0.315 mmol) 2-(4-isopropyl-phenyl)-7-methoxy-1-(2-methoxy-ethyl)-1H-benzoimidazole-5-carbonitrile and 56 mg (0.315 mmol) N-bromosuccinimide in 5 ml acetonitrile is stirred at reflux for 3 h. Then the solvents are evaporated and the residue is purified by flash-chromatography on silica gel (hexane:EtOAc=3:1) and recrystallized from EtOAc/diethyl ether/hexane to afford 60 mg of the title compound as colorless crystals.

$R_t$=2.59 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 428 (M+1)$^+$ ($^{79}$Br), 430 (M+1)$^+$ ($^{81}$Br)

EXAMPLE 34

4-Bromo-5-fluoro-2-(4-isopropyl-phenyl)-7-methoxy-1-(2-methoxy-ethyl)-1H-benzoimidazole

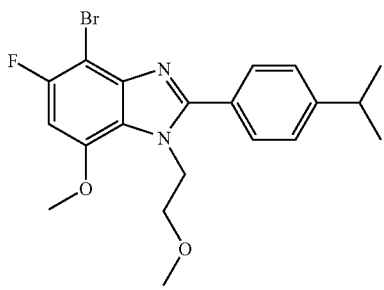

The title compound is prepared from 4-bromo-5-fluoro-2-(4-isopropyl-phenyl)-7-methoxy-1-(2-methoxy-ethyl)-1H-benzoimidazole using the method described in example 1

$R_t$=2.30 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 421 (M+1)$^+$ ($^{79}$Br), 423 (M+1)$^+$ ($^{81}$Br)

Preparation of the Starting Material 5-fluoro-2-(4-isopropyl-phenyl)-7-methoxy-1-(2-methoxy-ethyl)-1H-benzoimidazole

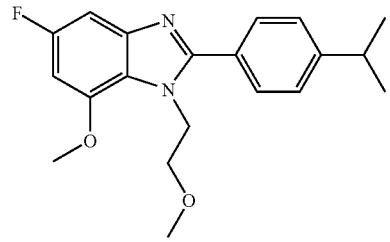

To a solution of 400 mg (0.98 mmol) 5-bromo-2-(4-isopropyl-phenyl)-7-methoxy-1-(2-methoxy-ethyl)-1H-benzoimidazole in 3 ml dry THF, n-BuLi (0.740 ml, 1.18 mmol) is added slowly at −78° C. After stirring for 45 min. at −78° C. N-fluoro-bis(phenylsulfonyl)amine (568.7 mg, 1.77 mmol) is added. Stirring at −78° C. is continued for another hour and then the reaction mixture is warmed to room temperature. After that the reaction mixture is poured on water and extracted (3×) with ethyl acetate. The combined organic layers are washed with water (3×) and brine, dried over $MgSO_4$, filtered and concentrated in vacuo. The residue is purified by flash-chromatography on silica gel (hexane:EtOAc=2:1–>1:1) to afford 40 mg of the title compound as a colorless oil.

EXAMPLE 35

5-Benzyl-4-bromo-2-(4-isopropyl-phenyl)-7-methoxy-1-(2-methoxy-ethyl)-1H-benzoimidazole

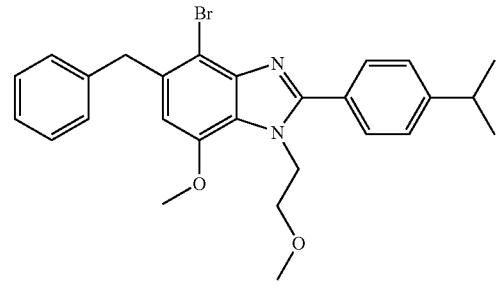

6 μl (0.122 mmol) bromine are added to a solution of 48 mg (0.116 mmol) 5-benzyl-2-(4-isopropyl-phenyl)-7-methoxy-1-(2-methoxy-ethyl)-1H-benzoimidazole in 6 ml glacial acetic acid. The reaction mixture is stirred at room temperature for 10 min. 25 ml EtOAc are added and this solution is washed 4N NaOH (2×), water and brine, dried over $MgSO_4$, filtered and concentrated in vacuo. The residue is recrystallized from dichloromethane/diethyl ether/hexane to afford 40 mg of the title compound as colorless crystals.

$R_t$=2.38 min (Waters Symmetry C8, 2.1×50 mm, detection 210-250 nM, 10% to 95% $CH_3CN$ in $H_2O$ in 2 min+0.05% TFA, flow rate 11.0 ml/min)
MS: 493 (M+1)$^+$ ($^{79}$Br), 495 (M+1)$^+$ ($^{81}$Br)

The starting materials can be prepared as follows:

a) 5-Benzyl-2-(4-isopropyl-phenyl)-7-methoxy-1-(2-methoxy-ethyl)-1H-benzoimidazole

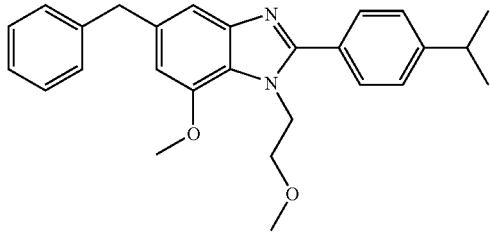

A solution of 150 mg (0.317 mmol) acetic acid[2-(4-isopropyl-phenyl)-7-methoxy-1-(2-methoxy-ethyl)-1H-benzoimidazol-5-yl]-phenyl-methyl ester in 8 ml THF:MeOH=1:2 is hydrogenated in the presence of 50 mg Pd/C (Engelhard 4505). Then the catalyst is filtered off and the filtrate is concentrated in vacuo to afford 120 mg of the title compound as a colorless oil.

b) Acetic acid[2-(4-isopropyl-phenyl)-7-methoxy-1-(2-methoxy-ethyl)-1H-benzoimidazol-5-yl]-phenyl-methyl Ester

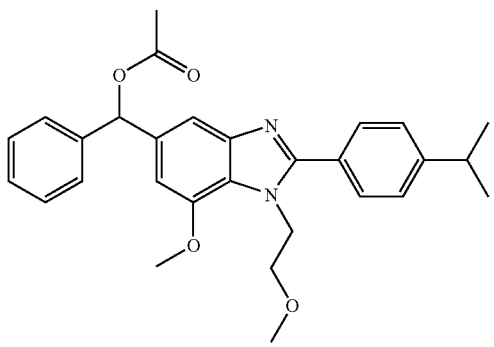

A solution of 136 mg (0.30 mmol) [2-(4-isopropyl-phenyl)-7-methoxy-1-(2-methoxy-ethyl)-1H-benzoimidazol-5-yl]-phenyl-methanol, 46 μl (0.66 mmol) acetyl chloride and 125 μl (0.90 mmol) triethylamine in 3 ml dichloromethane is stirred at room temperature for 1 h. The reaction mixture is poured on water and extracted (3×) with ethyl acetate. The combined organic layers are washed with water (2×) and brine, dried over MgSO$_4$, filtered and concentrated in vacuo. The residue is purified by flash-chromatography on silica gel (hexane:EtOAc=1:1) to afford 140 mg of the title compound as a colorless oil.

c) [2-(4-Isopropyl-phenyl)-7-methoxy-1-(2-methoxy-ethyl)-1H-benzoimidazol-5-yl]-phenyl-methanol

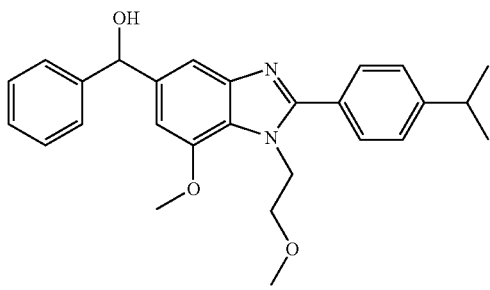

A solution of 150 mg (0.426 mmol) 2-(4-isopropyl-phenyl)-7-methoxy-1-(2-methoxy-ethyl)-1H-benzoimidazole-5-carbaldehyde in 2 ml THF is treated with excess phenylmagnesiumbromide (prepared from 112 μl bromobenzene and 26 mg magnesium in 5 ml diethyl ether). The resulting mixture is stirred at room temperature for 1 h. The reaction mixture is poured on water and extracted (3×) with ethyl acetate. The combined organic layers are washed with water (2×) and brine, dried over MgSO$_4$, filtered and concentrated in vacuo. The residue is purified by flash-chromatography on silica gel (hexane:EtOAc=1:2) to afford 136 mg of the title compound as a white solid.

d) 2-(4-Isopropyl-phenyl)-7-methoxy-1-(2-methoxy-ethyl)-1H-benzoimidazole-5-carbaldehyde

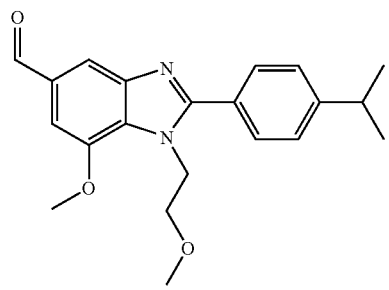

A mixture of 480 mg (1.37 mmol) 2-(4-isopropyl-phenyl)-7-methoxy-1-(2-methoxy-ethyl)-1H-benzoimidazole-5-carbonitrile (example 32), 15 mg Raney-Nickel (in water), 967 mg (11.0 mmol) sodium hypophosphite (in 10 ml water), 10 ml acetic acid and 20 ml pyridine is stirred for 6 h at 60° C. The catalyst is filtered off and the filtrate is poured on water and extracted (3×) with ethyl acetate. The combined organic layers are washed with water (2×) and brine, dried over MgSO$_4$, filtered and concentrated in vacuo. The residue is purified by flash-chromatography on silica gel (hexane:EtOAc=1:1) to afford 330 mg of the title compound as a white crystalline solid.

EXAMPLE 36

5-Benzyl-4-iodo-2-(4-isopropyl-phenyl)-7-methoxy-1-(2-methoxy-ethyl)-1H-benzoimidazole

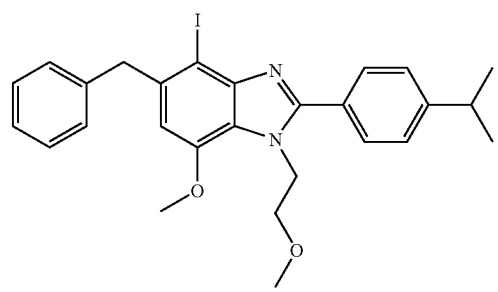

417 mg (1.78 mmol) N-iodo-succinimide are added to a solution of 670 mg (1.62 mmol) 5-benzyl-2-(4-isopropyl-phenyl)-7-methoxy-1-(2-methoxy-ethyl)-1H-benzoimidazole in 25 ml acetonitrile. The reaction mixture is stirred at reflux temperature for 3 h. The reaction mixture is poured on water and extracted (3×) with ethyl acetate. The combined organic layers are washed with water and brine, dried over MgSO₄, filtered and concentrated in vacuo. The residue is purified by flash-chromatography on silica gel (hexane:EtOAc=4:1) to afford 582 mg of the title compound as a white crystalline solid.

$R_t$=2.39 min (Waters Symmetry C8, 2.1×50 mm, detection 210-250 nM, 10% to 95% CH₃CN in H₂O in 2 min+0.05% TFA, flow rate 1.0 ml/min)
MS: 541 (M+1)⁺

EXAMPLE 37

5-Benzyl-4-ethynyl-2-(4-isopropyl-phenyl)-7-methoxy-1-(2-methoxy-ethyl)-1H-benzoimidazole

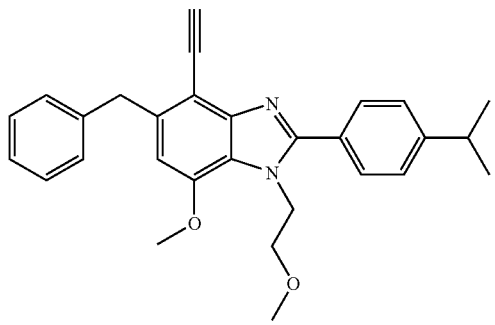

The title compound is prepared starting from 5-benzyl-4-iodo-2-(4-isopropyl-phenyl)-7-methoxy-1-(2-methoxy-ethyl)-1H-benzoimidazole using the same methodology as described for the preparation of example 11.

$R_t$=2.27 min (Waters Symmetry C8, 2.1×50 mm, detection 210-250 nM, 10% to 95% CH₃CN in H₂O in 2 min+0.05% TFA, flow rate 1.0 ml/min)
MS: 439 (M+1)⁺

EXAMPLE 38

4-Ethynyl-2-(4-isopropyl-phenyl)-7-methoxy-5-(2-methoxy-benzyl)-1-(2-methoxy-ethyl)-1H-benzoimidazole

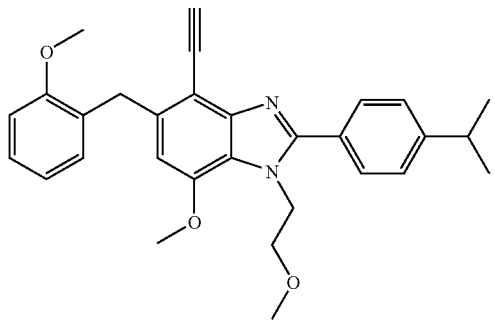

The title compound is prepared starting from 4-Iodo-2-(4-isopropyl-phenyl)-7-methoxy-5-(2-methoxy-benzyl)-1-(2-methoxy-ethyl)-1H-benzoimidazole using the same methodology as described for the preparation of example 11.

$R_t$=2.26 min (Waters Symmetry C8, 2.1×50 mm, detection 210-250 nM, 10% to 95% CH₃CN in H₂O in 2 min+0.05% TFA, flow rate 11.0 ml/min)
MS: 469 (M+1)⁺

EXAMPLE 39

4-Bromo-5-ethyl-2-(4-isopropyl-phenyl)-7-methoxy-1-(2-methoxy-ethyl)-1H-benzoimidazole

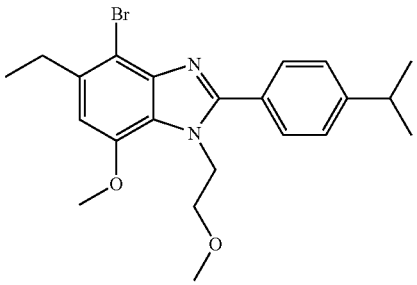

The title compound is prepared using the same methodology as described for the preparation of example 35. (Instead of phenylmagnesiumbromide, ethylmagnesiumbromide is used.)

$R_t$2.24 min (Waters Symmetry C8, 2.1×50 mm, detection 210-250 nM, 10% to 95% CH₃CN in H₂O in 2 min+0.05% TFA, flow rate 1.0 ml/min)
MS: 431 (M+1)⁺ (⁷⁹Br), 433 (M+1)⁺ (⁸¹Br)

EXAMPLE 40

4-Bromo-5-cyclobutylmethyl-2-(4-isopropyl-phenyl)-7-methoxy-1-(2-methoxy-ethyl)-1H-benzoimidazole

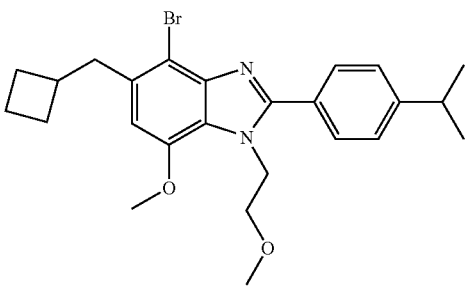

The title compound is prepared using the same methodology as described for the preparation of example 35. (Instead of phenylmagnesiumbromide, cyclobutyl-methylmagnesiumbromide is used.)

$R_t$=2.53 min (Waters Symmetry C8, 2.1×50 mm, detection 210-250 nM, 10% to 95% CH$_3$CN in H$_2$O in 2 min+0.05%-TFA, flow rate 1.0 ml/min)

MS: 471 (M+1)$^+$ ($^{79}$Br), 473 (M+1)$^+$ ($^{81}$Br)

EXAMPLE 41

4-Bromo-5-(3-fluoro-benzyl)-2-(4-isopropyl-phenyl)-7-methoxy-1-(2-methoxy-ethyl)-1H-benzoimidazole

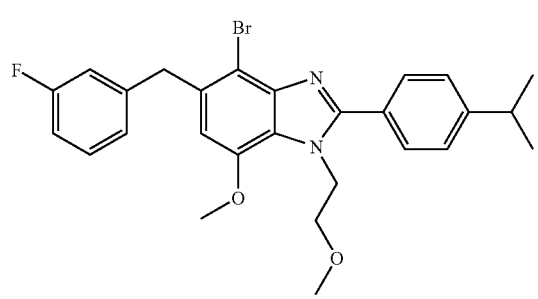

The title compound is prepared using the same methodology as described for the preparation of example 35. (Instead of phenylmagnesiumbromide, 3-fluoro-phenylmagnesiumbromide is used.)

$R_t$=2.43 min (Waters Symmetry C8, 2.1×50 mm, detection 210-250 nM, 10% to 95% CH$_3$CN in H$_2$O in 2 min+0.05% TFA, flow rate 1.0 ml/min)

MS: 511 (M+1)$^+$ ($^{79}$Br), 513 (M+1)$^+$ ($^{81}$Br)

EXAMPLE 42

4-Bromo-5-(3-chloro-benzyl)-2-(4-isopropyl-phenyl)-7-methoxy-1-(2-methoxy-ethyl)-1H-benzoimidazole

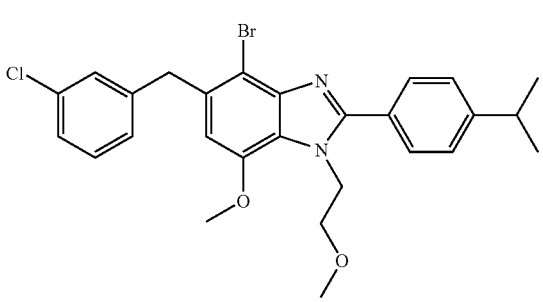

The title compound is prepared using the same methodology as described for the preparation of example 35. (Instead of phenylmagnesiumbromide, 3-chloro-phenylmagnesiumbromide is used.)

$R_t$=2.42 min (Waters Symmetry C8, 2.1×50 mm, detection 210-250 nM, 10% to 95% CH$_3$CN in H$_2$O in 2 min+0.05% TFA, flow rate 1.0 ml/min)

MS: 527 (M+1)$^+$ ($^{35}$Cl, $^{79}$Br), 529 (M+1)$^+$ ($^{35}$Cl, $^{81}$Br/$^{37}$Cl, $^{79}$Br) 531 (M+1)$^+$ ($^{37}$Cl, $^{81}$Br)

EXAMPLE 43

4-Bromo-2-(4-isopropyl-phenyl)-7-methoxy-1-(2-methoxy-ethyl)-5-thiazol-2-ylmethyl-1H-benzoimidazole

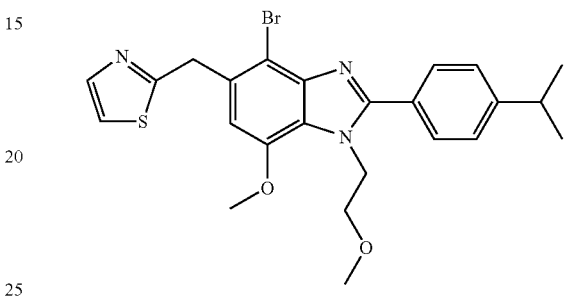

The title compound is prepared using the same methodology as described for the preparation of example 35. Instead of phenylmagnesiumbromide, 2-lithio-thiazole (prepared from 2-bromo-thiazole and n-BuLi) is used.

$R_t$=2.14 min (Waters Symmetry C8, 2.1×50 mm, detection 210-250 nM, 10% to 95% CH$_3$CN in H$_2$O in 2 min+0.05% TFA, flow rate 1.0 ml/min)

MS: 500 (M+1)$^+$ ($^{79}$Br), 502 (M+1)$^+$ ($^{81}$Br)

EXAMPLE 44

4-Bromo-5-(3,5-difluoro-benzyl)-2-(4-isopropyl-phenyl)-7-methoxy-1-(2-methoxy-ethyl)-1H-benzoimidazole

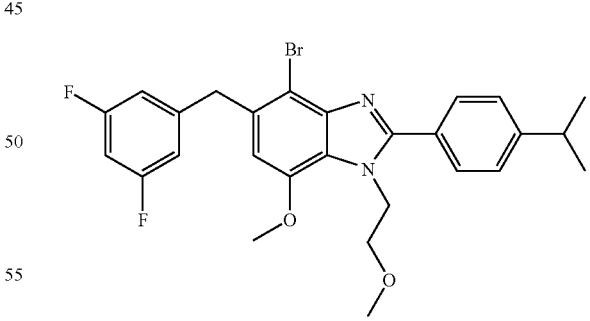

The title compound is prepared using the same methodology as described for the preparation of example 35. Instead of phenylmagnesiumbromide, 3,5-difluoro-phenylmagnesiumbromide is used.

$R_t$=2.40 min (Waters Symmetry C8, 2.1×50 mm, detection 210-250 nM, 10% to 95% CH$_3$CN in H$_2$O in 2 min+0.05% TFA, flow rate 1.0 ml/min)

MS: 529 (M+1)$^+$ ($^{79}$Br), 531 (M+1)$^+$ ($^{81}$Br)

EXAMPLE 45

4-Bromo-2-(4-isopropyl-phenyl)-7-methoxy-1-(2-methoxy-ethyl)-5-pyridin-3-ylmethyl-1H-benzoimidazole

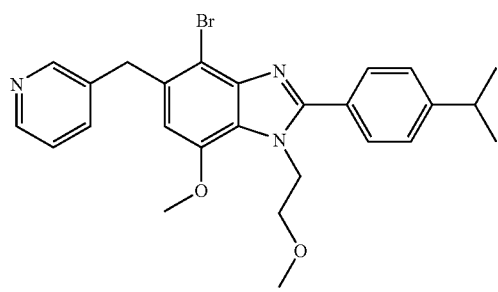

The title compound is prepared using the same methodology as described for the preparation of example 35. Instead of phenylmagnesiumbromide, 3-lithio-pyridine (prepared from 3-bromo-pyridine and n-BuLi) is used.

$R_t$=1.89 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 494 (M+1)$^+$ ($^{79}$Br), 496 (M+1)$^+$ ($^{81}$Br)

EXAMPLE 46

4-Bromo-2-(4-isopropyl-phenyl)-7-methoxy-1-(2-methoxy-ethyl)-5-(2-methylsulfanyl-benzyl)-1H-benzoimidazole

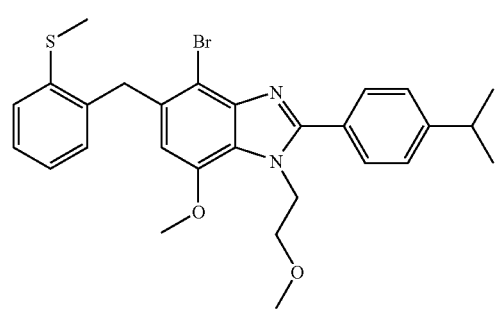

The title compound is prepared using the same methodology as described for the preparation of example 35.

$R_t$=2.388 min (Waters Symmetry C8, 2.1×50 mm, detection 210-250 nM, 10% to 95% $CH_3CN$ in $H_2O$ in 2 min+ 0.05% TFA, flow rate 1.0 ml/min)

MS: 539 (M+1)$^+$ ($^{79}$Br), 541 (M+1)$^+$ ($^{81}$Br)

The starting material can be prepared as follows:

a) 2-(4-Isopropyl-phenyl)-7-methoxy-1-(2-methoxy-ethyl)-5-(2-methylsulfanyl-benzyl)-1H-benzoimidazole

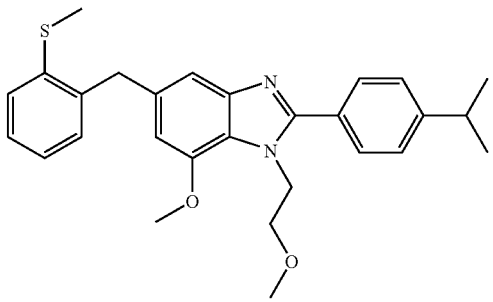

To a mixture of 797 mg (1.67 mmol) [2-(4-isopropyl-phenyl)-7-methoxy-1-(2-methoxy-ethyl)-1H-benzoimidazol-5-yl]-(2-methylsulfanyl-phenyl)-methanol, 436 mg iodine in 13 ml acetic acid (100%), 0.88 ml of phosphinic acid (ca. 5 equiv.) is added at room temperature. The mixture is heated to 60° C. and stirred for 1 h. After that the reaction mixture is allowed to cool to room temperature and 100 ml ethyl acetate is added. The combined organic layers are washed with 4N NaOH-solution (4×), water (2×) and brine, dried over $MgSO_4$, filtered and the filtrate is concentrated in vacuo to afford 914 mg of the title compound as a colorless oil.

b) [2-(4-Isopropyl-phenyl)-7-methoxy-1-(2-methoxy-ethyl)-1H-benzoimidazol-5-yl]-(2-methylsulfanyl-phenyl)-methanol

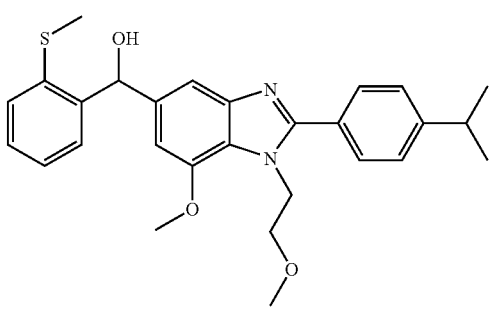

The title compound is prepared using the same methodology as described for the preparation of example 35 (step c). Instead of phenylmagnesiumbromide, 1-bromo-magnesium2-methylsulfanyl-benzene (prepared from 1-bromo-2-methylsulfanyl-benzene and magnesium) is used.

EXAMPLE 47

4-Bromo-2-(4-isopropyl-phenyl)-5-(2-methanesulfinyl-benzyl)-7-methoxy-1-(2-methoxy-ethyl)-1H-benzoimidazole

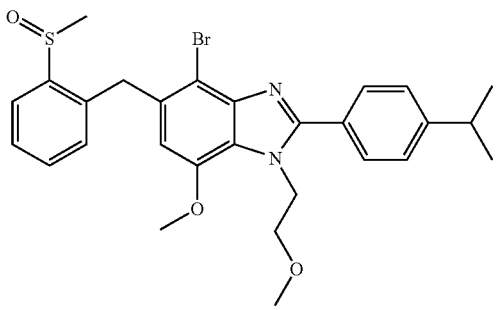

53 µl (0.122 mmol) bromine are added to a solution of 496 mg (1.03 mmol) 2-(4-isopropyl-phenyl)-5-(2-methanesulfinyl-benzyl)-7-methoxy-1-(2-methoxy-ethyl)-1H-benzoimidazole in 22 ml glacial acetic acid. The reaction mixture is stirred at room temperature for 10 min. Then 25 ml EtOAc are added and this solution is washed with 4N NaOH (2×), water and brine, dried over MgSO$_4$, filtered and concentrated in vacuo. The residue is purified by flash-chromatography on silica gel (hexane:EtOAc=1:4) to afford 340 mg of the title compound as colorless crystals.

R$_t$=2.12 min (Waters Symmetry C8, 2.1×50 mm, detection 210-250 nM, 10% to 95% CH$_3$CN in H$_2$O in 2 min+0.05% TFA, flow rate 1.0 ml/min)

MS: 555 (M+1)$^+$ ($^{79}$Br), 557 (M+1)$^+$ ($^{81}$Br)

The starting material can be prepared as follows:

a): 2-(4-isopropyl-phenyl)-5-(2-methanesulfinyl-benzyl)-7-methoxy-1-(2-methoxy-ethyl)-1H-benzoimidazole

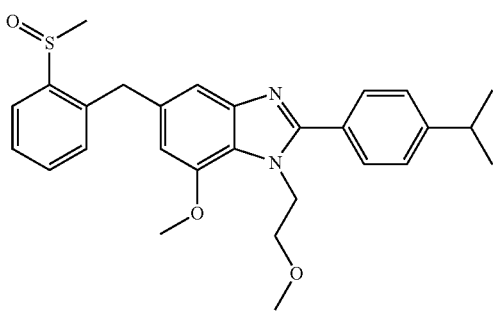

A mixture of 714 mg (1.32 mmol) of 2-(4-Isopropyl-phenyl)-7-methoxy-1-(2-methoxy-ethyl)-5-(2-methylsulfanyl-benzyl)-1H-benzoimidazole and 142 µl (1.39 mmol) hydrogen peroxide solution (30%) in 13 ml acetic acid is stirred at room temperature for 1.5 h. After that 25 ml EtOAc are added and this solution is washed with 4n NaOH (2×), water and sodiumhydrogensulfite solution, dried over MgSO$_4$, filtered and concentrated in vacuo. The residue is purified by flash-chromatography on silica gel (EtOAc) to afford 496 mg of the title compound as colorless crystals.

EXAMPLE 48

4-Bromo-2-(4-isopropyl-phenyl)-5-(2-methanesulfonyl-benzyl)-7-methoxy-1-(2-methoxy-ethyl)-1H-benzoimidazole

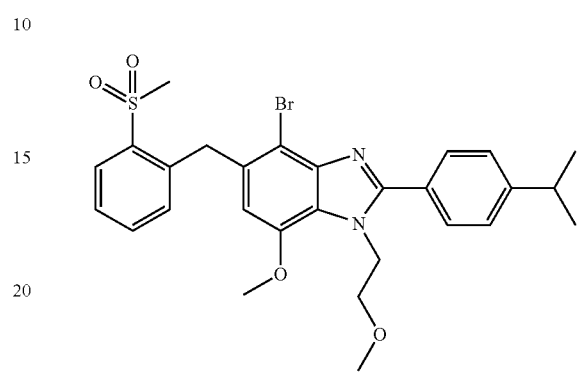

A mixture of 140 mg (0.252 mmol) of 4-Bromo-2-(4-isopropyl-phenyl)-5-(2-methanesulfinyl-benzyl)-7-methoxy-1-(2-methoxy-ethyl)-1H-benzoimidazole and 30 µl (0.265 mmol) hydrogen peroxide solution (30%) in 3 ml acetic acid is stirred at reflux temperature for 3 h. After that the reaction mixture is allowed to cool to room temperature and 25 ml EtOAc are added and this solution is washed with 4n NaOH (2×), water and sodiumhydrogensulfite solution, dried over MgSO$_4$, filtered and concentrated in vacuo. The residue is purified by flash-chromatography on silica gel (hexane:EtOAc=1:1) to afford 112 mg of the title compound as pale red crystals.

R$_t$=2.23 min (Waters Symmetry C8, 2.1×50 mm, detection 210-250 nM, 10% to 95% CH$_3$CN in H$_2$O in 2 min+0.05% TFA, flow rate 1.0 ml/min)

MS: 571 (M+1)$^+$ ($^{79}$Br), 573 (M+1)$^+$ ($^{81}$Br)

EXAMPLE 49

4-Bromo-2-(4-isopropyl-phenyl)-7-methoxy-1-(2-methoxy-ethyl)-5-pyridin-2-ylmethyl-1H-benzoimidazole

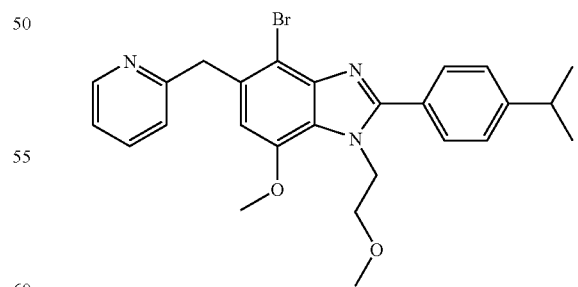

The title compound is prepared using the same methodology as described for the preparation of example 35.

R$_t$=1.90 min (Waters Symmetry C8, 2.1×50 mm, detection 210-250 nM, 10% to 95% CH$_3$CN in H$_2$O in 2 min+0.05% TFA, flow rate 1.0 ml/min)

MS: 494 (M+1)$^+$ ($^{79}$Br), 496 (M+1)$^+$ ($^{81}$Br)

The starting material can be prepared as follows:

a) 2-(4-Isopropyl-phenyl)-7-methoxy-1-(2-methoxy-ethyl)-5-pyridin-2-ylmethyl-1H-benzoimidazole

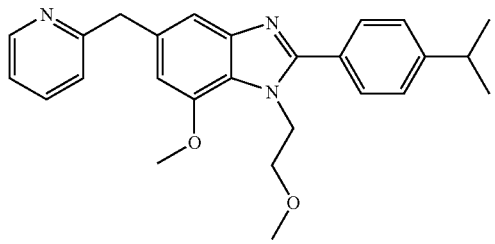

To a solution of ca. 250 mg of methanesulfonic acid [2-(4-isopropyl-phenyl)-7-methoxy-1-(2-methoxy-ethyl)-1H-benzoimidazol-5-yl]-pyridin-2-yl-methyl ester in 7 ml THF, 50 mg LiAlH$_4$ are added. The mixture is heated to reflux temperature and stirred for 3 h. After that the reaction mixture is allowed to cool to room temperature and 1N NaOH solution is added and this mixture is stirred for 30 min and filtered. The filtrate is extracted with ethyl acetate (3×). The combined organic layers are washed with water (2×) and brine, dried over MgSO$_4$, filtered and the filtrate is concentrated in vacuo. The residue is purified by flash-chromatography on silica gel (CH$_2$Cl$_2$:MeOH=95:5) to afford 40 mg of the title compound as an oil.

b) Methanesulfonic acid[2-(4-isopropyl-phenyl)-7-methoxy-1-(2-methoxy-ethyl)-1H-benzoimidazol-5-yl]-pyridin-2-yl-methyl Ester

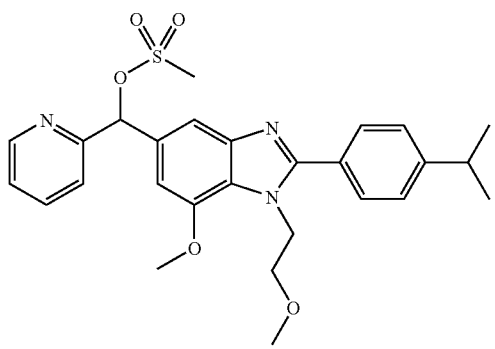

A mixture of 330 mg (0.76 mmol) [2-(4-isopropyl-phenyl)-7-methoxy-1-(2-methoxy-ethyl)-1H-benzoimidazol-5-yl]-pyridin-2-yl-methanol, 0.6 ml ethyl-diisopropyl-amine and 0.25 ml methanesulfonyl chloride is stirred at 0° C. for 1 h. Then the reaction mixture is poured on water and extracted (3×) with ethyl acetate. The combined organic layers are washed with water and brine, dried over MgSO$_4$, filtered and concentrated in vacuo to afford the title product as an oil that is used directly in the next step.

c) [2-(4-Isopropyl-phenyl)-7-methoxy-1-(2-methoxy-ethyl)-1H-benzoimidazol-5-yl]-pyridin-2-yl-methanol

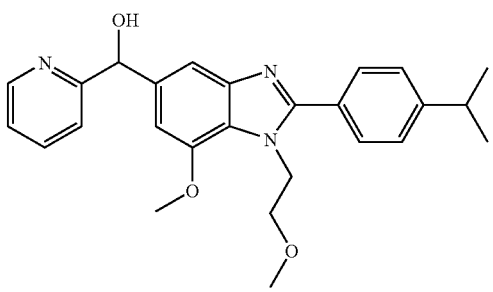

The title compound is prepared using the same methodology as described for the preparation of example 35 (step c). Instead of phenylmagnesiumbromide, 2-lithio-pyridine (prepared from 2-bromo-pyridine and n-BuLi) is used.

EXAMPLE 50

4-Iodo-2-(4-isopropyl-phenyl)-7-methoxy-5-(2-methoxy-benzyl)-1-(2-methoxy-ethyl)-1H-benzoimidazole

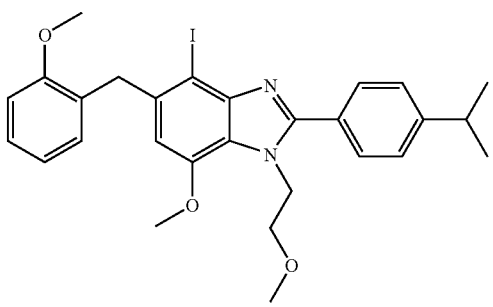

The title compound is prepared starting from [4-iodo-2-(4-isopropyl-phenyl)-7-methoxy-1-(2-methoxy-ethyl)-1H-benzoimidazol-5-yl]-(2-methoxy-phenyl)-methanol using the same methodology as described for the preparation of example 46 (step a).

R$_t$=2.37 min (Waters Symmetry C8, 2.1×50 mm, detection 210-250 nM, 10% to 95% CH$_3$CN in H$_2$O in 2 min+0.05% TFA, flow rate 1.0 ml/min)

MS: 571 (M+1)$^+$

The starting material can be prepared as follows:

[4-Iodo-2-(4-isopropyl-phenyl)-7-methoxy-1-(2-methoxy-ethyl)-1H-benzoimidazol-5-yl]-(2-methoxy-phenyl)-methanol

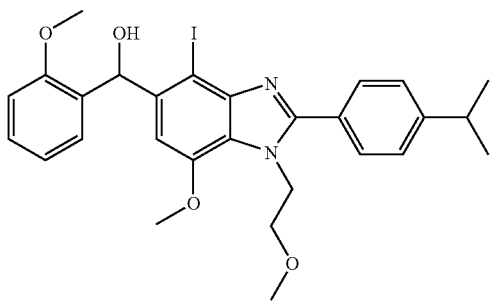

The title compound is prepared from 4-iodo-2-(4-isopropyl-phenyl)-7-methoxy-1-(2-methoxy-ethyl)-1H-benzoimidazole-5-carbaldehyde and 2-methoxyphenyl-magnesium bromide as described in example 35.

4-Iodo-2-(4-isopropyl-phenyl)-7-methoxy-1-(2-methoxy-ethyl)-1H-benzoimidazole-5-carbaldehyde

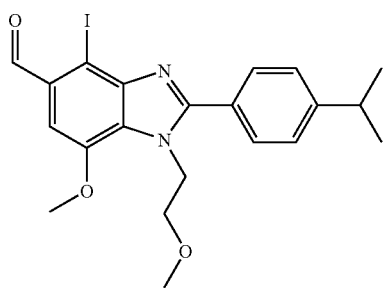

The title compound is prepared from 2-(4-isopropyl-phenyl)-7-methoxy-1-(2-methoxy-ethyl)-1H-benzoimidazole-5-carbaldehyde (preparation see example 35) as described in example 59.

EXAMPLE 51

4-Bromo-2-(4-isopropyl-phenyl)-7-methoxy-5-(2-methoxy-benzyl)-1-(2-methoxy-ethyl)-1H-benzoimidazole

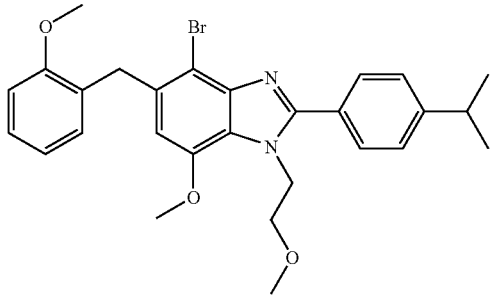

The title compound is prepared starting from [4-bromo-2-(4-isopropyl-phenyl)-7-methoxy-1-(2-methoxy-ethyl)-1H-benzoimidazol-5-yl]-(2-methoxy-phenyl)-methanol using the same methodology as described for the preparation of example 46 (step a).

$R_t$=2.35 min (Waters Symmetry C8, 2.1×50 mm, detection 210-250 nM, 10% to 95% CH$_3$CN in H$_2$O in 2 min+0.05% TFA, flow rate 1.0 ml/min)

MS: 523 (M+1)$^+$ ($^{79}$Br), 525 (M+1)$^+$ ($^{81}$Br)

The starting material can be prepared as follows:

[4-Bromo-2-(4-isopropyl-phenyl)-7-methoxy-1-(2-methoxy-ethyl)-1H-benzoimidazol-5-yl]-(2-methoxy-phenyl)-methanol

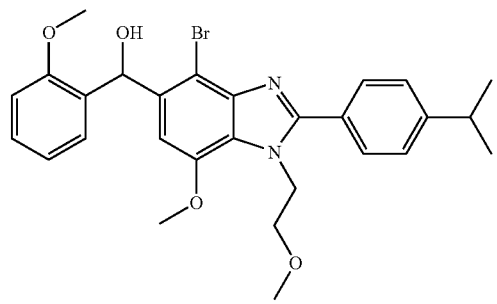

The title compound is prepared from 4-bromo-2-(4-isopropyl-phenyl)-7-methoxy-1-(2-methoxy-ethyl)-1H-benzoimidazole-5-carbaldehyde (see example 41, step c) and 2-methoxyphenyl-magnesium bromide as described in example 35.

EXAMPLE 52

4-Bromo-5-(3,4-dimethoxy-benzyl)-2-(4-isopropyl-phenyl)-7-methoxy-1-(2-methoxy-ethyl)-1H-benzoimidazole

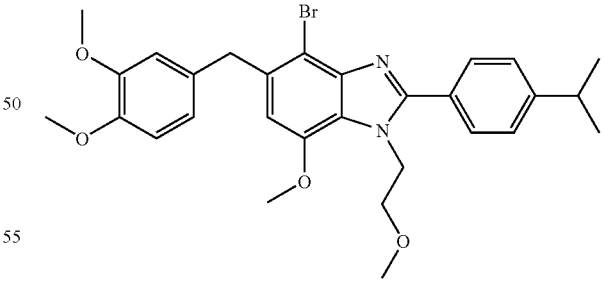

The title compound is prepared using the same methodology as described for the preparation of example 35. Instead of phenylmagnesiumbromide, 3,4-dimethoxyphenyl-magnesium-bromide is used.

$R_t$=2.26 min (Waters Symmetry C8, 2.1×50 mm, detection 210-250 nM, 10% to 95% CH$_3$CN in H$_2$O in 2 min+0.05% TFA, flow rate 1.0 ml/min)

MS: 553 (M+1)$^+$ ($^{79}$Br), 555 (M+1)$^+$ ($^{81}$Br)

EXAMPLE 53

4-Bromo-2-(4-isopropyl-phenyl)-7-methoxy-1-(2-methoxy-ethyl)-5-(3-methoxy-pyridin-2-ylmethyl)-1H-benzoimidazole

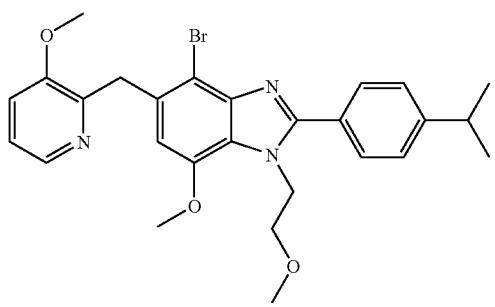

The title compound is prepared using the same methodology as described for the preparation of example 35. Instead of phenylmagnesiumbromide, 2-lithium-3-methoxy-pyridine is used.

$R_t$=1.94 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 524 (M+1)$^+$ ($^{79}$Br), 526 (M+1)$^+$ ($^{81}$Br)

EXAMPLE 54

5-Benzyl-4-ethyl-2-(4-isopropyl-phenyl)-7-methoxy-1-(2-methoxy-ethyl)-1H-benzoimidazole

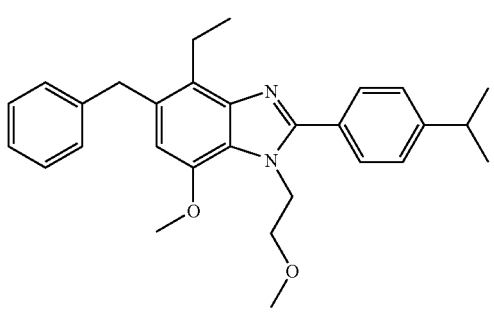

A solution of 58 mg (0.13 mmol) 5-benzyl-2-(4-isopropyl-phenyl)-7-methoxy-1-(2-methoxy-ethyl)-4-vinyl-1H-benzoimidazole in 5 ml methanol is hydrogenated in the presence of 10 mg Raney-Nickel (B113W Degussa) at normal pressure for 25 h. The catalyst is filtered off and the filtrate is concentrated in vacuo. The residue is purified by flash-chromatography on silica gel (hexane:EtOAc=6:1) to afford 26 mg of the title compound as a white crystalline solid.

$R_t$=2.29 in (Waters Symmetry C8, 2.1×50 mm, detection 210-250 nM, 10% to 95% $CH_3CN$ in $H_2O$ in 2 min+0.05% TFA, flow rate 1.0 ml/min)

MS: 443 (M+1)$^+$

The starting material can be prepared as follows:

5-Benzyl-2-(4-isopropyl-phenyl)-7-methoxy-1-(2-methoxy-ethyl)-4-vinyl-1H-benzoimidazole

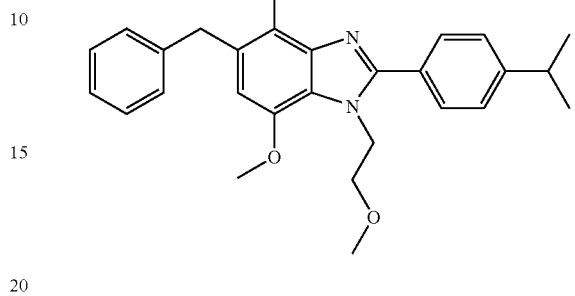

A mixture of 300 mg (0.556 mmol) 5-benzyl-4-iodo-2-(4-isopropyl-phenyl)-7-methoxy-1-(2-methoxy-ethyl)-1H-benzoimidazole, 40 mg bis(triphenylphosphine) palladium (II) dichloride and 0.2 ml tributyl(vinyl)stannane in 3 ml THF is stirred at reflux temperature for 24 h. The reaction mixture is concentrated in vacuo and the residue is purified by flash-chromatography on silica gel (hexane:EtOAc=6:1) to afford 278 mg of the title compound as a yellow crystalline solid.

EXAMPLE 55

4-Bromo-2-(4-isopropyl-phenyl)-7-methoxy-5-(3-methoxy-benzyl)-1-(2-methoxy-ethyl)-1H-benzoimidazole

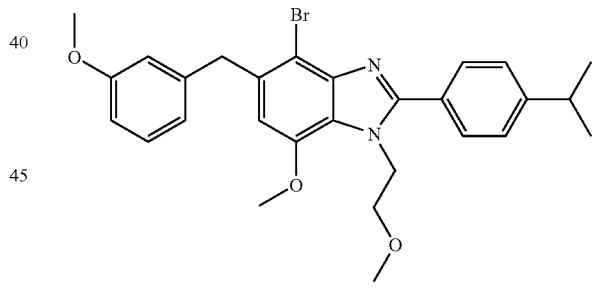

A mixture of 125 mg (0.233 mmol) [4-bromo-2-(4-isopropyl-phenyl)-7-methoxy-1-(2-methoxy-ethyl)-1H-benzoimidazol-5-yl]-(3-methoxy-phenyl)-methanone (example 26o), 45 mg KOH pellets, 3.2 ml hydrazine-monohydrate, 0.5 ml water and 13 ml ethyleneglykol is stirred at 190° C. for 2 h. After that the reaction mixture is poured on 4N HCl-solution and extracted (3×) with ethyl acetate. The combined organic layers are washed with water (2×) and brine, dried over $MgSO_4$, filtered and concentrated in vacuo. The residue is purified by flash-chromatography on silica gel (hexane:EtOAc=3:1) to afford 20 mg of the title compound as an off-white crystalline solid.

$R_t$=2.33 in (Waters Symmetry C8, 2.1×50 mm, detection 210-250 nM, 10% to 95% $CH_3CN$ in $H_2O$ in 2 min+0.05% TFA, flow rate 1.0 ml/min)

MS: 523 (M+1)$^+$ ($^{79}$Br), 525 (M+1)$^+$ ($^{81}$Br)

EXAMPLE 56

[4-Bromo-2-(4-isopropyl-phenyl)-7-methoxy-1-(2-methoxy-ethyl)-1H-benzoimidazol-5-yl]-(3-methoxy-phenyl)-methanone

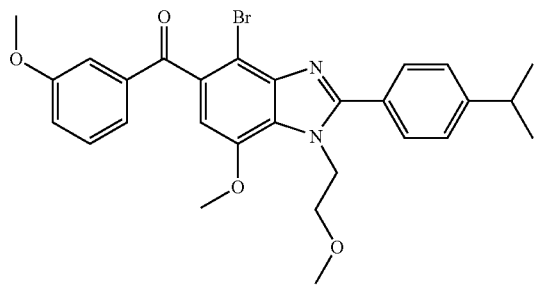

To a solution of 0.16 ml oxalylchloride in 4 ml dichloromethane, 0.27 ml DMSO (in 0.8 ml dichloromethane is slowly added at −60° C. This mixture is stirred under argon at −60° C. for 0.5 h. Then 250 mg (0.463 mmol) [4-Bromo-2-(4-isopropyl-phenyl)-7-methoxy-1-(2-methoxy-ethyl)-1H-benzoimidazol-5-yl]-(3-methoxy-phenyl)-methanol (in 2 ml dichloromethane) are added and stirring is continued at −60° C. for 1 h. 1 ml triethylamine is added and the reaction mixture is allowed to warm to room temperature, poured on water and extracted (3×) with dichloromethane. The combined organic layers are washed with water (2×) and brine, dried over MgSO$_4$, filtered and concentrated in vacuo. The residue is purified by flash-chromatography on silica gel (hexane:EtOAc=2:1) to afford 179 mg of the title compound as a colorless oil.

$R_t$=2.47 in (Waters Symmetry C8, 2.1×50 mm, detection 210-250 nM, 10% to 95% CH$_3$CN in H$_2$O in 2 min+0.05% TFA, flow rate 1.0 ml/min)

MS: 537 (M+1)$^+$ ($^{79}$Br), 539 (M+1)$^+$ ($^{81}$Br)

The starting material can be prepared as follows:

[4-Bromo-2-(4-isopropyl-phenyl)-7-methoxy-1-(2-methoxy-ethyl)-1H-benzoimidazol-5-yl]-(3-methoxy-phenyl)-methanol

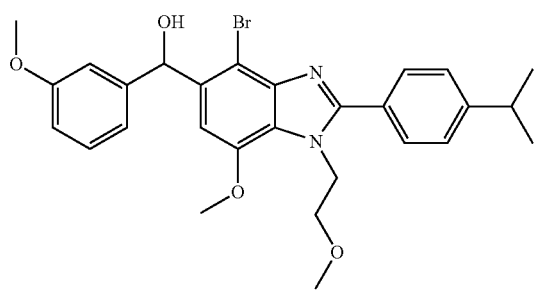

The title compound is prepared from 4-bromo-2-(4-isopropyl-phenyl)-7-methoxy-1-(2-methoxy-ethyl)-1H-benzoimidazole-5-carbaldehyde and 3-methoxyphenyl-magnesium bromide as described in examples 35 and 51.

EXAMPLE 57

[4-Bromo-2-(4-isopropyl-phenyl)-7-methoxy-1-(2-methoxy-ethyl)-1H-benzoimidazol-5-yl]-(2-methoxy-phenyl)-methanone

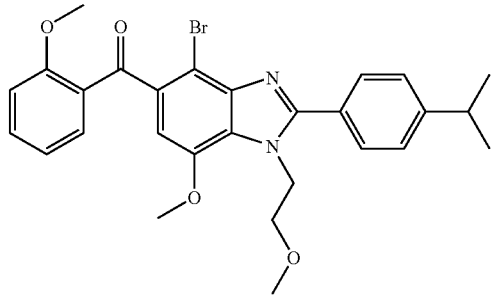

The title compound can be prepared as described in example 56, using 2-methoxyphenyl magnesium bromide instead of 3-methoxy-phenylmagnesium bromide.

$R_t$=2.37 in (Waters Symmetry C8, 2.1×50 mm, detection 210-250 nM, 10% to 95% CH$_3$CN in H$_2$O in 2 min+0.05% TFA, flow rate 1.0 ml/min)

MS: 537 (M+1)$^+$ ($^{79}$Br), 539 (M+1)$^+$ ($^{81}$Br)

EXAMPLE 58

4-Bromo-2-(4-isopropyl-phenyl)-7-methoxy-1-(2-methoxy-ethyl)-5-(1-phenyl-ethyl)-1H-benzoimidazole

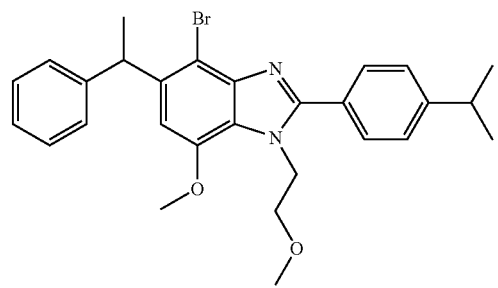

The title compound is prepared from 2-(4-isopropyl-phenyl)-7-methoxy-1-(2-methoxy-ethyl)-5-(1-phenyl-ethyl)-1H-benzoimidazole using the methodology described in example 35.

$R_t$=2.39 min (Waters Symmetry C8, 2.1×50 mm, detection 210-250 nM, 10% to 95% CH$_3$CN in H$_2$O in 2 min+0.05% TFA, flow rate 1.0 ml/min)

MS: 507 (M+1)$^+$ ($^{79}$Br), 509 (M+1)$^+$ ($^{81}$Br)

The starting materials can be prepared as follows:

a) 2-(4-Isopropyl-phenyl)-7-methoxy-1-(2-methoxy-ethyl)-5-(1-phenyl-ethyl)-1H-benzoimidazole

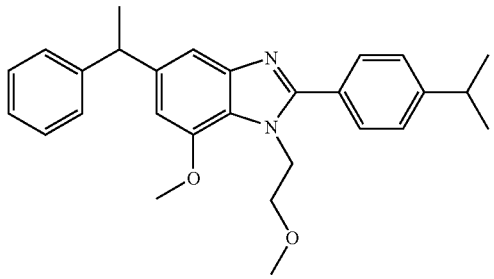

The title compound is prepared from 1-[2-(4-isopropyl-phenyl)-7-methoxy-1-(2-methoxy-ethyl)-1H-benzoimidazol-5-yl]-1-phenyl-ethanol using the methodology described in example 46 (step a).

b) 1-[2-(4-Isopropyl-phenyl)-7-methoxy-1-(2-methoxy-ethyl)-1H-benzoimidazol-5-yl]-1-phenyl-ethanol

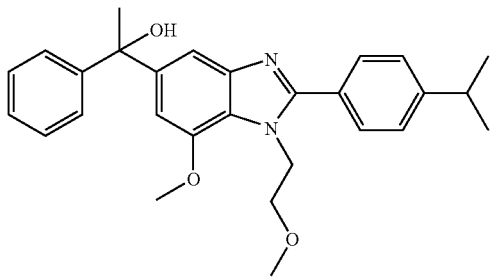

A solution of 163 mg (0.445 mmol) 1-[2-(4-isopropyl-phenyl)-7-methoxy-1-(2-methoxy-ethyl)-1H-benzoimidazol-5-yl]-ethanone in 2 ml THF is treated with excess phenylmagnesiumbromide (prepared from 112 µl bromobenzene and 26 mg magnesium in 5 ml diethyl ether). The resulting mixture is stirred at room temperature for 1 h. The reaction mixture is poured on water and extracted (3×) with ethyl acetate. The combined organic layers are washed with water (2×) and brine, dried over MgSO₄, filtered and concentrated in vacuo. The residue is purified by flash-chromatography on silica gel (hexane:EtOAc=2:1) to afford 109 mg of the title compound as an oil.

c) 1-[2-(4-Isopropyl-phenyl)-7-methoxy-1-(2-methoxy-ethyl)-1H-benzoimidazol-5-yl]-ethanone

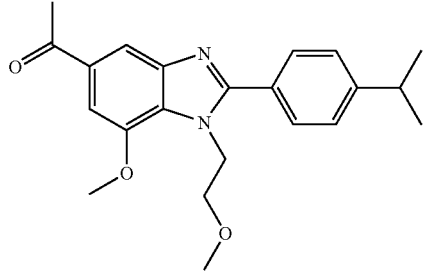

To a solution of 0.17 ml oxalylchloride in 4 ml dichloromethane, 0.285 ml DMSO (in 0.8 ml dichloromethane is slowly added at −60° C. This mixture is stirred under argon at −60° C. for 0.5 h. Then 180 mg (0.488 mmol) 1-[2-(4-isopropyl-phenyl)-7-methoxy-1-(2-methoxy-ethyl)-1H-benzoimidazol-5-yl]-ethanol (in 2 ml dichloromethane) are added and stirring is continued at −60° C. for 1 h. 1 ml triethylamine is added and the reaction mixture is allowed to warm to room temperature, poured on water and extracted (3×) with dichloromethane. The combined organic layers are washed with water (2×) and brine, dried over MgSO₄, filtered and concentrated in vacuo. The residue is purified by flash-chromatography on silica gel (hexane:EtOAc=3:1) to afford 163 mg of the title compound as a colorless oil.

d) 1-[2-(4-Isopropyl-phenyl)-7-methoxy-1-(2-methoxy-ethyl)-1H-benzoimidazol-5-yl]-ethanol

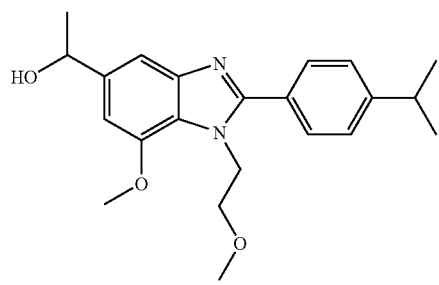

A solution of 150 mg (0.426 mmol) 2-(4-isopropyl-phenyl)-7-methoxy-1-(2-methoxy-ethyl)-1H-benzoimidazole-5-carbaldehyde in 2 ml THF is treated with excess methylmagnesiumiodide (prepared from 207 mg methyliodide and 35 mg magnesium in 5 ml diethyl ether). The resulting mixture is stirred at room temperature for 1 h. The reaction mixture is poured on water and extracted (3×) with ethyl acetate. The combined organic layers are washed with water (2×) and brine, dried over MgSO₄, filtered and concentrated in vacuo to afford 180 mg of the title compound as an oil.

EXAMPLE 59

4-Iodo-2-(4-isopropyl-phenyl)-7-methoxy-1-(2-methoxy-ethyl)-1H-benzoimidazole-5-carbonitrile

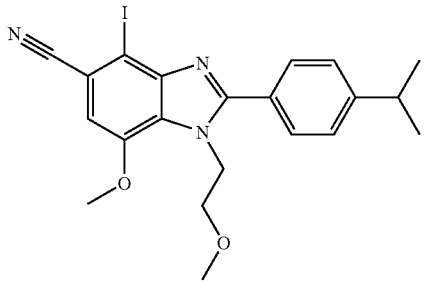

A mixture of 50 mg (0.143 mmol) 2-(4-isopropyl-phenyl)-7-methoxy-1-(2-methoxy-ethyl)-1H-benzoimidazole-5-carbonitrile and 36 mg (0.143 mmol) iodine and 22 mg (0.072 mmol) silver sulfate in 1 ml acetic acid is stirred at reflux for 3 h. Then the filtrate is poured on 2N NaOH and extracted (3×) with ethyl acetate. The combined organic layers are washed with water (2×) and brine, dried over MgSO₄, filtered and concentrated in vacuo. The residue is purified by flash-chromatography on silica gel (hexane:EtOAc=3:1) to afford 10 mg of the title compound as a white crystalline solid.

$R_t$=2.64 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 476 (M+1)$^+$

EXAMPLE 60

2-(4-Isopropyl-phenyl)-7-methoxy-1-(2-methoxy-ethyl)-1H-benzoimidazole-4-carbonitrile

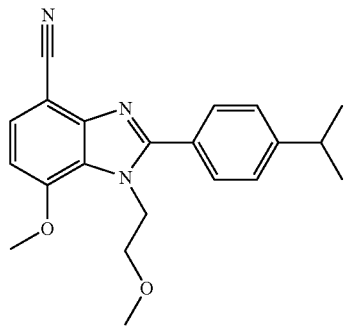

The title compound is prepared from 4-bromo-2-(4-isopropyl-phenyl)-7-methoxy-1-(2-methoxy-ethyl)-1H-benzoimidazole (example 1) using the same methodology as described for the preparation of example 32.

$R_t$=2.42 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 350 (M+1)$^+$

Starting from 2-(4-isopropyl-phenyl)-7-methoxy-1-(2-methoxy-ethyl)-1H-benzoimidazole-4-carbonitrile (example 60) the following compounds can be prepared using the same reaction sequence as described for the preparation of example 35:

EXAMPLE 61

4-Isobutyl-2-(4-isopropyl-phenyl)-7-methoxy-1-(2-methoxy-ethyl)-1H-benzoimidazole

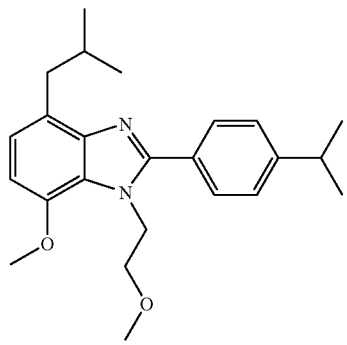

$R_t$=2.16 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 381 (M+1)$^+$

EXAMPLE 62

4-Benzyl-2-(4-isopropyl-phenyl)-7-methoxy-1-(2-methoxy-ethyl)-1H-benzoimidazole

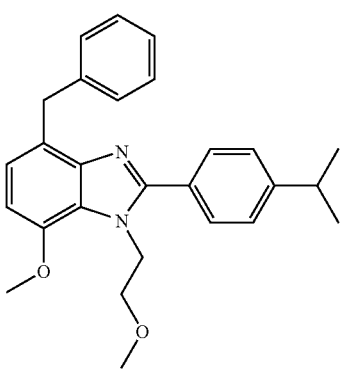

$R_t$=2.23 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 415 (M+1)$^+$

EXAMPLE 63

4,7-Dibromo-2-(4-isopropyl-phenyl)-1-(2-methoxy-ethyl)-1H-benzoimidazole

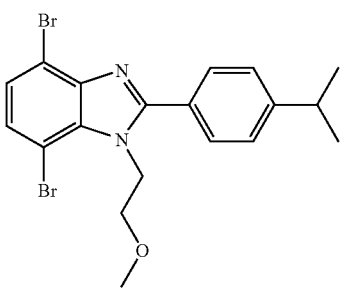

$R_t$=2.73 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 451 (M+1)$^+$ (2×$^{79}$Br), 453 (M+1)$^+$ ($^{79}$Br, $^{81}$Br), 455 (M+1)$^+$ (2×$^{81}$Br)

The title compound and the precursors are prepared from 3,6-Dibromo-benzene-1,2-diamine [Naef, R.; Balli, H. *Hel-* vetica Chimica Acta 1978, 61(8), 2958-73] using the same methodology as described for the preparation of example 1.

EXAMPLE 64

4,7-Dibromo-2-(4-isopropyl-phenyl)-1-(2-methoxy-ethyl)-1H-benzoimidazole

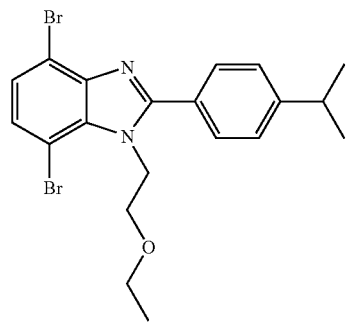

$R_t$=2.82 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 465 $(M+1)^+$ ($2\times^{79}Br$), 467 $(M+1)^+$ ($^{79}Br$, $^{81}Br$), 469 $(M+1)^+$ ($2\times^{81}Br$)

The title compound is prepared using the same methodology as described for the preparation of example 63.

EXAMPLE 65

4-Bromo-2-(4-isopropyl-phenyl)-7-methoxy-1-(2-methoxy-ethyl)-5-phenyl-1H-benzoimidazole

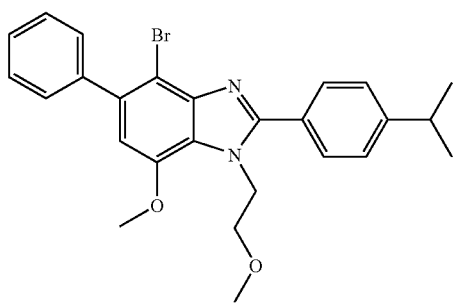

A mixture of 150 mg (0.283 mmol) 4-bromo-5-iodo-2-(4-isopropyl-phenyl)-7-methoxy-1-(2-methoxy-ethyl)-1H-benzoimidazole (example 30), 38 mg (0.312 mmol) phenylboronic acid, 60 mg (0.567 mmol) sodium carbonate and 16 mg (0.014 mmol) tetrakis(triphenylphosphine)palladium in 6 ml toluene/water (3:1) is stirred at 100° C. for 12 h. Then the reaction mixture is poured on water and extracted (3×) with ethyl acetate. The combined organic layers are washed with water (2×) and brine, dried over $MgSO_4$, filtered and concentrated in vacuo. The residue is purified by flash-chromatography on silica gel (hexane:EtOAc=3:1) to afford 40 mg of the title compound as a white solid.

$R_t$=2.42 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 479 $(M+1)^+$ ($^{79}Br$), 481 $(M+1)^+$ ($^{81}Br$)

Using the same methodology as described in example 65 the following compounds are prepared from the corresponding boronic acids:

EXAMPLE 66

4-Bromo-5-(3,4-dimethoxy-phenyl)-2-(4-isopropyl-phenyl)-7-methoxy-1-(2-methoxy-ethyl)-1H-benzoimidazole

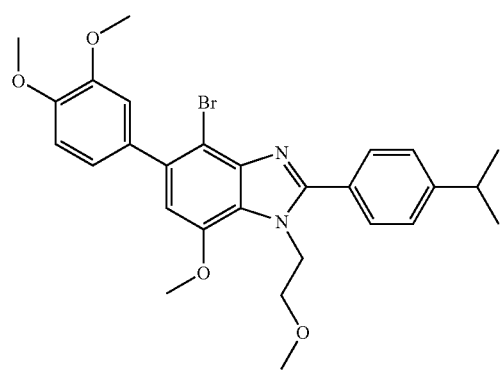

$R_t$ 2.31 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 539 $(M+1)^+$ ($^{79}Br$), 541 $(M+1)^+$ ($^{81}Br$)

EXAMPLE 67

3-[4-Bromo-2-(4-isopropyl-phenyl)-7-methoxy-1-(2-methoxy-ethyl)-1H-benzoimidazol-5-yl]-phenol

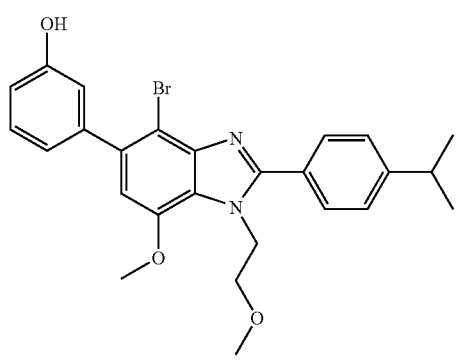

$R_t$=2.21 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 495 $(M+1)^+$ ($^{79}Br$), 497 $(M+1)^+$ ($^{81}Br$)

EXAMPLE 68

4-Bromo-2-(4-isopropyl-phenyl)-7-methoxy-1-(2-methoxy-ethyl)-5-(3-methoxy-phenyl)-1H-benzoimidazole

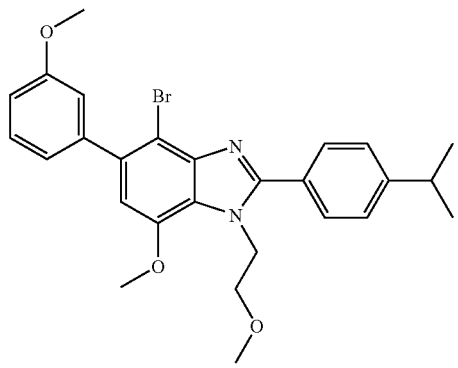

$R_t$=2.42 min (Waters Symmetry C8, 2.1×50 mm, detection 210-250 nM, 10% to 95% CH$_3$CN in H$_2$O in 2 min+0.05% TFA, flow rate 1.0 ml/min)

MS: 509 (M+1)$^+$ ($^{79}$Br), 511 (M+1)$^+$ ($^{81}$Br)

EXAMPLE 69

3-[4-Bromo-2-(4-isopropyl-phenyl)-7-methoxy-1-(2-methoxy-ethyl)-1H-benzoimidazol-5-yl]-benzoic Acid Ethyl Ester

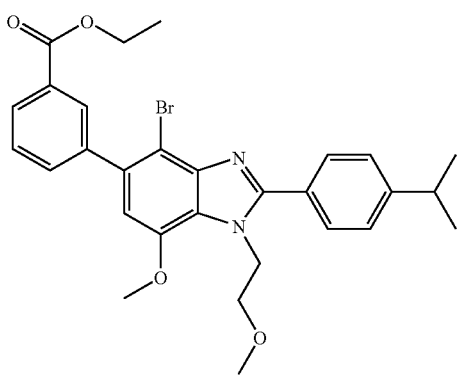

$R_t$=2.50 min (Waters Symmetry C8, 2.1×50 mm, detection 210-250 nM, 10% to 95% CH$_3$CN in H$_2$O in 2 min+0.05% TFA, flow rate 1.0 ml/min)

MS: 551 (M+1)$^+$ ($^{79}$Br), 553 (M+1)$^+$ ($^{81}$Br)

EXAMPLE 70

4-[4-Bromo-2-(4-isopropyl-phenyl)-7-methoxy-1-(2-methoxy-ethyl)-1H-benzoimidazol-5-yl]-benzoic Acid Ethyl Ester

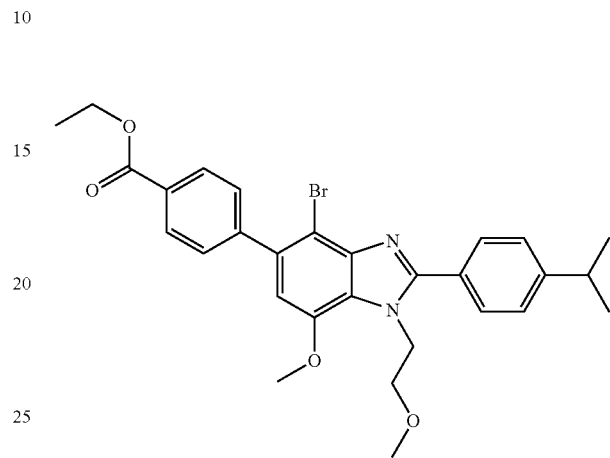

$R_t$=2.51 min (Waters Symmetry C8, 2.1×50 mm, detection 210-250 nM, 10% to 95% CH$_3$CN in H$_2$O in 2 min+0.05% TFA, flow rate 1.0 ml/min)

MS: 551 (M+1)$^+$ ($^{79}$Br), 553 (M+1)$^+$ ($^{81}$Br)

EXAMPLE 71

4-Bromo-2-(4-isopropyl-phenyl)-7-methoxy-1-(2-methoxy-ethyl)-5-pyridin-3-yl-1H-benzoimidazole

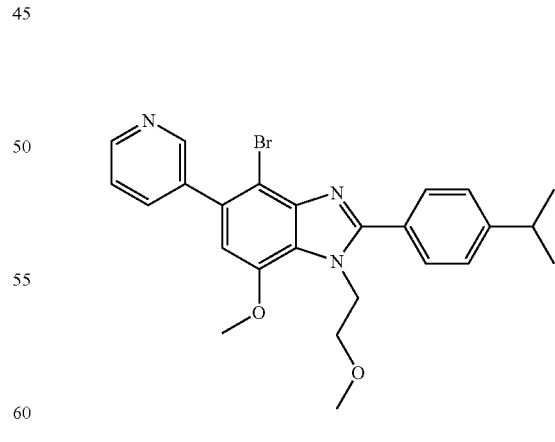

$R_t$=2.00 min (Waters Symmetry C8, 2.1×50 mm, detection 210-250 nM, 10% to 95% CH$_3$CN in H$_2$O in 2 min+0.05% TFA, flow rate 1.0 ml/min)

MS: 480 (M+1)$^+$ ($^{79}$Br), 482 (M+1)$^+$ ($^{81}$Br)

EXAMPLE 72

3-[4-Bromo-2-(4-isopropyl-phenyl)-7-methoxy-1-(2-methoxy-ethyl)-1H-benzoimidazol-5-yl]-benzonitrile

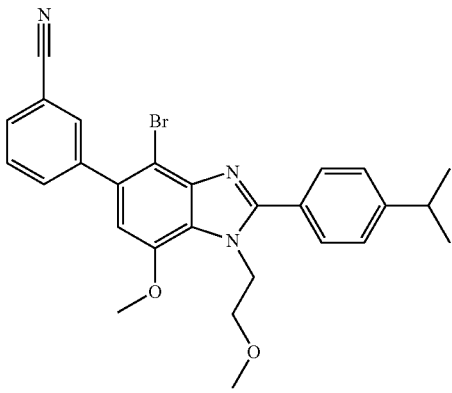

$R_t$=2.38 min (Waters Symmetry C8, 2.1×50 mm, detection 210-250 nM, 10% to 95% CH$_3$CN in H$_2$O in 2 min+0.05% TFA, flow rate 1.0 ml/min)

MS: 504 (M+1)$^+$ ($^{79}$Br), 506 (M+1)$^+$ ($^{81}$Br)

EXAMPLE 73

1-{5-[4-Bromo-2-(4-isopropyl-phenyl)-7-methoxy-1-(2-methoxy-ethyl)-1H-benzoimidazol-5-yl]-2-methoxy-phenyl}-ethanone

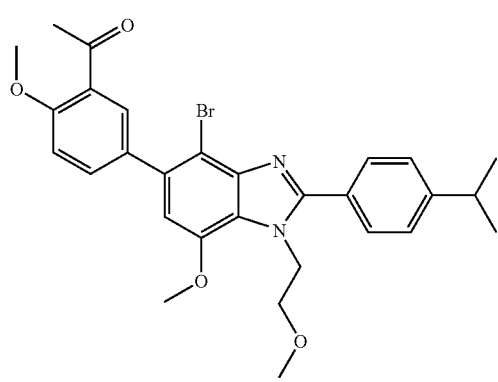

$R_t$=2.305 min (Waters Symmetry C8, 2.1×50 mm, detection 210-250 nM, 10% to 95% CH$_3$CN in H$_2$O in 2 min+0.05% TFA, flow rate 1.0 ml/min)

MS: 551 (M+1)$^+$ ($^{79}$Br), 553 (M+1)$^+$ ($^{81}$Br)

EXAMPLE 74

2-[4-Bromo-2-(4-isopropyl-phenyl)-7-methoxy-1-(2-methoxy-ethyl)-1H-benzoimidazol-5-yl]-benzonitrile

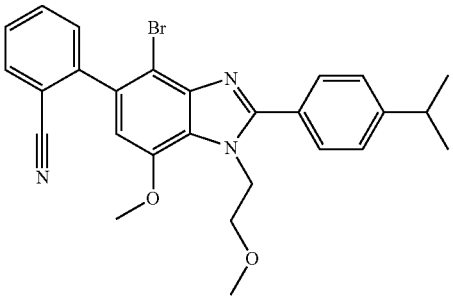

$R_t$=2.35 min (Waters Symmetry C8, 2.1×50 mm, detection 210-250 nM, 10% to 95% CH$_3$CN in H$_2$O in 2 min+0.05% TFA, flow rate 1.0 ml/min)

MS: 504 (M+1)$^+$ ($^{79}$Br), 506 (M+1)$^+$ ($^{81}$Br)

EXAMPLE 75

2-(4-Isopropyl-phenyl)-7-methoxy-1-(2-methoxy-ethyl)-5-(3-methoxy-phenyl)-1H-benzoimidazole

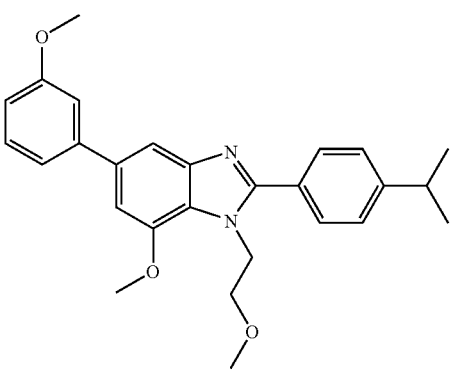

(The title compound is prepared from 5-bromo-2-(4-isopropyl-phenyl)-7-methoxy-1-(2-methoxy-ethyl)-1H-benzoimidazole instead of 4-bromo-5-iodo-2-(4-isopropyl-phenyl)-7-methoxy-1-(2-methoxy-ethyl)-1H-benzoimidazole)

$R_t$=2.06 min (Waters Symmetry C8, 2.1×50 mm, detection 210-250 nM, 10% to 95% CH$_3$CN in H$_2$O in 2 min+0.05% TFA, flow rate 1.0 ml/min)

MS: 417 (M+1)$^+$

EXAMPLE 76

4-Iodo-2-(4-isopropyl-phenyl)-7-methoxy-1-(2-methoxy-ethyl)-5-pyridin-4-yl-1H-benzoimidazole

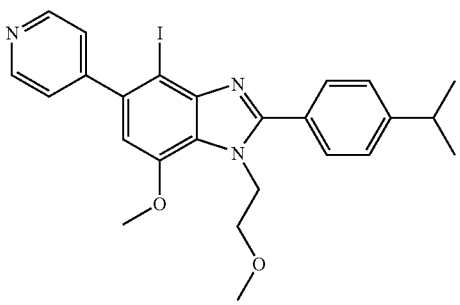

The compound is prepared using the methodology described in Example 40. The product of this reaction, 2-(4-Isopropyl-phenyl)-7-methoxy-1-(2-methoxy-ethyl)-5-pyridin-4-yl-1H-benzoimidazole, is iodinated as described in example 59 to afford the product.

$R_t$=2.008 min (Waters Symmetry C8, 2.1×50 mm, detection 210-250 nM, 10% to 95% $CH_3CN$ in $H_2O$ in 2 min+ 0.05% TFA, flow rate 1.0 ml/min)

MS: 528 (M+1)$^+$

EXAMPLE 77

4-Bromo-2-(4-isopropyl-phenyl)-7-methoxy-1-(2-methoxy-ethyl)-5-(4-methyl-pyrazol-1-ylmethyl)-1H-benzoimidazole

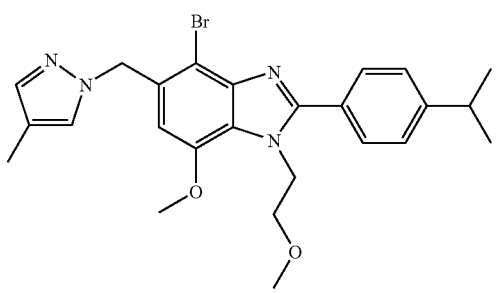

NaH (7 mg, 0.3 mmol) is added to a solution of 23 µl (0.30 mmol) 4-methylpyrazole in 2 ml DMF. The resulting mixture is stirred at room temperature for 1 h, then 119 mg (0.23 mmol) methanesulfonic acid 4-bromo-2-(4-isopropyl-phenyl)-7-methoxy-1-(2-methoxy-ethyl)-1H-benzoimidazol-5-ylmethyl ester is added. Stirring is continued for 20 h. After that the reaction mixture is poured on water and extracted (3×) with ethyl acetate. The combined organic layers are washed with water (2×) and brine, dried over $MgSO_4$, filtered and concentrated in vacuo. The residue is purified by flash-chromatography on silica gel (dichloromethane:isopropanol=95:5) to afford 80 mg of the title compound as a white foam.

$R_t$=2.28 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 497 (M+1)$^+$ ($^{79}Br$), 499 (M+1)$^+$ ($^{81}Br$)

The starting materials can be prepared as follows:

a) Methanesulfonic Acid 4-bromo-2-(4-isopropyl-phenyl)-7-methoxy-1-(2-methoxy-ethyl)-1H-benzoimidazol-5-ylmethyl Ester

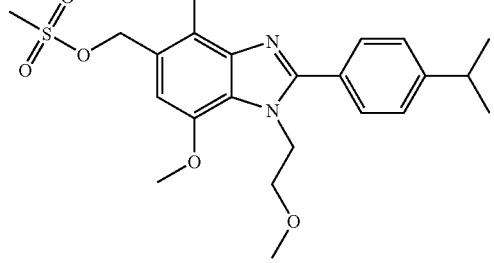

A mixture of 100 mg (0.23 mmol) [4-bromo-2-(4-isopropyl-phenyl)-7-methoxy-1-(2-methoxy-ethyl)-1H-benzoimidazol-5-yl]-methanol, 26 µl (0.33 mmol) methanesulfonyl chloride and 60 µl (0.35 mmol) diisopropylethylamine in 4 ml dichloromethane is stirred at 0° C. for 2 h. The reaction mixture is poured on water and extracted (3×) with ethyl acetate. The combined organic layers are washed with water (2×) and brine, dried over $MgSO_4$, filtered and concentrated in vacuo to afford 120 mg of the title compound as an oil that is used directly in the next reaction.

b) [4-Bromo-2-(4-isopropyl-phenyl)-7-methoxy-1-(2-methoxy-ethyl)-1H-benzoimidazol-5-yl]-methanol

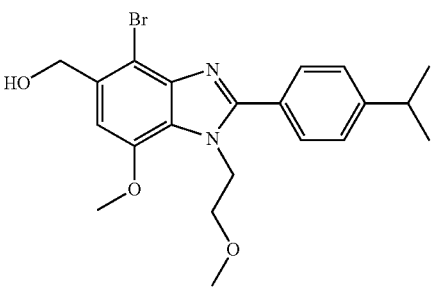

$NaBH_4$ (65 mg, 1.72 mmol) is added to a solution of 370 mg (0.858 mmol) 4-bromo-2-(4-isopropyl-phenyl)-7-methoxy-1-(2-methoxy-ethyl)-1H-benzoimidazole-5-carbaldehyde in 5 ml absolute ethanol at 0° C. The reaction mixture is stirred at 0° C. for 20 min. Then the reaction mixture is poured on water and extracted (3×) with dichloromethane/isopropanol (3:1). The combined organic layers are washed with water (2×) and brine, dried over MgSO₄, filtered and concentrated in vacuo to afford 380 mg of the title compound as a pure crystalline solid.

c) 4-Bromo-2-(4-isopropyl-phenyl)-7-methoxy-1-(2-methoxy-ethyl)-1H-benzoimidazole-5-carbaldehyde

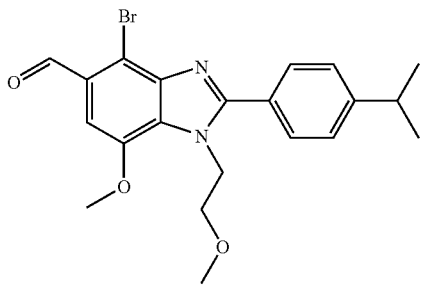

The title compound is prepared from 4-bromo-2-(4-isopropyl-phenyl)-7-methoxy-1-(2-methoxy-ethyl)-1H-benzoimidazole-5-carbonitrile (example 33) using the same reaction conditions as described in example 35 step d).

Reaction of methanesulfonic acid 4-bromo-2-(4-isopropyl-phenyl)-7-methoxy-1-(2-methoxy-ethyl)-1H-benzoimidazol-5-ylmethyl ester with either imidazole, 4-bromo-3-methyl-1H-pyrazole, 3,5-dimethyl-1H-pyrazole, 1H-imidazole-2-carboxylic acid ethyl ester, 1H-Imidazole-4-carboxylic acid methyl ester, 3H-imidazo[4,5-b]pyridine, indazole or 5-methyl-2H-tetrazole using the same reaction conditions as described for the preparation of example 77 led to the following compounds:

EXAMPLE 78

4-Bromo-5-imidazol-1-ylmethyl-2-(4-isopropyl-phenyl)-7-methoxy-1-(2-methoxy-ethyl)-1H-benzoimidazole

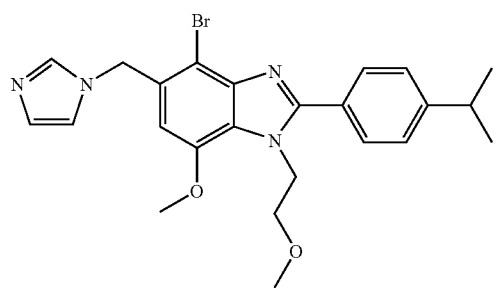

$R_t$=1.93 min (Waters Symmetry C8, 2.1×50 mm, detection 210-250 nM, 10% to 95% CH₃CN in H₂O in 2 min+0.05% TFA, flow rate 1.0 ml/min)

MS: 483 (M+1)⁺ ($^{79}$Br), 485 (M+1)⁺ ($^{81}$Br)

EXAMPLE 79

4-Bromo-5-(4-bromo-5-methyl-pyrazol-1-ylmethyl)-2-(4-isopropyl-phenyl)-7-methoxy-1-(2-methoxy-ethyl)-1H-benzoimidazole

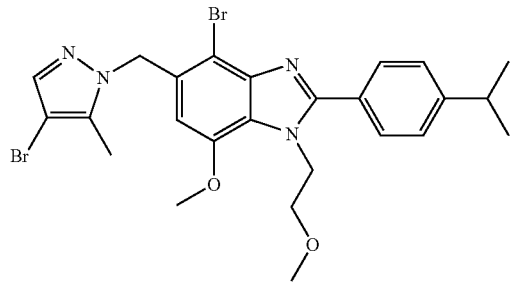

$R_t$=2.37 min (Waters Symmetry C8, 2.1×50 mm, detection 210-250 nM, 10% to 95% CH₃CN in H₂O in 2 min+0.05% TFA, flow rate 1.0 ml/min)

MS: 575 (M+1)⁺ (2×$^{79}$Br), 577 (M+1)⁺ ($^{79}$Br, $^{81}$Br), 579 (M+1)⁺ (2×$^{81}$Br)

EXAMPLE 80

4-Bromo-5-(4-bromo-3-methyl-pyrazol-1-ylmethyl)-2-(4-isopropyl-phenyl)-7-methoxy-1-(2-methoxy-ethyl)-1H-benzoimidazole

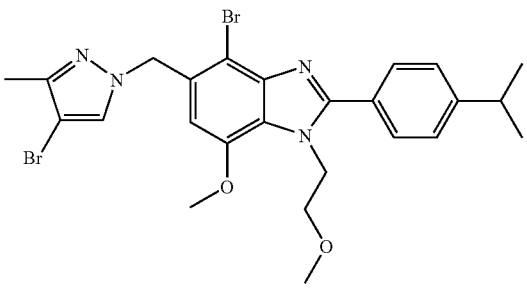

$R_t$=2.36 min (Waters Symmetry C8, 2.1×50 mm, detection 210-250 nM, 10% to 95% CH₃CN in H₂O in 2 min+0.05% TFA, flow rate 1.0 ml/min)

MS: 575 (M+1)⁺ (2×$^{79}$Br), 577 (M+1)⁺ ($^{79}$Br, $^{81}$Br), 579 (M+1)⁺ (2×$^{81}$Br)

EXAMPLE 81

4-Bromo-5-(3,5-dimethyl-pyrazol-1-ylmethyl)-2-(4-isopropyl-phenyl)-7-methoxy-1-(2-methoxy-ethyl)-1H-benzoimidazole

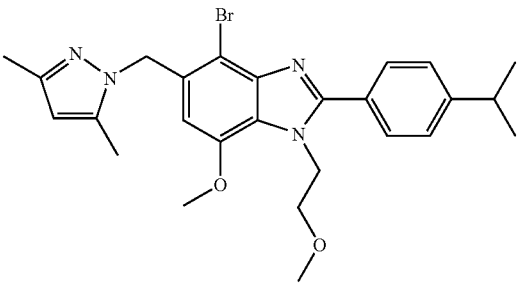

R$_t$=5.39 min (Waters Symmetry C8, 2.1×50 mm, detection 210-250 nM, 10% to 95% CH$_3$CN in H$_2$O in 7 min+0.05% TFA, flow rate 0.5 ml/min)
MS: 511 (M+1)$^+$ ($^{79}$Br), 513 (M+1)$^+$ ($^{81}$Br)

EXAMPLE 82

1-[4-Bromo-1-(2-hydroxy-ethyl)-2-(4-isopropyl-phenyl)-7-methoxy-1H-benzoimidazol-5-ylmethyl]-1H-imidazole-2-carboxylic Acid Ethyl Ester

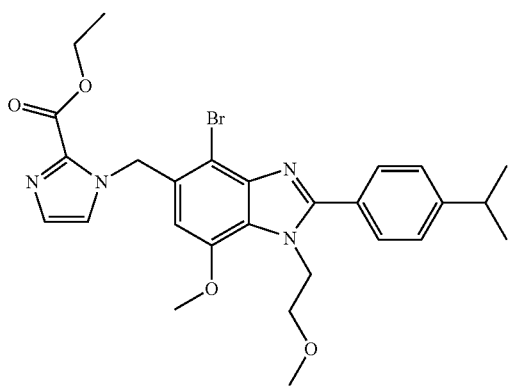

R$_t$=2.08 min (Waters Symmetry C8, 2.1×50 mm, detection 210-250 nM, 10% to 95% CH$_3$CN in H$_2$O in 2 min+0.05% TFA, flow rate 1.0 ml/min)
MS: 555 (M+1)$^+$ ($^{79}$Br), 557 (M+1)$^+$ ($^{81}$Br)

EXAMPLE 83

4-Bromo-2-(4-isopropyl-phenyl)-7-methoxy-1-(2-methoxy-ethyl)-5-(2-methoxymethyl-imidazol-1-ylmethyl)-1H-benzoimidazole

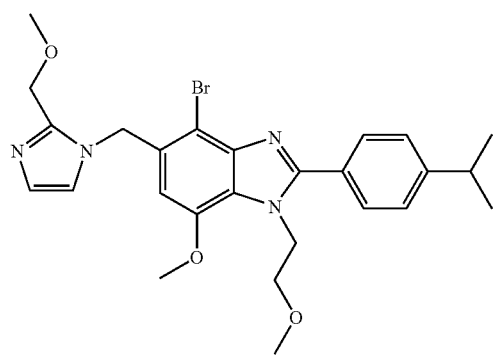

R$_t$=1.96 min (Waters Symmetry C8, 2.1×50 mm, detection 210-250 nM, 10% to 95% CH$_3$CN in H$_2$O in 2 min+0.05% TFA, flow rate 1.0 ml/min)
MS: 527 (M+1)$^+$ ($^{79}$Br), 529 (M+1)$^+$ ($^{81}$Br)

EXAMPLE 84

4-Bromo-2-(4-isopropyl-phenyl)-7-methoxy-1-(2-methoxy-ethyl)-5-(2-methylsulfanyl-imidazol-1-ylmethyl)-1H-benzoimidazole

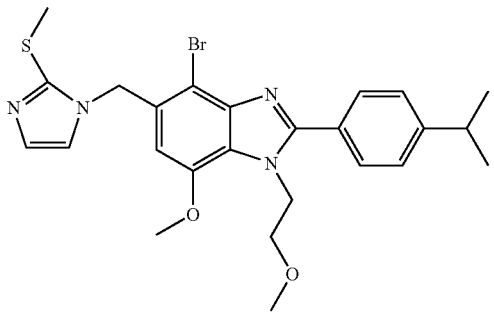

R$_t$=1.98 min (Waters Symmetry C8, 2.1×50 mm, detection 210-250 nM, 10% to 95% CH$_3$CN in H$_2$O in 2 min+0.05% TFA, flow rate 1.0 ml/min)
MS: 529 (M+1)$^+$ ($^{79}$Br), 531 (M+1)$^+$ ($^{81}$Br)

EXAMPLE 85

1-[4-Bromo-2-(4-isopropyl-phenyl)-7-methoxy-1-(2-methoxy-ethyl)-1H-benzoimidazol-5-ylmethyl]-1H-benzoimidazol-2-ol

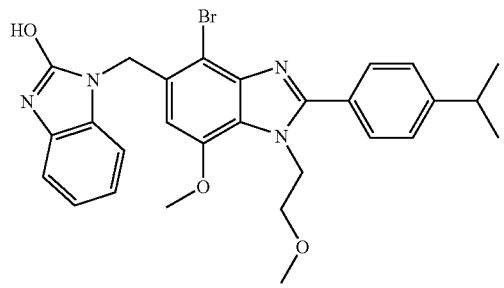

R$_t$=2.20 min (Waters Symmetry C8, 2.1×50 mm, detection 210-250 nM, 10% to 95% CH$_3$CN in H$_2$O in 2 min+0.05% TFA, flow rate 1.0 ml/min)
MS: 549 (M+1)$^+$ ($^{79}$Br), 551 (M+1)$^+$ ($^{81}$Br)

EXAMPLE 86

4-Bromo-2-(4-isopropyl-phenyl)-7-methoxy-1-(2-methoxy-ethyl)-5-(2-methylsulfanyl-benzoimidazol-1-ylmethyl)-1H-benzoimidazole

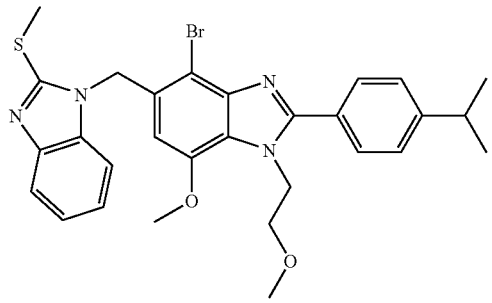

$R_t$=2.18 min (Waters Symmetry C8, 2.1×50 mm, detection 210-250 nM, 10% to 95% CH$_3$CN in H$_2$O in 2 min+0.05% TFA, flow rate 1.0 ml/min)

MS: 579 (M+1)$^+$ ($^{79}$Br), 581 (M+1)$^+$ ($^{81}$Br)

EXAMPLE 87

4-Bromo-2-(4-isopropyl-phenyl)-5-(2-methanesulfinyl-benzoimidazol-1-ylmethyl)-7-methoxy-1-(2-methoxy-ethyl)-1H-benzoimidazole

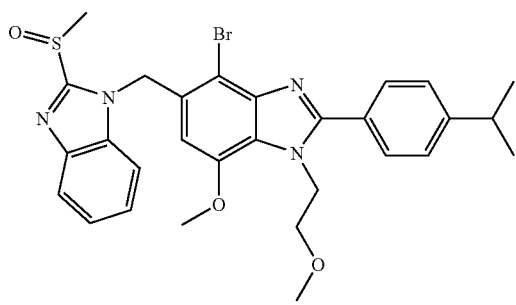

$R_t$=2.20 min (Waters Symmetry C8, 2.1×50 mm, detection 210-250 nM, 10% to 95% CH$_3$CN in H$_2$O in 2 min+0.05% TFA, flow rate 1.0 ml/min)

MS: 595 (M+1)$^+$ ($^{79}$Br), 597 (M+1)$^+$ ($^{81}$Br)

EXAMPLE 88

4-Bromo-2-(4-isopropyl-phenyl)-7-methoxy-5-(2-methoxy-benzoimidazol-1-ylmethyl)-1-(2-methoxy-ethyl)-1H-benzoimidazole

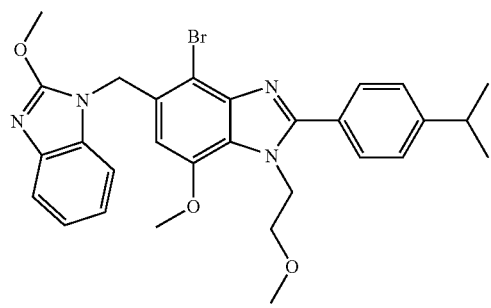

$R_t$=2.26 min (Waters Symmetry C8, 2.1×50 mm, detection 210-250 nM, 10% to 95% CH$_3$CN in H$_2$O in 2 min+0.05% TFA, flow rate 1.0 ml/min)

MS: 563 (M+1)$^+$ ($^{79}$Br), 565 (M+1)$^+$ ($^{81}$Br)

EXAMPLE 89

3-[4-Bromo-1-(2-hydroxy-ethyl)-2-(4-isopropyl-phenyl)-7-methoxy-1H-benzoimidazol-5-ylmethyl]-3H-imidazole-4-carboxylic Acid Methyl Ester

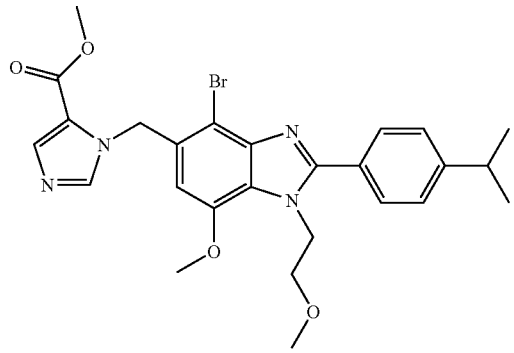

$R_t$=2.02 min (Waters Symmetry C8, 2.1×50 mm, detection 210-250 nM, 10% to 95% CH$_3$CN in H$_2$O in 2 min+0.05% TFA, flow rate 1.0 ml/min)

MS: 541 (M+1)$^+$ ($^{79}$Br), 543 (M+1)$^+$ ($^{81}$Br)

EXAMPLE 90

2-[4-Bromo-5-imidazo[4,5-b]pyridin-3-ylmethyl-2-(4-isopropyl-phenyl)-7-methoxy-benzoimidazol-1-yl]-ethanol

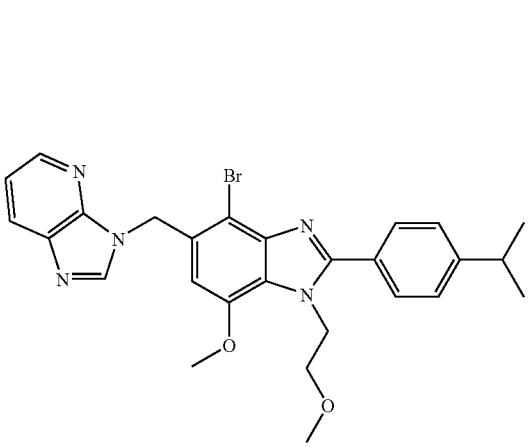

$R_t$=2.05 min (Waters Symmetry C8, 2.1×50 mm, detection 210-250 nM, 10% to 95% CH$_3$CN in H$_2$O in 2 min+0.05% TFA, flow rate 1.0 ml/min)

MS: 534 (M+1)$^+$ ($^{79}$Br), 536 (M+1)$^+$ ($^{81}$Br)

EXAMPLE 91

2-[4-Bromo-5-indazol-1-ylmethyl-2-(4-isopropyl-phenyl)-7-methoxy-benzoimidazol-1-yl]-ethanol

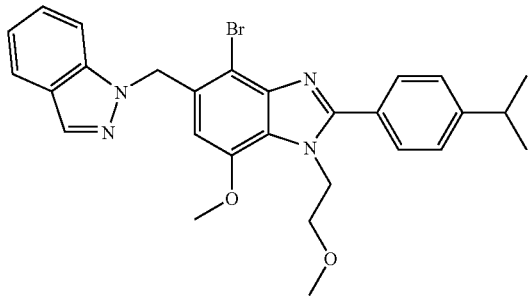

$R_t$=2.34 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 533 (M+1)$^+$ ($^{79}$Br), 535 (M+1)$^+$ ($^{81}$Br)

EXAMPLE 92

2-[4-Bromo-2-(4-isopropyl-phenyl)-7-methoxy-5-(5-methyl-tetrazol-2-ylmethyl)-benzoimidazol-1-yl]-ethanol

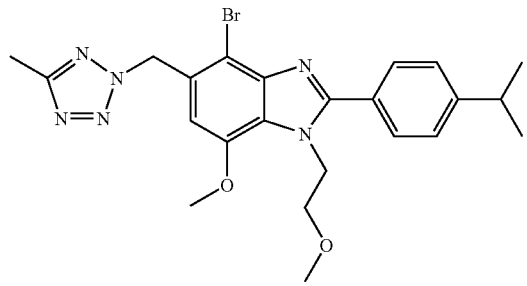

$R_t$=2.21 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 499 (M+1)$^+$ ($^{79}$Br), 501 (M+1)$^+$ ($^{81}$Br)

EXAMPLE 93

4-Bromo-5-(4-bromo-5-methyl-pyrazol-1-ylmethyl)-2-(4-cyclopropyl-phenyl)-7-methoxy-1-(2-methoxy-ethyl)-1H-benzoimidazole

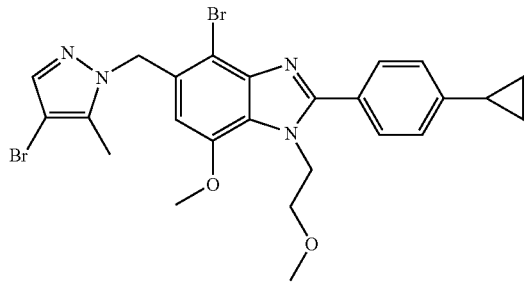

The compound is prepared as described in example 79 by using 4-cyclopropyl-benzoic acid instead of 4-isopropyl-benzoic acid.

$R_t$=2.28 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 573 (M+1)$^+$ (2×$^{79}$Br), 575 (M+1)$^+$ ($^{79}$Br, $^{81}$Br), 577 (M+1)$^+$ (2×$^{81}$Br)

EXAMPLE 94

4-Bromo-2-(4-isopropyl-phenyl)-7-methoxy-5-(4-methyl-pyrazol-1-ylmethyl)-1-(2-methylsulfanyl-ethyl)-1H-benzoimidazole

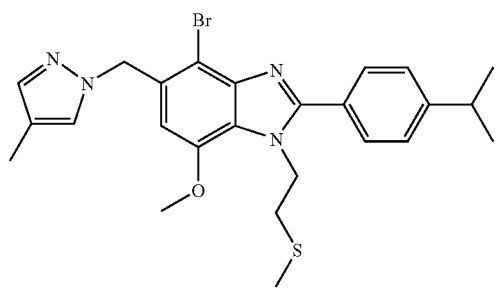

The compound is prepared using as described in example 77 by using 1-bromo-2-methylsulfanyl-ethane instead of 1-bromo-2-methoxy-ethane $R_t$=2.33 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 513 (M+1)$^+$ ($^{79}$Br), 515 (M+1)$^+$ ($^{81}$Br)

EXAMPLE 95

4-Bromo-5-isopropoxymethyl-2-(4-isopropyl-phenyl)-7-methoxy-1-(2-methoxy-ethyl)-1H-benzoimidazole

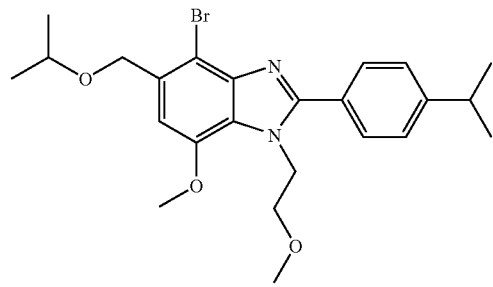

The title compound is prepared using the same methodology as described in example 77 by using 2-propanol (instead of 4-methyl-pyrazole).

$R_t$=2.33 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 475 (M+1)$^+$ ($^{79}$Br), 477 (M+1)$^+$ ($^{81}$Br)

EXAMPLE 96

1-[4-Bromo-2-(4-isopropyl-phenyl)-7-methoxy-1-(2-methoxy-ethyl)-1H-benzoimidazol-5-ylmethyl]-pyrrolidin-2-one

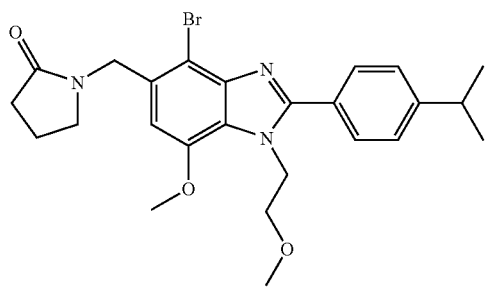

The title compound is prepared from 1-[2-(4-isopropyl-phenyl)-7-methoxy-1-(2-methoxy-ethyl)-1H-benzoimidazol-5-ylmethyl]-pyrrolidin-2-one using the same methodology as described in example 35.

$R_t$=2.12 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 500 (M+1)$^+$ ($^{79}$Br), 502 (M+1)$^+$ ($^{81}$Br)

The starting material can be prepared as follows:

a) 1-[2-(4-isopropyl-phenyl)-7-methoxy-1-(2-methoxy-ethyl)-1H-benzoimidazol-5-ylmethyl]-pyrrolidin-2-one

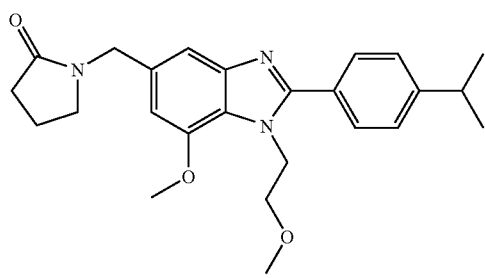

A solution of 50 mg (0.143 mmol) C-[2-(4-Isopropyl-phenyl)-7-methoxy-1-(2-methoxy-ethyl)-1H-benzoimidazol-5-yl]-methylamine, 28 mg (0.143 mmol) ethyl-4-bromobutyrate and 28 μl (0.2 mmol) triethylamine in 4 ml 3-methyl-1-butanol is stirred at reflux temperature for 8 h. Then the reaction mixture is poured on water and extracted (3×) with EtOAc. The combined organic layers are washed with water (2×) and brine, dried over $MgSO_4$, filtered and concentrated in vacuo. The residue is purified by flash-chromatography on silica gel (EtOAc:MeOH=98:2) to afford 20 mg of the title compound as a colorless oil.

b) C-[2-(4-Isopropyl-phenyl)-7-methoxy-1-(2-methoxy-ethyl)-1H-benzoimidazol-5-yl]-methylamine

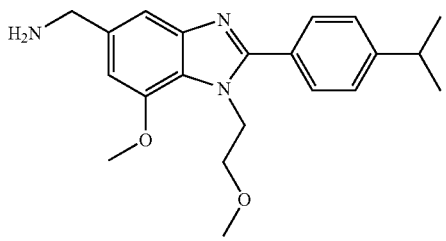

To a solution of 100 mg (0.286 mmol) 2-(4-Isopropyl-phenyl)-7-methoxy-1-(2-methoxy-ethyl)-1H-benzoimidazole-5-carbonitrile in 4 ml THF, $LiAlH_4$ (54 mg, 1.43 mmol) is added. The reaction mixture is stirred at reflux temperature for 2 h. After that methanol (0.5 ml) and 5 ml 15% NaOH-solution is added. This mixture is filtered and the filtrate is extracted (3×) with EtOAc. The combined organic layers are washed with water (2×) and brine, dried over $MgSO_4$, filtered and concentrated in vacuo to afford 60 mg of the title compound as an oil.

EXAMPLE 97

4-Bromo-2-(4-isopropyl-phenyl)-7-methoxy-1-(2-methoxy-ethyl)-5-phenylsulfanyl-1H-benzoimidazole

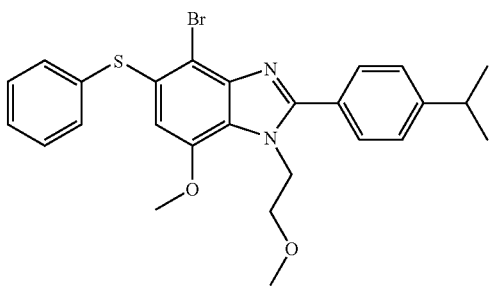

The title compound is prepared from 2-(4-isopropyl-phenyl)-7-methoxy-1-(2-methoxy-ethyl)-5-phenylsulfanyl-1H-benzoimidazole using the method described for the preparation of example 35

$R_t$=2.49 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 511 (M+1)$^+$ ($^{79}$Br), 513 (M+1)$^+$ ($^{81}$Br)

The starting material 2-(4-isopropyl-phenyl)-7-methoxy-1-(2-methoxy-ethyl)-5-phenylsulfanyl-1H-benzoimidazole can be prepared as follows:

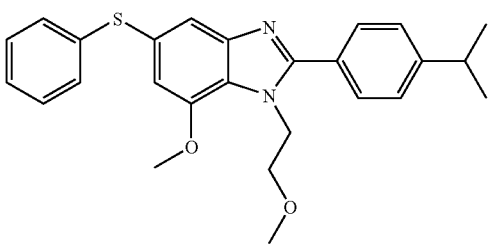

A mixture of 200 mg (0.491 mmol) 5-bromo-2-(4-isopropyl-phenyl)-7-methoxy-1-(2-methoxy-ethyl)-1H-benzoimidazole (example 22), 354 mg $Cs_2CO_3$, 9 mg CuI, 56 µl Ph-SH and 2 ml N-methylpyrrolidone is stirred at 200° C. for 2 h. Then the reaction mixture is poured on water and extracted (3×) with ethyl acetate. The combined organic layers are washed with water (2×) and brine, dried over $MgSO_4$, filtered and concentrated in vacuo. The residue is purified by flash-chromatography on silica gel (hexane:EtOAc=3:1) to afford 55 mg of the title compound as an oil.

EXAMPLE 98

5-Benzenesulfinyl-4-bromo-2-(4-isopropyl-phenyl)-7-methoxy-1-(2-methoxy-ethyl)-1H-benzoimidazole

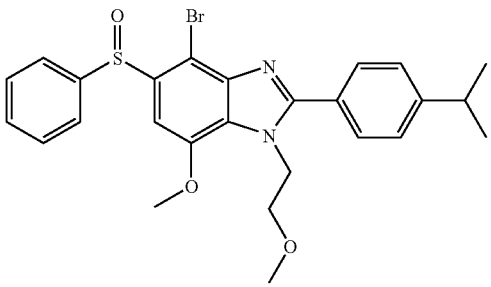

The title compound is prepared from 4-bromo-2-(4-isopropyl-phenyl)-7-methoxy-1-(2-methoxy-ethyl)-5-phenylsulfanyl-1H-benzoimidazole using the method described for the preparation of example 47 (oxidation reaction carried out at 40° C. for 4 h).

$R_t$=2.45 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 527 (M+1)$^+$ ($^{79}$Br), 529 (M+1)$^+$ ($^{81}$Br)

EXAMPLE 98a

4-Bromo-2-(4-isopropyl-phenyl)-7-methoxy-1-(2-methoxy-ethyl)-5-phenoxy-1H-benzoimidazole

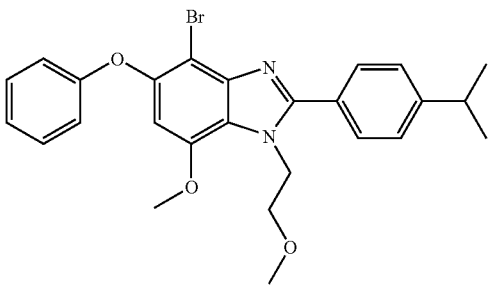

The title compound is prepared using the method described for the preparation of example 97.

$R_t$=2.39 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 495 (M+1)$^+$ ($^{79}$Br), 497 (M+1)$^+$ ($^{81}$Br)

EXAMPLE 99

5-Benzyl-2-(4-isopropyl-phenyl)-7-methoxy-1-(2-methoxy-ethyl)-4-trifluoromethyl-1H-benzoimidazole

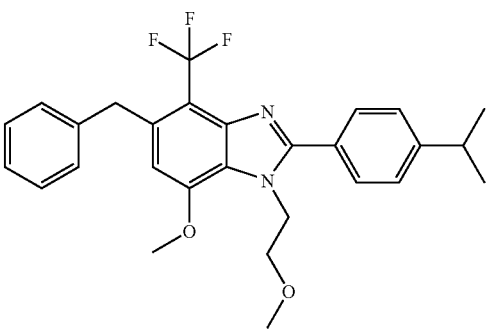

The title compound is prepared from 2-(4-isopropyl-phenyl)-7-methoxy-1-(2-methoxy-ethyl)-4-trifluoromethyl-1H-benzoimidazole-5-carbaldehyde and phenylmagnesiumbromide as described in examples 35 and 51.

$R_t$=2.40 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 483 (M+1)$^+$

The starting material 2-(4-isopropyl-phenyl)-7-methoxy-1-(2-methoxy-ethyl)-4-trifluoromethyl-1H-benzoimidazole-5-carbaldehyde can be prepared as follows:

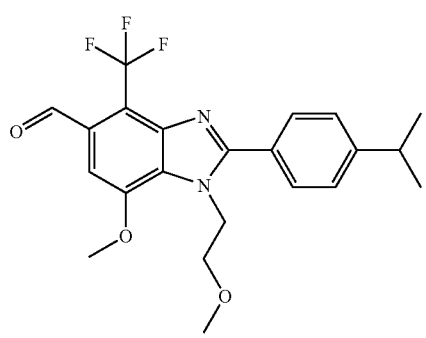

A mixture of 550 mg (1.45 mmol) 4-Iodo-2-(4-isopropyl-phenyl)-7-methoxy-1-(2-methoxy-ethyl)-1H-benzoimidazole-5-carbaldehyde (example 26k), 28 mg CuI (0.145 mmol), 555 µl (4.36 mmol) methyl-2,2-difluoro-2-(fluorosulfonyl)acetate and 2 ml DMF is stirred at 120° C. for 2 h. Then the reaction mixture is poured on water and extracted (3×) with ethyl acetate. The combined organic layers are washed with water (2×) and brine, dried over $MgSO_4$, filtered and concentrated in vacuo. The residue is purified by flash-chromatography on silica gel (100% hexane –>100% EtOAc) to afford 525 mg of the title compound as a colorless crystalline solid.

Using the same method the following compounds are also prepared:

EXAMPLE 100

2-(4-Isopropyl-phenyl)-7-methoxy-5-(2-methoxy-benzyl)-1-(2-methoxy-ethyl)-4-trifluoromethyl-1H-benzoimidazole

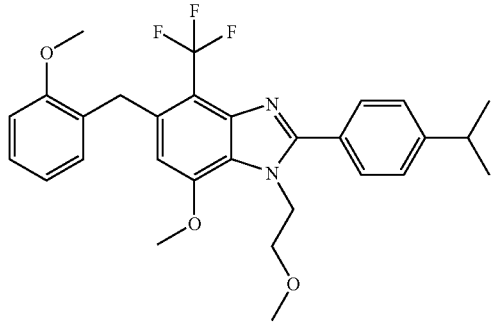

$R_t$=2.40 min (Waters Symmetry C8, 2.1×50 mm, detection 210-250 nM, 10% to 95% CH$_3$CN in H$_2$O in 2 min+0.05% TFA, flow rate 1.0 ml/min)

MS: 513 (M+1)$^+$

EXAMPLE 101

2-(4-Isopropyl-phenyl)-7-methoxy-1-(2-methoxy-ethyl)-5-pyridin-2-ylmethyl-4-trifluoromethyl-1H-benzoimidazole

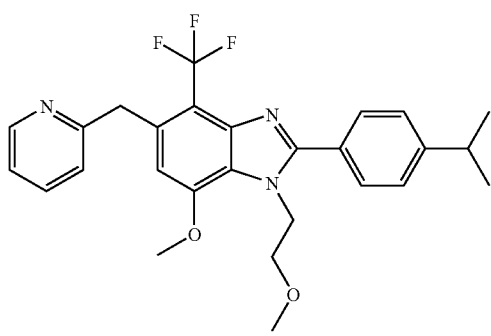

$R_t$=1.99 min (Waters Symmetry C8, 2.1×50 mm, detection 210-250 nM, 10% to 95% CH$_3$CN in H$_2$O in 2 min+0.05% TFA, flow rate 1.0 ml/min)

MS: 484 (M+1)$^+$

EXAMPLE 101a 2-(4-Isopropyl-phenyl)-7-methoxy-1-(2-methoxy-ethyl)-5-thiazol-2-ylmethyl-4-trifluoromethyl-1H-benzoimidazole

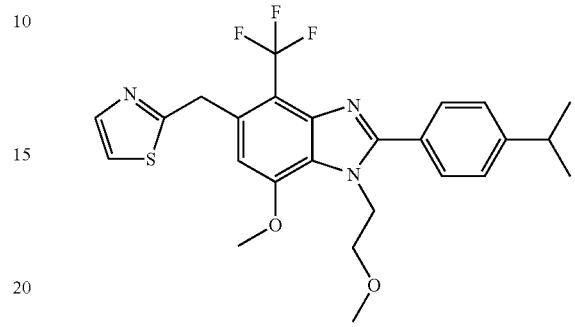

$R_t$=2.22 min (Waters Symmetry C8, 2.1×50 mm, detection 210-250 nM, 10% to 95% CH$_3$CN in H$_2$O in 2 min+0.05% TFA, flow rate 1.0 ml/min)

MS: 490 (M+1)$^+$

EXAMPLE 102

2-(4-Isopropyl-phenyl)-7-methoxy-1-(2-methoxy-ethyl)-5-pyrazol-1-ylmethyl-4-trifluoromethyl-1H-benzoimidazole

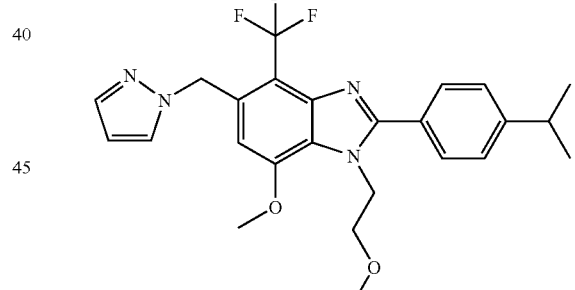

The title compound is prepared from methanesulfonic acid 2-(4-isopropyl-phenyl)-7-methoxy-1-(2-methoxy-ethyl)-4-trifluoromethyl-1H-benzoimidazol-5-ylmethyl ester and pyrrazole as described in examples 35 and 77.

$R_t$=2.25 min (Waters Symmetry C8, 2.1×50 mm, detection 210-250 nM, 10% to 95% CH$_3$CN in H$_2$O in 2 min+0.05% TFA, flow rate 1.0 ml/min)

MS: 473 (M+1)$^+$

The starting material methanesulfonic acid 2-(4-isopropyl-phenyl)-7-methoxy-1-(2-methoxy-ethyl)-4-trifluoromethyl-1H-benzoimidazol-5-ylmethyl ester can be prepared from 2-(4-isopropyl-phenyl)-7-methoxy-1-(2-methoxy-ethyl)-4-trifluoromethyl-1H-benzoimidazole-5-carbaldehyde (see example 99) using the method described for the preparation

EXAMPLE 103

4-Bromo-2-(4-isopropyl-phenyl)-7-methoxy-1-(2-methoxy-ethyl)-5-phenoxy methyl-1H-benzoimidazole

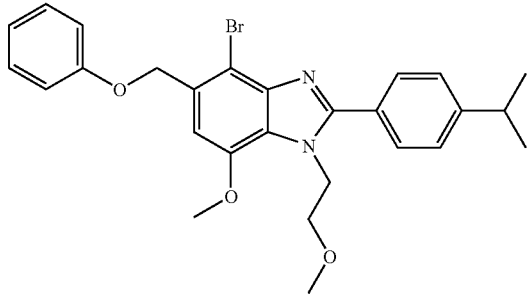

To a cooled solution (ice bath) of phenol (7.2 mg, 0.077 mmol) in 1 ml DMF, NaH (3.1 mg, 0.077 mmol, 60% in mineral oil) is added and the reaction is warmed to RT. Methanesulfonic acid 4-bromo-2-(4-isopropyl-phenyl)-7-methoxy-1-(2-methoxy-ethyl)-1H-benzoimidazol-5-ylmethyl ester (30 mg, 0.059 mmol) is added and the reaction mixture is heated to 60° C. for 1 h. After that the reaction mixture is extracted with sat. NaHCO$_3$-solution and diethyl ether. The combined organic layers are washed with water and brine, dried over MgSO$_4$, filtered and concentrated in vacuo. The residue is purified by flash-chromatography on silica gel (hexane:EtOAc=1:1) to afford 28 mg of the title compound as pale yellow crystals.

R$_t$=2.42 min (Waters Symmetry C8, 2.1×50 mm, detection 210-250 nM, 10% to 95% CH$_3$CN in H$_2$O in 2 min+0.05% TFA, flow rate 11.0 ml/min)

MS: 509 (M+1)$^+$ ($^{79}$Br), 511 (M+1)$^+$ ($^{81}$Br)

The starting materials can be prepared as described in example 77 (steps a to c):

a) Methanesulfonic Acid 4-bromo-2-(4-isopropyl-phenyl)-7-methoxy-1-(2-methoxy-ethyl)-1H-benzoimidazol-5-ylmethyl Ester

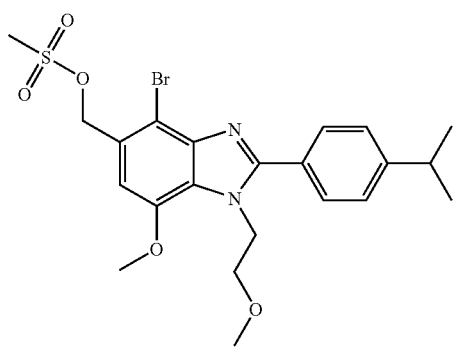

A solution of 200 mg (0.462 mmol) [4-Bromo-2-(4-isopropyl-phenyl)-7-methoxy-1-(2-methoxy-ethyl)-1H-benzoimidazol-5-yl]-methanol is dissolved in 5 ml CH$_2$Cl$_2$. The solution is cooled to 0° C. and methanesulfonyl chloride (47 ul, 0.600 mmol) and Huenig's base (103 ul, 0.600 mmol) is added. After 1 h the reaction is extracted with CH$_2$Cl$_2$/10% citric acid. The organic layer is dried over MgSO$_4$, filtered and concentrated in vacuo to give 240 mg of material which is used without further purification.

b) [4-Bromo-2-(4-isopropyl-phenyl)-7-methoxy-1-(2-methoxy-ethyl)-1H-benzoimidazol-5-yl]-methanol

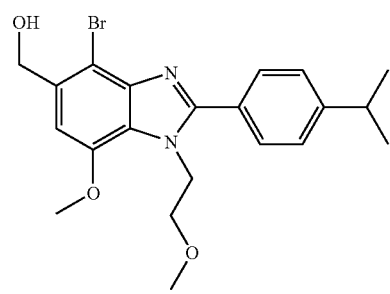

2.08 g (4.82 mmol) of 4-Bromo-2-(4-isopropyl-phenyl)-7-methoxy-1-(2-methoxy-ethyl)-1H-benzoimidazole-5-carbaldehyde is dissolved in 60 ml Ethanol and NaBH$_4$ (365 mg, 9.64 mmol) is added. After stirring for 30 min ice/water is added and the reaction mixture is extracted with ethyl acetate (3×). The organic layer is washed with water (3×) and brine (2×), dried (Na$_2$SO$_4$) and concentrated in vacuo. The residue is crystallized from diethyl ether/hexanes to give 1.85 g of colorless crystals.

c) 4-Bromo-2-(4-isopropyl-phenyl)-7-methoxy-1-(2-methoxy-ethyl)-1H-benzoimidazole-5-carbaldehyde

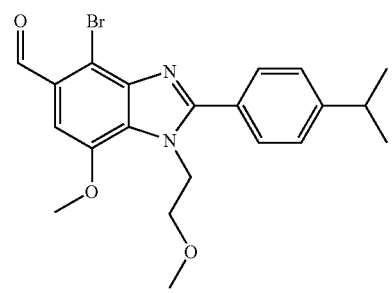

3.0 g (8.51 mmol) of 2-(4-Isopropyl-phenyl)-7-methoxy-1-(2-methoxy-ethyl)-1H-benzoimidazole-5-carbaldehyde is dissolved in 90 ml acetic acid. Bromine (437 ul, 8.51 mmol) is added dropwise and the reaction is stirred for 5 h at RT. Ice/water is added and the reaction mixture is extracted with ethyl acetate (3×). The organic layer is washed with water (3×) and brine (2×), dried (Na$_2$SO$_4$) and concentrated in vacuo. The residue is purified by flash-chromatography on silica gel (hexanes/EtOAc) to give 2:08 g of colorless crystals.

d) 2-(4-Isopropyl-phenyl)-7-methoxy-1-(2-methoxy-ethyl)-1H-benzoimidazole-5-carbaldehyde

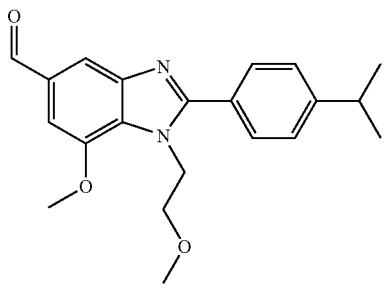

To a solution of 7.02 g (20.1 mmol) of 1-(2-Hydroxy-ethyl)-2-(4-isopropyl-phenyl)-7-methoxy-1H-benzoimidazole-5-carbonitrile in 280 ml pyridine is added 140 ml acetic acid. After addition of a solution of 14.1 g (161 mmol) sodium hypophosphite in 140 ml water and heating to 50° C. Raney-Nickel is added in 50 mg portions (3× over 12 h) until the reaction is complete. The reaction mixtures is cooled to RT, ice/water is added and the reaction mixture is extracted with ethyl acetate (3×). The organic layer is washed with water, in vacuo and azeotroped with toluene. The residue is suspended in 100 ml $CH_2Cl_2$, filtered and washed with $CH_2Cl_2$ and ethyl acetate. The mother liquor is evaporated and purified by flash-chromatography on silica gel (hexanes/EtOAc) to give 3.78 g of colorless crystals.

e) 1-(2-Hydroxy-ethyl)-2-(4-isopropyl-phenyl)-7-methoxy-1H-benzoimidazole-5-carbonitrile

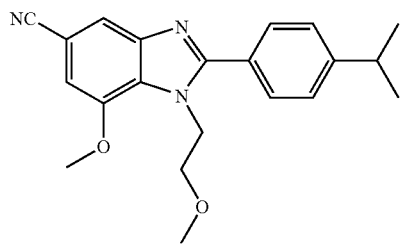

A solution of 1.42 g (3.52 mmol) of 5-Bromo-2-(4-isopropyl-phenyl)-7-methoxy-1-(2-methoxy-ethyl)-1H-benzoimidazole and 455 mg (3.87 mmol) zinc cyanide in 15 ml DMF is stirred under argon for 10 min at RT. Tetrakis(triphenylphosphine)palladium (214 mg, 0.176 mmol) is added and the reaction is heated to 180° C. for 90 min. After cooling to RT, ice/water is added and the reaction mixture is extracted with ethyl acetate (3×). The organic layer is washed with water, dried ($Na_2SO_4$) and concentrated in vacuo and the material is used without further purification.

Using the same synthetic method the following examples are prepared:

EXAMPLE 104

2-{2-[4-Bromo-2-(4-isopropyl-phenyl)-7-methoxy-1-(2-methoxy-ethyl)-1H-benzoimidazol-5-yl-methoxy]-phenyl}-ethanol

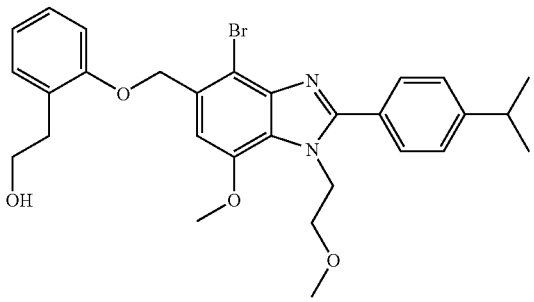

$R_t$=2.26 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 553 $(M+1)^+$ ($^{79}Br$), 555 $(M+1)^+$ ($^{81}Br$)

EXAMPLE 105

2-{2-[4-Bromo-2-(4-isopropyl-phenyl)-7-methoxy-1-(2-methoxy-ethyl)-1H-benzoimidazol-5-yl-methoxy]-phenoxy}-ethanol

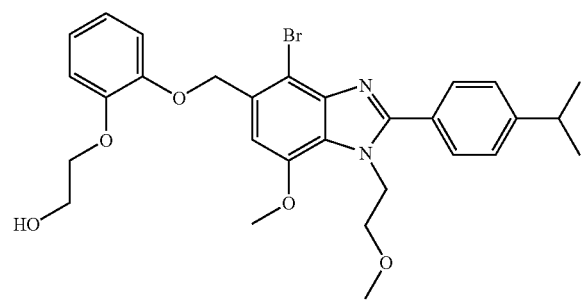

$R_t$=2.21 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 569 $(M+1)^+$ ($^{79}Br$), 571 $(M+1)^+$ ($^{81}Br$)

EXAMPLE 106

{2-[4-Bromo-2-(4-isopropyl-phenyl)-7-methoxy-1-(2-methoxy-ethyl)-1H-benzoimidazol-5-ylmethoxy]-phenyl}-methanol

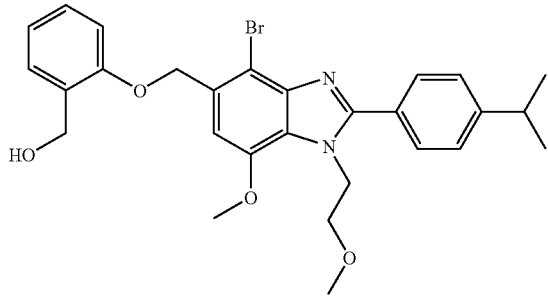

$R_t$=2.22 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 539 (M+1)$^+$ ($^{79}Br$), 541 (M+1)$^+$ ($^{81}Br$)

EXAMPLE 107

N-{2-[4-Bromo-2-(4-isopropyl-phenyl)-7-methoxy-1-(2-methoxy-ethyl)-1H-benzoimidazol-5-yl-methoxy]-phenyl}-acetamide

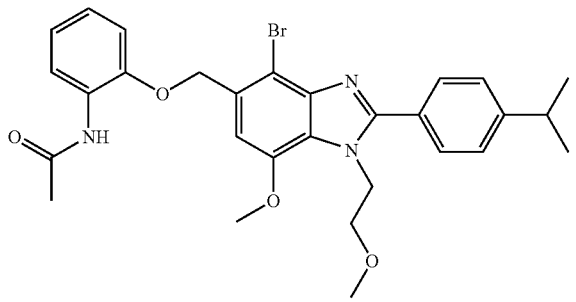

$R_t$=2.24 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 566 (M+1)$^+$ ($^{79}Br$), 568 (M+1)$^+$ ($^{81}Br$)

EXAMPLE 108

2-[4-Bromo-2-(4-isopropyl-phenyl)-7-methoxy-1-(2-methoxy-ethyl)-1H-benzoimidazol-5-ylmethoxy]-benzamide

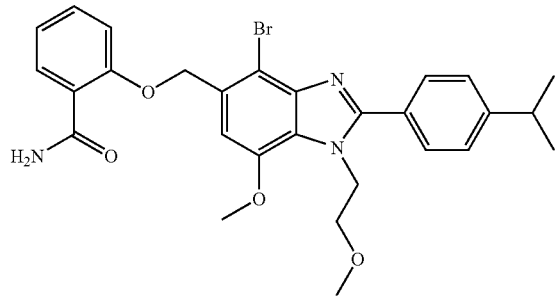

$R_t$=2.17 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 552 (M+1)$^+$ ($^{79}Br$), 554 (M+1)$^+$ ($^{81}Br$)

EXAMPLE 109

2-[4-Bromo-2-(4-isopropyl-phenyl)-7-methoxy-1-(2-methoxy-ethyl)-1H-benzoimidazol-5-ylmethoxy]-benzenesulfonamide

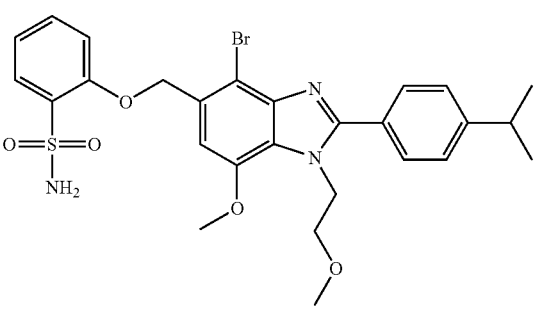

$R_t$=2.20 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 588 (M+1)$^+$ ($^{79}Br$), 590 (M+1)$^+$ ($^{81}Br$)

EXAMPLE 110

2-[4-Bromo-2-(4-isopropyl-phenyl)-7-methoxy-1-(2-methoxy-ethyl)-1H-benzoimidazol-5-ylmethoxy]-phenylamine

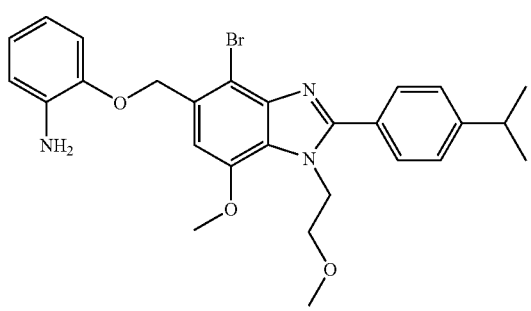

$R_t$=1.98 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 524 (M+1)$^+$ ($^{79}Br$), 526 (M+1)$^+$ ($^{81}Br$)

EXAMPLE 111

1-{2-[4-Bromo-2-(4-isopropyl-phenyl)-7-methoxy-1-(2-methoxy-ethyl)-1H-benzoimidazol-5-yl-methoxy]-phenyl}-ethanone

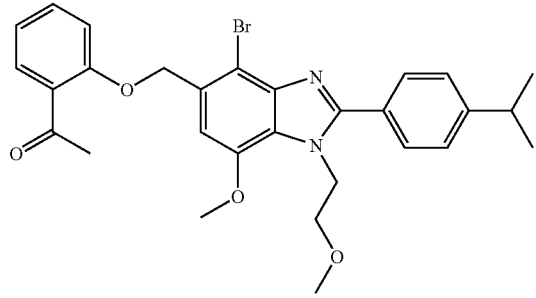

$R_t$=2.35 min (Waters Symmetry C8, 2.1×50 mm, detection 210-250 nM, 10% to 95% CH$_3$CN in H$_2$O in 2 min+0.05% TFA, flow rate 1.0 ml/min)
MS: 551 (M+1)$^+$ ($^{79}$Br), 553 (M+1)$^+$ ($^{81}$Br)

EXAMPLE 112

2-[4-Bromo-2-(4-isopropyl-phenyl)-7-methoxy-1-(2-methoxy-ethyl)-1H-benzoimidazol-5-ylmethoxy]-phenol

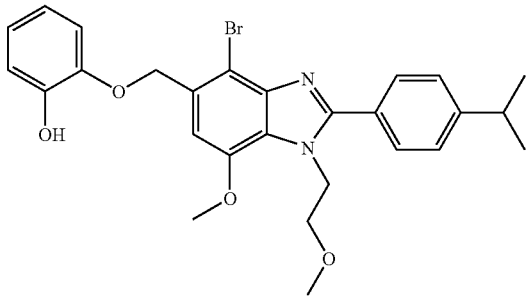

$R_t$=2.28 min (Waters Symmetry C8, 2.1×50 mm, detection 210-250 nM, 10% to 95% CH$_3$CN in H$_2$O in 2 min+0.05% TFA, flow rate 1.0 ml/min)
MS: 525 (M+1)$^+$ ($^{79}$Br), 527 (M+1)$^+$ ($^{81}$Br)

EXAMPLE 113

2-[4-Bromo-2-(4-isopropyl-phenyl)-7-methoxy-1-(2-methoxy-ethyl)-1H-benzoimidazol-5-ylmethoxy]-pyridin-3-ol

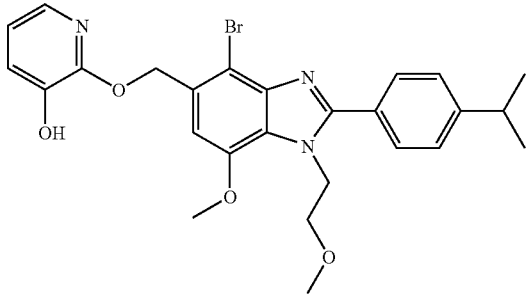

$R_t$=2.01 min (Waters Symmetry C8, 2.1×50 mm, detection 210-250 nM, 10% to 95% CH$_3$CN in H$_2$O in 2 min+0.05% TFA, flow rate 11.0 ml/min)
MS: 526 (M+1)$^+$ ($^{79}$Br), 528 (M+1)$^+$ ($^{81}$Br)

EXAMPLE 114

4-Bromo-2-(4-isopropyl-phenyl)-7-methoxy-1-(2-methoxy-ethyl)-5-(pyridin-2-yloxymethyl)-1H-benzoimidazole

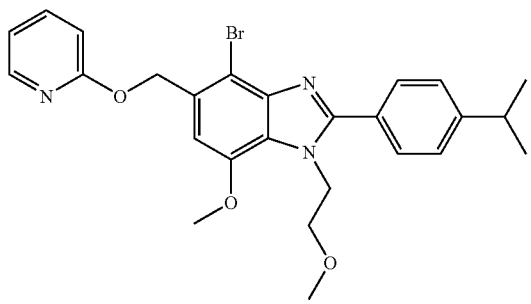

$R_t$=2.07 min (Waters Symmetry C8, 2.1×50 mm, detection 210-250 nM, 10% to 95% CH$_3$CN in H$_2$O in 2 min+0.05% TFA, flow rate 1.0 ml/min)
MS: 510 (M+1)$^+$ ($^{79}$Br), 512 (M+1)$^+$ ($^{81}$Br)

EXAMPLE 115

4-Bromo-2-(4-isopropyl-phenyl)-7-methoxy-1-(2-methoxy-ethyl)-5-(2-methoxy-phenoxymethyl)-1H-benzoimidazole

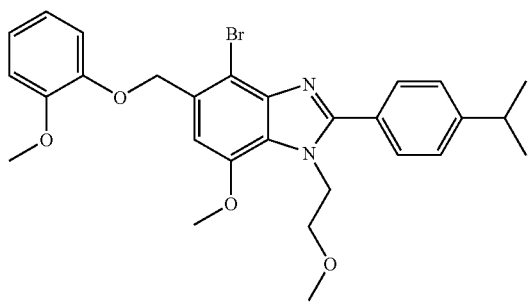

$R_t$=2.36 min (Waters Symmetry C8, 2.1×50 mm, detection 210-250 nM, 10% to 95% CH$_3$CN in H$_2$O in 2 min+0.05% TFA, flow rate 1.0 ml/min)
MS: 539 (M+1)$^+$ ($^{79}$Br), 541 (M+1)$^+$ ($^{81}$Br)

EXAMPLE 116

{3-[4-Bromo-2-(4-isopropyl-phenyl)-7-methoxy-1-(2-methoxy-ethyl)-1H-benzoimidazol-5-ylmethoxy]-2-methyl-phenyl}-methanol

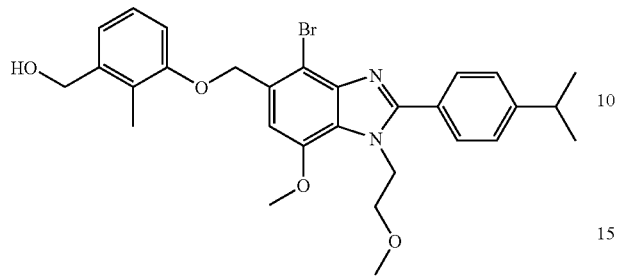

$R_t$=2.24 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 553 (M+1)$^+$ ($^{79}$Br), 555 (M+1)$^+$ ($^{81}$Br)

EXAMPLE 117

4-Bromo-2-(4-isopropyl-phenyl)-7-methoxy-1-(2-methoxy-ethyl)-5-(pyridin-3-yloxymethyl)-1H-benzoimidazole

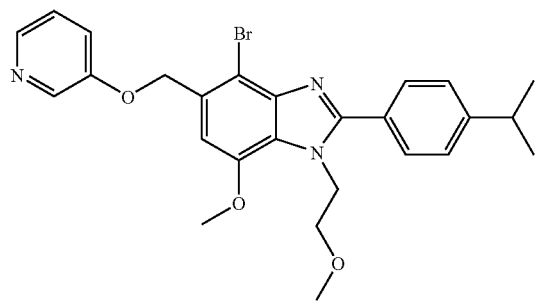

$R_t$=1.95 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 510 (M+1)$^+$ ($^{79}$Br), 512 (M+1)$^+$ ($^{81}$Br)

EXAMPLE 118

4-Bromo-2-(4-isopropyl-phenyl)-5-(2-methanesulfonyl-phenoxymethyl)-7-m ethoxy-1-(2-methoxy-ethyl)-1H-benzoimidazole

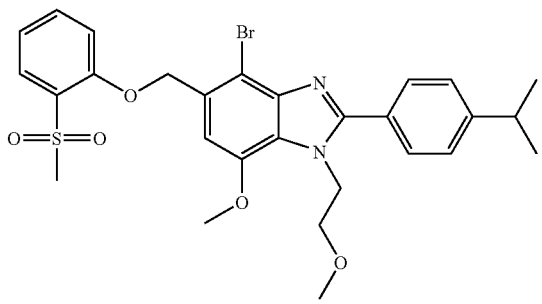

$R_t$=2.28 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 587 (M+1)$^+$ ($^{79}$Br), 589 (M+1)$^+$ ($^{81}$Br)

EXAMPLE 119

2-{3-[4-Bromo-2-(4-isopropyl-phenyl)-7-methoxy-1-(2-methoxy-ethyl)-1H-benzoimidazol-5-ylmethoxy]-phenoxy}-ethanol

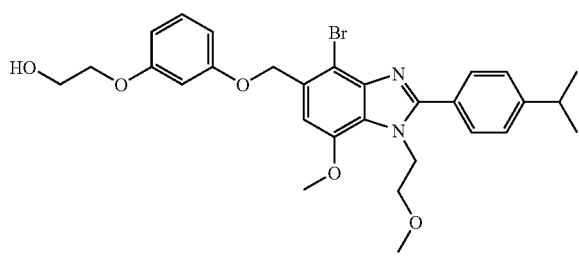

$R_t$=2.18 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 569 (M+1)$^+$ ($^{79}$Br), 571 (M+1)$^+$ ($^{81}$Br)

EXAMPLE 120

2-{2-[4-Bromo-2-(4-isopropyl-phenyl)-7-methoxy-1-(2-methoxy-ethyl)-1H-benzoimidazol-5-ylmethoxy]-phenyl}-acetamide

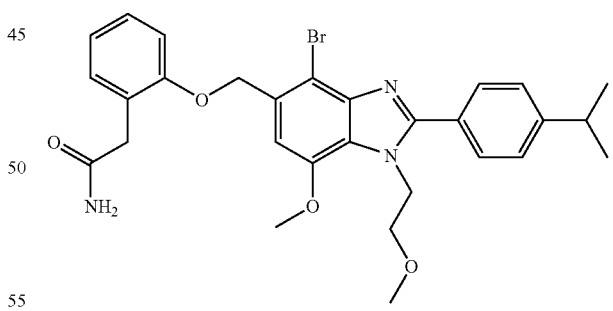

$R_t$=2.14 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 566 (M+1)$^+$ ($^{79}$Br), 568 (M+1)$^+$ ($^{81}$Br)

Using the same method by using 5-bromomethyl-2-(4-isopropyl-phenyl)-7-methoxy-1-(2-methoxy-ethyl)-4-trifluoromethyl-1H-benzoimidazole (see example 136) instead of methanesulfonic acid 4-bromo-2-(4-isopropyl-phenyl)-7-methoxy-1-(2-methoxy-ethyl)-1H-benzoimidazol-5-ylmethyl ester the following compounds are prepared:

EXAMPLE 121

2-{2-[2-(4-Isopropyl-phenyl)-7-methoxy-1-(2-methoxy-ethyl)-4-trifluoromethyl-1H-benzoimidazol-5-ylmethoxy]-phenoxy}-ethanol

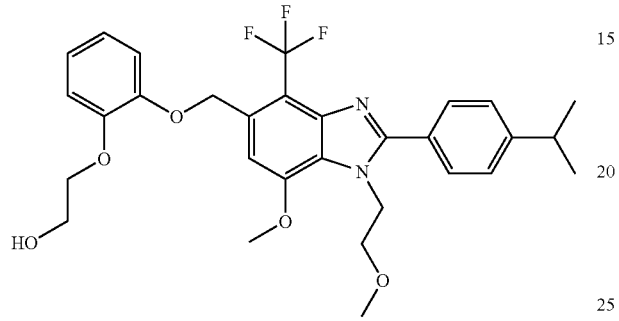

$R_t$=2.14 min (Waters Symmetry C8, 2.1×50 mm, detection 210-250 nM, 10% to 95% CH$_3$CN in H$_2$O in 2 min+0.05% TFA, flow rate 1.0 ml/min)

MS: 559 (M+1)$^+$

EXAMPLE 122

2-{2-[2-(4-isopropyl-phenyl)-7-methoxy-1-(2-methoxy-ethyl)-4-trifluoromethyl-1H-benzoimidazol-5-ylmethoxy]-phenyl}-ethanol

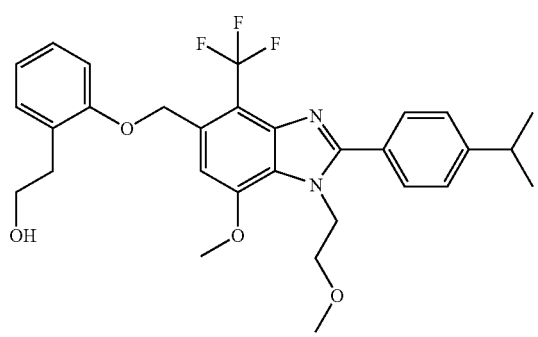

$R_t$=2.35 min (Waters Symmetry C8, 2.1×50 mm, detection 210-250 nM, 10% to 95% CH$_3$CN in H$_2$O in 2 min+0.05% TFA, flow rate 1.0 ml/min)

MS: 543 (M+1)$^+$

EXAMPLE 123

[4-Bromo-2-(4-isopropyl-phenyl)-7-methoxy-1-(2-methoxy-ethyl)-1H-benzoimidazol-5-ylmethyl]-phenyl-amine

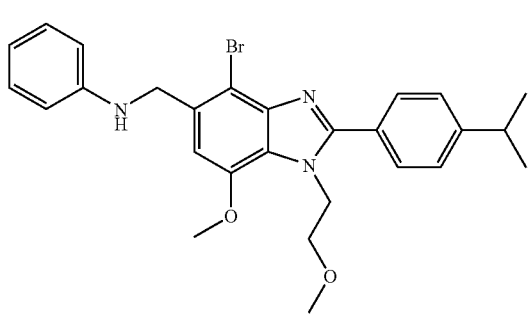

To a solution of 20 mg (0.039 mmol) of methanesulfonic acid 4-bromo-2-(4-isopropyl-phenyl)-7-methoxy-1-(2-methoxy-ethyl)-1H-benzoimidazol-5-ylmethyl ester in DMF is added aniline (excess) and the reaction is stirred for 1 h at 60° C. The reaction mixture is extracted with sat. NaHCO$_3$/water. The organic layer is evaporated and the residue is purified via reversed phase RP18-chromatographie to give 3.3 mg of the title compound.

$R_t$=2.26 min (Waters Symmetry C8, 2.1×50 mm, detection 210-250 nM, 10% to 95% CH$_3$CN in H$_2$O in 2 min+0.05% TFA, flow rate 1.0 ml/min)

MS: 508 (M+1)$^+$ ($^{79}$Br), 510 (M+1)$^+$ ($^{81}$Br)

Using the same synthetic method the following examples are prepared:

EXAMPLE 124

[4-Bromo-2-(4-isopropyl-phenyl)-7-methoxy-1-(2-methoxy-ethyl)-1H-benzoimidazol-5-ylmethyl]-(2-methanesulfonyl-phenyl)-amine

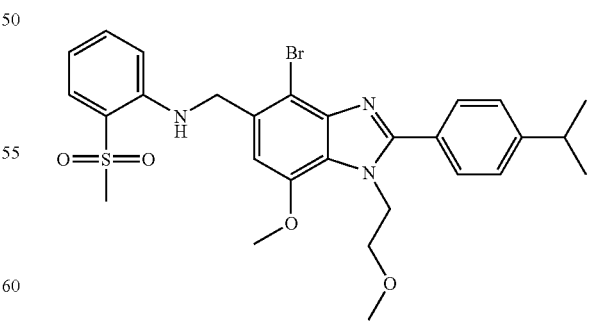

$R_t$=2.29 min (Waters Symmetry C8, 2.1×50 mm, detection 210-250 nM, 10% to 95% CH$_3$CN in H$_2$O in 2 min+0.05% TFA, flow rate 1.0 ml/min)

MS: 586 (M+1)$^+$ ($^{79}$Br), 588 (M+1)$^+$ ($^{81}$Br)

EXAMPLE 125

[4-Bromo-2-(4-isopropyl-phenyl)-7-methoxy-1-(2-methoxy-ethyl)-1H-benzoimidazol-5-ylmethyl]-[2-(2-methanesulfonyl-ethyl)-phenyl]-amine

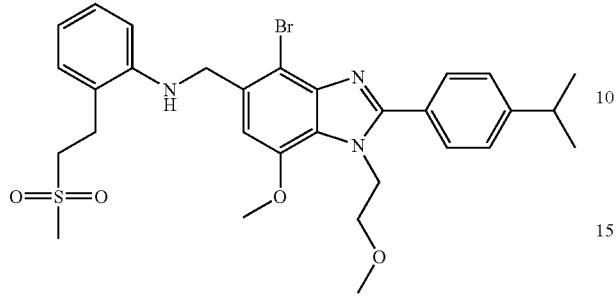

$R_t$=2.23 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 614 (M+1)$^+$ ($^{79}$Br), 616 (M+1)$^+$ ($^{81}$Br)

EXAMPLE 126

2-(2-{[4-Bromo-2-(4-isopropyl-phenyl)-7-methoxy-1-(2-methoxy-ethyl)-1H-benzoimidazol-5-ylmethyl]-amino}-phenyl)-acetamide

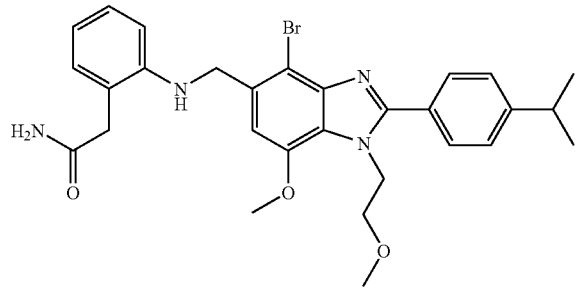

$R_t$=2.10 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 565 (M+1)$^+$ ($^{79}$Br), 567 (M+1)$^+$ ($^{81}$Br)

EXAMPLE 127

2-{[4-Bromo-2-(4-isopropyl-phenyl)-7-methoxy-1-(2-methoxy-ethyl)-1H-benzoimidazol-5-ylmethyl]-amino}-benzenesulfonic Acid

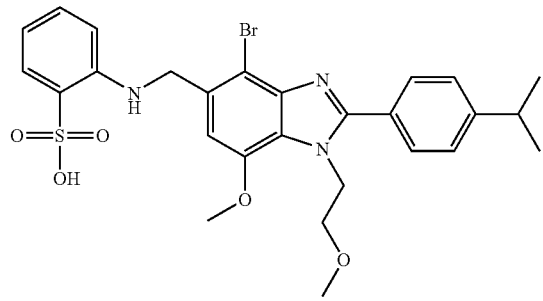

$R_t$=2.09 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 586 (M−1)$^-$ ($^{79}$Br), 588 (M−1)$^-$ ($^{81}$Br)

EXAMPLE 128

[4-Bromo-2-(4-isopropyl-phenyl)-7-methoxy-1-(2-methoxy-ethyl)-1H-benzoimidazol-5-ylmethyl]-(2-fluoro-phenyl)-amine

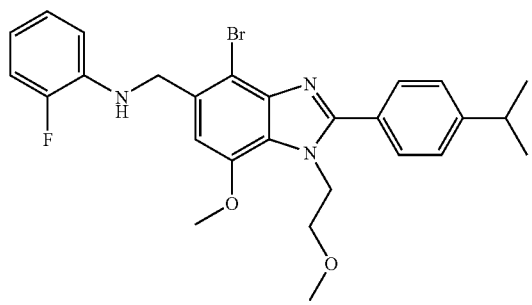

$R_t$=2.35 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 526 (M+1)$^+$ ($^{79}$Br), 528 (M+1)$^+$ ($^{81}$Br)

EXAMPLE 129

[4-Bromo-2-(4-isopropyl-phenyl)-7-methoxy-1-(2-methoxy-ethyl)-1H-benzoimidazol-5-ylmethyl]-pyridin-2-yl-amine

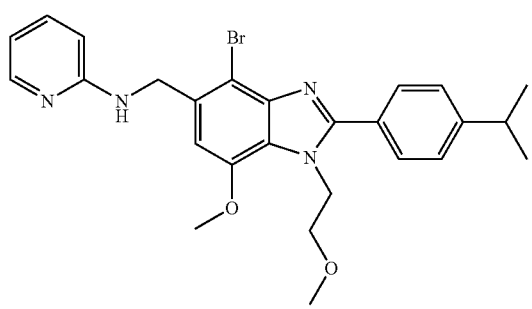

$R_t$=1.91 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 509 (M+1)$^+$ ($^{79}$Br), 511 (M+1)$^+$ ($^{81}$Br)

EXAMPLE 130

2-{[4-Bromo-2-(4-isopropyl-phenyl)-7-methoxy-1-(2-methoxy-ethyl)-1H-benzoimidazol-5-ylmethyl]-amino}-benzoic Acid Methyl Ester

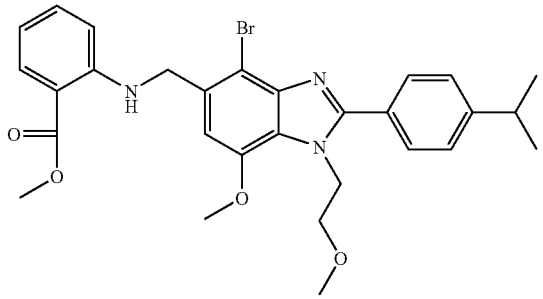

$R_t$=2.44 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 566 (M+1)$^+$ ($^{79}Br$), 568 (M+1)$^+$ ($^{81}Br$)

EXAMPLE 131

[4-Bromo-2-(4-isopropyl-phenyl)-7-methoxy-1-(2-methoxy-ethyl)-1H-benzoimidazol-5-ylmethyl]-pyridin-3-yl-amine

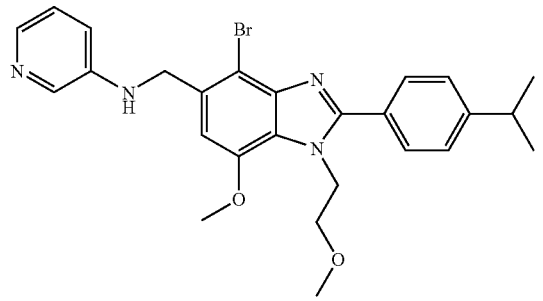

$R_t$=1.89 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 509 (M+1)$^+$ ($^{79}Br$), 511 (M+1)$^+$ ($^{81}Br$)

EXAMPLE 132

[4-Bromo-2-(4-isopropyl-phenyl)-7-methoxy-1-(2-methoxy-ethyl)-1H-benzoimidazol-5-ylmethyl]-methyl-phenyl-amine

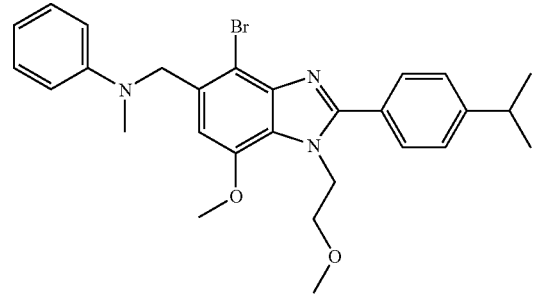

$R_t$=2.34 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 522 (M+1)$^+$ ($^{79}Br$), 524 (M+1)$^+$ ($^{81}Br$)

EXAMPLE 133

[4-Bromo-2-(4-isopropyl-phenyl)-7-methoxy-1-(2-methoxy-ethyl)-1H-benzoimidazol-5-ylmethyl]-(3-methanesulfonyl-phenyl)-amine

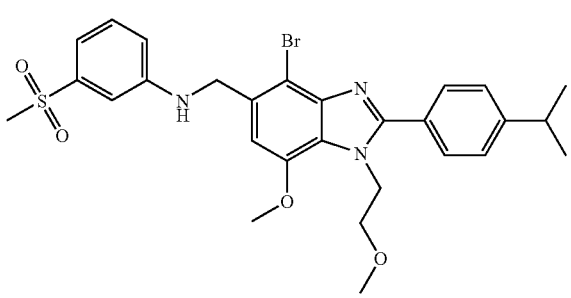

$R_t$=2.18 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 586 (M+1)$^+$ ($^{79}Br$), 588 (M+1)$^+$ ($^{81}Br$)

Using the same method by using 5-bromomethyl-2-(4-isopropyl-phenyl)-7-methoxy-1-(2-methoxy-ethyl)-4-trifluoromethyl-1H-benzoimidazole instead of methanesulfonic acid 4-bromo-2-(4-isopropyl-phenyl)-7-methoxy-1-(2-methoxy-ethyl)-1H-benzoimidazol-5-ylmethyl ester the following compound are prepared:

EXAMPLE 134

2-(2-{[2-(4-isopropyl-phenyl)-7-methoxy-1-(2-methoxy-ethyl)-4-trifluoromethyl-1H-benzoimidazol-5-ylmethyl]-amino}-phenyl)-acetamide

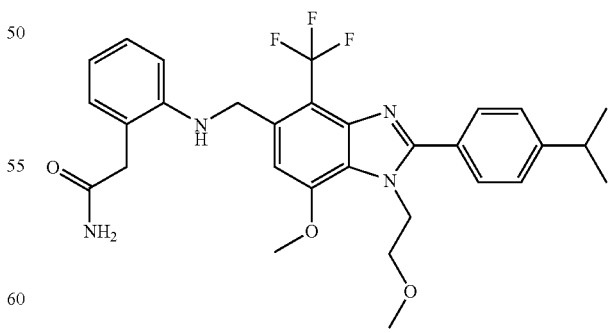

$R_t$=2.19 min (Waters Symmetry C8, 2.1×50 mm, detection 210-250 nM, 10% to 95% $CH_3CN$ in $H_2O$ in 2 min+0.05% TFA, flow rate 1.0 ml/min)
MS: 555 (M+1)$^+$

EXAMPLE 135

[2-(4-Isopropyl-phenyl)-7-methoxy-1-(2-methoxy-ethyl)-4-trifluoromethyl-1H-benzoimidazol-5-ylmethyl]-(2-methanesulfonyl-phenyl)-amine

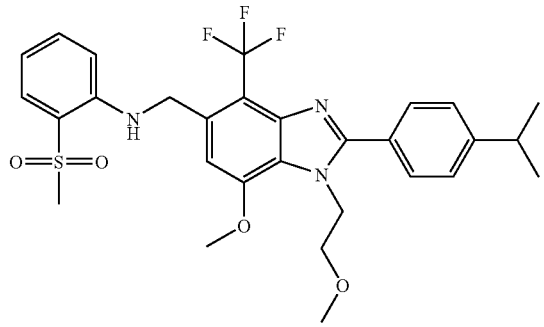

$R_t$=2.36 min (Waters Symmetry C8, 2.1×5 mm, detection 210-250 nM, 10% to 95% CH$_3$CN in H$_2$O in 2 min+0.05% TFA, flow rate 1.0 ml/min)

MS: 576 (M+1)$^+$

EXAMPLE 136

[2-(4-Isopropyl-phenyl)-7-methoxy-1-(2-methoxy-ethyl)-4-trifluoromethyl-1H-benzoimidazol-5-ylmethyl]-[2-(2-methanesulfonyl-ethyl)-phenyl]-amine

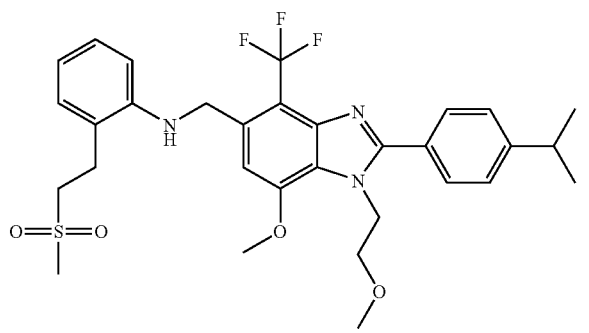

$R_t$=2.32 min (Waters Symmetry C8, 2.1×50 mm, detection 210-250 nM, 10% to 95% CH$_3$CN in H$_2$O in 2 min+0.05% TFA, flow rate 1.0 ml/min)

MS: 604 (M+1)$^+$

Preparation of the Starting Material:

a) 5-Bromomethyl-2-(4-isopropyl-phenyl)-7-methoxy-1-(2-methoxy-ethyl)-4-trifluoromethyl-1H-benzoimidazole

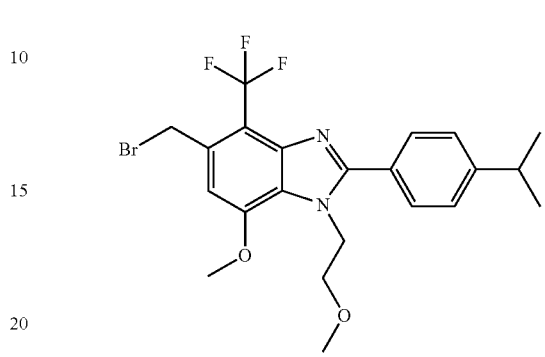

To a solution of 655 mg (1.52 mmol) [2-(4-isopropyl-phenyl)-7-methoxy-1-(2-methoxy-ethyl)-4-trifluoromethyl-1H-benzoimidazol-5-yl]-methanol in 10 ml THF, 604 mg (2.28 mmol) triphenylphosphine and 764 mg (2.28 mmol) carbon tetrabromide are added at 0° C. The mixture is stirred at 0° C. for 10 min and 30 min at room temperature. Then the reaction mixture is poured on water and extracted (3×) with ethyl acetate. The combined organic layers are washed with water (2×) and brine, dried over MgSO$_4$, filtered and concentrated in vacuo. The residue is purified by flash-chromatography on silica gel (hexane:EtOAc=2:1->1:1) to afford 660 mg of the title compound as a colorless crystalline solid.

b) [2-(4-isopropyl-phenyl)-7-methoxy-1-(2-methoxy-ethyl)-4-trifluoromethyl-1H-benzoimidazol-5-yl]-methanol

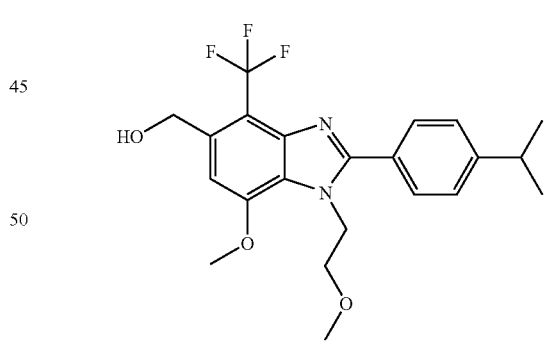

To a solution of 710 mg (1.69 mmol) 2-(4-isopropyl-phenyl)-7-methoxy-1-(2-methoxy-ethyl)-4-trifluoromethyl-1H-benzoimidazole-5-carbaldehyde (example 54c) in 5 ml ethanol, 128 mg (3.38 mmol) NaBH$_4$ are added at 0° C. The mixture is stirred for 30 min at room temperature. Then the reaction mixture is poured on water and extracted (3×) with ethyl acetate. The combined organic layers are washed with water (2×) and brine, dried over MgSO$_4$, filtered and concentrated in vacuo. The residue is crystallized from hexane/EtOAc to afford 655 mg of the title compound as a colorless crystalline solid.

Using the synthetic methods described above the following compounds are also be prepared:

EXAMPLE 137

1-[4-Bromo-2-(4-isopropyl-phenyl)-7-methoxy-1-(2-methoxy-ethyl)-1H-benzoimidazol-5-ylmethyl]-1H-imidazole-2-carboxylic Acid Methyl Ester

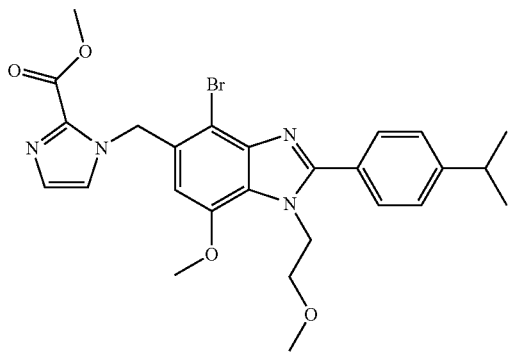

$R_t$=2.05 min (Waters Symmetry C8, 2.1×50 mm, detection 210-250 nM, 10% to 95% CH$_3$CN in H$_2$O in 2 min+0.05% TFA, flow rate 1.0 ml/min)

MS: 541 (M+1)$^+$ ($^{79}$Br), 543 (M+1)$^+$ ($^{81}$Br)

EXAMPLE 138

1-[4-Bromo-2-(4-isopropyl-phenyl)-7-methoxy-1-(2-methoxy-ethyl)-1H-benzoimidazol-5-ylmethyl]-1H-imidazole-2-carboxylic Acid Dimethylamide

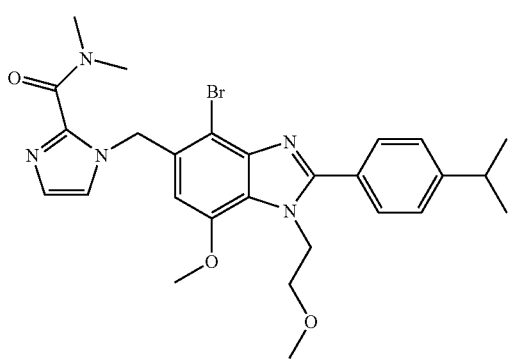

$R_t$=1.98 min (Waters Symmetry C8, 2.1×50 mm, detection 210-250 nM, 10% to 95% CH$_3$CN in H$_2$O in 2 min+0.05% TFA, flow rate 1.0 ml/min)

MS: 554 (M+1)$^+$ ($^{79}$Br), 556 (M+1)$^+$ ($^{81}$Br)

EXAMPLE 139

1-{1-[4-Bromo-2-(4-isopropyl-phenyl)-7-methoxy-1-(2-methoxy-ethyl)-1H-benzoimidazol-5-ylmethyl]-1H-imidazol-2-yl}-ethanone

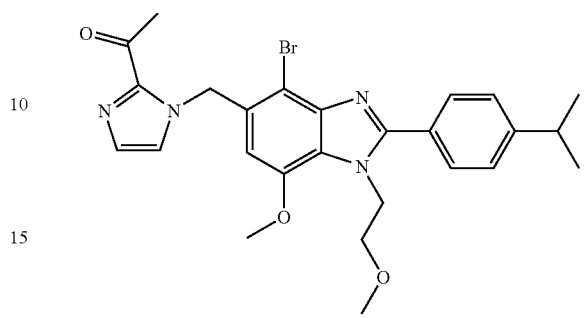

$R_t$=2.12 min (Waters Symmetry C8, 2.1×50 mm, detection 210-250 nM, 10% to 95% CH$_3$CN in H$_2$O in 2 min+0.05% TFA, flow rate 1.0 ml/min)

MS: 525 (M+1)$^+$ ($^{79}$Br), 527 (M+1)$^+$ ($^{81}$Br)

EXAMPLE 140

1-[4-Bromo-2-(4-isopropyl-phenyl)-7-methoxy-1-(2-methoxy-ethyl)-1H-benzoimidazol-5-ylmethyl]-1H-indole-2,3-dione

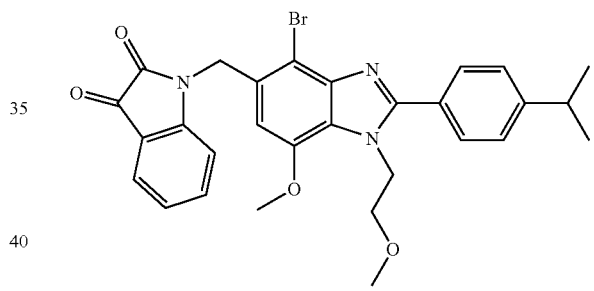

$R_t$=2.29 min (Waters Symmetry C8, 2.1×50 mm, detection 210-250 nM, 10% to 95% CH$_3$CN in H$_2$O in 2 min+0.05% TFA, flow rate 1.0 ml/min)

MS: 562 (M+1)$^+$ ($^{79}$Br), 564 (M+1)$^+$ ($^{81}$Br)

EXAMPLE 141

4-Bromo-2-(4-isopropyl-phenyl)-7-methoxy-1-(2-methoxy-ethyl)-5-oxazol-2-ylmethyl-1H-benzoimidazole

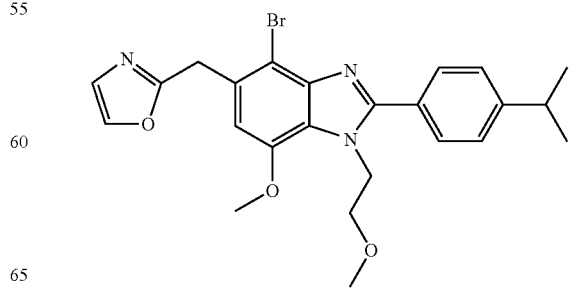

$R_t$=1.85 min (Waters Symmetry C8, 2.1×50 mm, detection 210-250 nM, 10% to 95% CH$_3$CN in H$_2$O in 2 min+0.05% TFA, flow rate 1.0 ml/min)

MS: 484 (M+1)$^+$ ($^{79}$Br), 486 (M+1)$^+$ ($^{81}$Br)

EXAMPLE 142

1-[4-Bromo-2-(4-isopropyl-phenyl)-7-methoxy-1-(2-methoxy-ethyl)-1H-benzoimidazol-5-ylmethyl]-1H-imidazole-2-carbonitrile

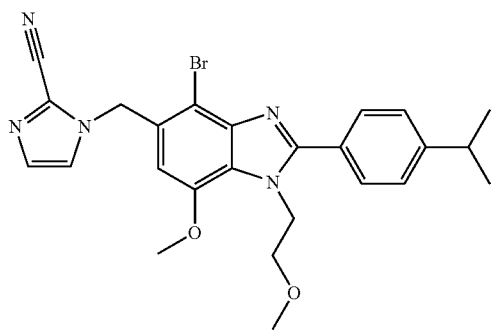

$R_t$=2.24 min (Waters Symmetry C8, 2.1×50 mm, detection 210-250 nM, 10% to 95% CH$_3$CN in H$_2$O in 2 min+0.05% TFA, flow rate 11.0 ml/min)

MS: 508 (M+1)$^+$ ($^{79}$Br), 510 (M+1)$^+$ ($^{81}$Br)

EXAMPLE 143

1-[4-Bromo-2-(4-isopropyl-phenyl)-7-methoxy-1-(2-methoxy-ethyl)-1H-benzoimidazol-5-ylmethyl]-1H-imidazole-2-carboxylic Acid Methylamide

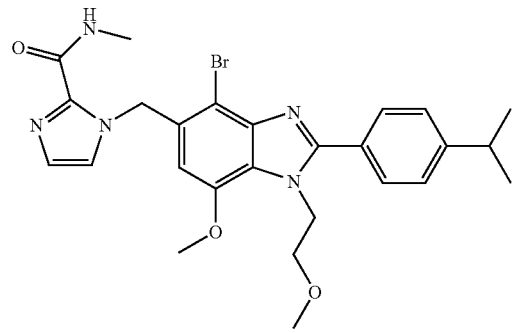

$R_t$=1.79 min (Waters Symmetry C8, 2.1×50 mm, detection 210-250 nM, 10% to 95% CH$_3$CN in H$_2$O in 2 min+0.05% TFA, flow rate 1.0 ml/min)

MS: 540 (M+1)$^+$ ($^{79}$Br), 542 (M+1)$^+$ ($^{81}$Br)

EXAMPLE 144

2-(4-Isopropyl-phenyl)-7-methoxy-1-(2-methoxy-ethyl)-5-bromo-4-trifluoromethyl-1H-benzoimidazole

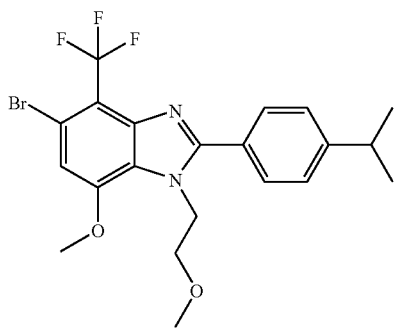

$R_t$=2.50 min (Waters Symmetry C8, 2.1×50 mm, detection 210-250 nM, 10% to 95% CH$_3$CN in H$_2$O in 2 min+0.05% TFA, flow rate 1.0 ml/min)

MS: 471 (M+1)$^+$ ($^{79}$Br), 473 (M+1)$^+$ ($^{81}$Br)

EXAMPLE 145

[2-(4-Isopropyl-phenyl)-7-methoxy-1-(2-methoxy-ethyl)-4-trifluoromethyl-1H benzoimidazol-5-ylmethyl]-phenyl-amine

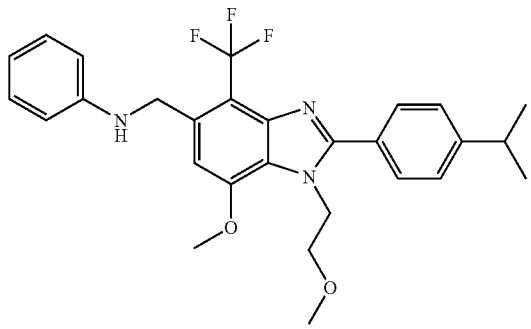

$R_t$=2.35 min (Waters Symmetry C8, 2.1×50 mm, detection 210-250 nM, 10% to 95% CH$_3$CN in H$_2$O in 2 min+0.05% TFA, flow rate 1.0 ml/min)

MS: 498 (M+1)$^+$

EXAMPLE 146

[2-(4-Isopropyl-phenyl)-7-methoxy-1-(2-methoxy-ethyl)-4-trifluoromethyl-1H-benzoimidazol-5-ylmethyl]-pyridin-2-yl-amine

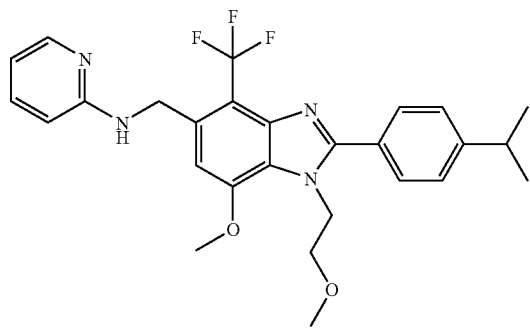

$R_t$=1.97 min (Waters Symmetry C8, 2.1×50 mm, detection 210-250 nM, 10% to 95% CH$_3$CN in H$_2$O in 2 min+0.05% TFA, flow rate 1.0 ml/min)

MS: 499 (M+1)$^+$

EXAMPLE 147

2-{[2-(4-Isopropyl-phenyl)-7-methoxy-1-(2-methoxy-ethyl)-4-trifluoromethyl-1H-benzoimidazol-5-ylmethyl]-amino}-benzenesulfonamide

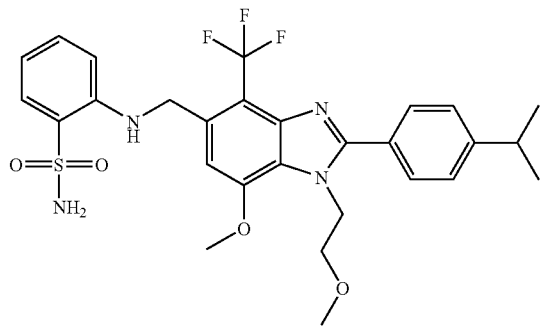

$R_t$=2.17 min (Waters Symmetry C8, 2.1×50 mm, detection 210-250 nM, 10% to 95% CH$_3$CN in H$_2$O in 2 min+0.05% TFA, flow rate 1.0 ml/min)

MS: 577 (M+1)$^+$

EXAMPLE 148

2-(4-Isopropyl-phenyl)-7-methoxy-1-(2-methoxy-ethyl)-5-phenoxymethyl-4-trifluoromethyl-1H-benzoimidazole

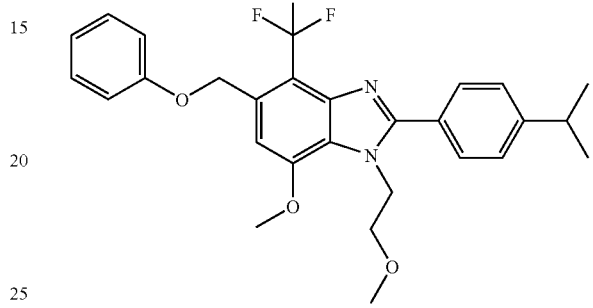

$R_t$=2.48 min (Waters Symmetry C8, 2.1×50 mm, detection 210-250 nM, 10% to 95% CH$_3$CN in H$_2$O in 2 min+0.05% TFA, flow rate 1.0 ml/min)

MS: 499 (M+1)$^+$

EXAMPLE 149

2-(4-Isopropyl-phenyl)-7-methoxy-1-(2-methoxy-ethyl)-5-(pyridin-2-yloxymethyl)-4-trifluoromethyl-1H-benzoimidazole

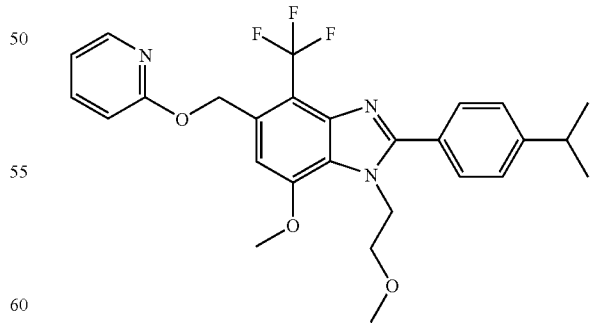

$R_t$=2.14 min (Waters Symmetry C8, 2.1×50 mm, detection 210-250 nM, 10% to 95% CH$_3$CN in H$_2$O in 2 min+0.05% TFA, flow rate 1.0 ml/min)

MS: 500 (M+1)$^+$

EXAMPLE 150

2-[2-(4-Isopropyl-phenyl)-7-methoxy-1-(2-methoxy-ethyl)-4-trifluoromethyl-1H-benzoimidazol-5-yl-methoxy]-benzenesulfonamide

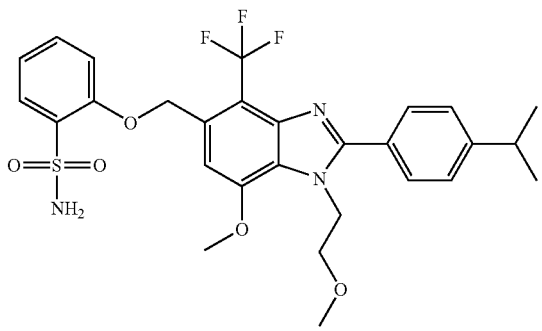

$R_t$=2.29 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 578 $(M+1)^+$

EXAMPLE 151

4-Bromo-2-(4-isopropyl-phenyl)-7-methoxy-1-(2-methoxy-ethyl)-5-(pyridin-2-yloxy)-1H-benzoimidazole

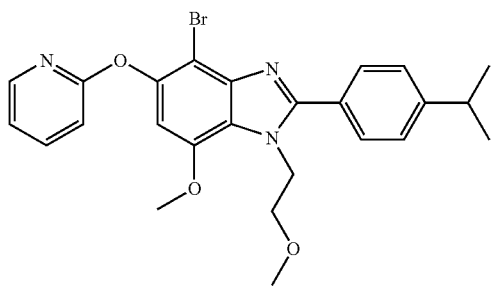

$R_t$=2.24 min (Waters Symmetry C8, 2.1×50 mm, detection 210-250 nM, 10% to 95% $CH_3CN$ in $H_2O$ in 2 min+0.05% TFA, flow rate 1.0 ml/min)

MS: 496 $(M+1)^+$ ($^{79}Br$), 498 $(M+1)^+$ ($^{81}Br$)

The Agents of the Invention, as defined above, e.g., of formula (I), particularly as exemplified, in free or pharmaceutically acceptable acid addition salt form, exhibit pharmacological activity and are useful as pharmaceuticals, e.g. for therapy, in the treatment of diseases and conditions as hereinafter set forth.

Inositol Phosphate Formation Assay:

To determine antagonistic activity at the human parathyroid calcium-sensing receptor (PcaR), compounds are tested in functional assays measuring the inhibition of calcium-induced inositol phosphate formation in CCL39 fibroblasts stably transfected with human PcaR.

Cells are seeded into 24 well plates and grown to confluence. Cultures are then labelled with [$^3$H]inositol (74 Mbq/ml) in serum-free medium for 24 h. After labelling, cells are washed once with a modified Hepes-buffered salt solution (mHBS: 130 mM NaCl, 5.4 mM KCl, 0.5 mM $CaCl_2$, 0.9 mM $MgSO_4$, 10 mM glucose, 20 mM HEPES, pH 7.4) and incubated with mHBS at 37° C. in the presence of 20 mM LiCl to block inositol monophosphatase activity. Test compounds are added 3 minutes before stimulating PcaR with 5.5 mM calcium and incubations continued for further 20 min. Thereafter, cells are extracted with 10 mM ice-cold formic acid and inositol phosphates formed are determined using anion exchange chromatography and liquid scintillation counting.

Assay for Intracellular Free Calcium:

An alternative method to determine antagonism at the PcaR consists in measuring the inhibition of intracellular calcium transients stimulated by extracellular calcium. CCL39 fibroblasts stably transfected with human PcaR are seeded at 40,000 cells/well into 96-well Viewplates and incubated for 24 hours. Medium is then removed and replaced with fresh medium containing 2 μM Fluo-3 AM (Molecular Probes, Leiden, The Netherlands), In routine experiments, cells are incubated at 37° C., 5% $CO_2$ for 1 h. Afterwards, plates are washed twice with mHBS and wells are refilled with 100 μl mHBS containing the test compounds. Incubation is continued at room temperature for 15 minutes. To record changes of intracellular free calcium, plates are transferred to fluorescence-imaging plate reader (Molecular Devices, Sunnyvale, Calif., USA). A baseline consisting in 5 measurements of 0.4 seconds each (laser excitation 488 nm) is recorded. Cells are then stimulated with calcium (2.5 mM final), and fluorescence changes recorded over a period of 3 minutes.

When measured in the above assays, Agents of the Invention typically have $IC_{50}$s in the range from about 1000 nM down to about 10 nM or less.

It is now well established that controlled treatment of patients with parathyroid hormone (PTH) and analogues and fragments thereof can have a pronounced anabolic effect on bone formation. Thus compounds which promote PTH release, such as the Agents of the Invention may be used for preventing or treating conditions of bone which are associated with increased calcium depletion or resorption or in which stimulation of bone formation and calcium fixation in the bone is desirable.

Agents of the Invention are accordingly indicated for preventing or treating all bone conditions which are associated with increased calcium depletion or resorption or in which stimulation of bone formation and calcium fixation in the bone is desirable, e.g. osteoporosis of various genesis (e.g. juvenile, menopausal, post-menopausal, post-traumatic, caused by old age or by cortico-steroid therapy or inactivity), fractures, osteopathy, including acute and chronic states associated with skeletal demineralisation, osteo-malacia, periodontal bone loss or bone loss due to arthritis or osteoarthritis or for treating hypoparathyroidism.

Further diseases and disorders which might be prevented or treated include e.g. seizures, stroke, head trauma, spinal cord injury, hypoxia-induced nerve cell damage such as in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, congestive heart failure; hypertension; gut motility disorders such as diarrhea, and spastic colon and dermatological disorders, e.g. in tissue healing, for example burns, ulcerations and wounds.

The Agents of the Invention are particularly indicated for preventing or treating osteoporosis of various genesis.

For all the above uses, an indicated daily dosage is in the range from about 0.03 to about 1000 mg, preferably, more preferably 0.03 to 30, yet more preferably 0.1 to 10 mg of a compound of the invention. Agents of the Invention may be administered twice a day or up to twice a week.

The Agents of the Invention may be administered in free form or in pharmaceutically acceptable salt form. Such salts may be prepared in conventional manner and exhibit the same order of activity as the free compounds. The present invention also provides a pharmaceutical composition comprising an Agent of the Invention in free base form or in pharmaceutically acceptable salt form in association with a pharmaceutically acceptable diluent or carrier. Such compositions may be formulated in conventional manner. The Agents of the Invention may be administered by any conventional route, for example parenterally e.g. in the form of injectable solutions or suspensions, enterally, e.g. orally, for example in the form of tablets or capsules or in a transdermal, nasal or a suppository form.

In accordance with the foregoing the present invention further provides:
a) an Agent of the Invention or a pharmaceutically acceptable salt thereof for use as a pharmaceutical;
b) a method for preventing or treating above mentioned disorders and diseases in a subject in need of such treatment, which method comprises administering to said subject an effective amount of an Agent of the Invention or a pharmaceutically acceptable salt thereof;
c) an Agent of the Invention or a pharmaceutically acceptable salt thereof for use in the preparation of a pharmaceutical composition e.g. for use in the method as in b) above.

According to a further embodiment of the invention, the Agents of the Invention may be employed as adjunct or adjuvant to other therapy, e.g. a therapy using a bone resorption inhibitor, for example as in osteoporosis therapy, in particular a therapy employing calcium, a calcitonin or an analogue or derivative thereof, e.g. salmon, eel or human calcitonin, a steroid hormone, e.g. an estrogen, a partial estrogen agonist or estrogen-gestageni combination, a SERM (Selective Estrogen Receptor Modulator) e.g. raloxifene, lasofoxifene, TSE-424, FC1271, Tibolone (Livial®), vitamin D or an analog thereof or PTH, a PTH fragment or a PTH derivative e.g. PTH (1-84), PTH (1-34), PTH (1-36), PTH (1-38), PTH (1-31)NH$_2$ or PTS 893.

When the Agents of the Invention are administered in conjunction with, e.g. as an adjuvant to bone resorption inhibition therapy, dosages for the co-administered inhibitor will of course vary depending on the type of inhibitor drug employed, e.g. whether it is a steroid or a calcitonin, on the condition to be treated, whether it is a curative or preventive therapy, on the regimen and so forth.

The invention claimed is:
1. A compound of formula (I') or a pharmaceutically acceptable salt thereof:

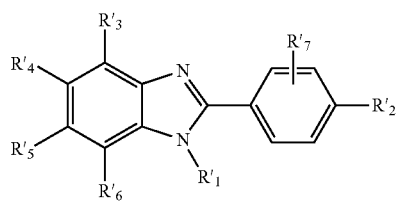

(I')

wherein
$R'_1$ is selected from the group consisting of $C_1$-$C_6$ alkyl, lower alkoxy-lower alkyl, lower thioalkyl-lower alkyl, cyclopropyl lower alkyl;

$R'_2$ is lower alkyl;
$R'_3$ is selected from the group consisting of halo, cyano, lower alkyl, lower alkoxy, lower thioalkyl, lower thioalkenyl, lower alkynyl, aryl and aryl-lower alkyl;
$R'_4$ is selected from the group consisting of H, halo, cyano, lower alkyl, aryl, aryl-lower alkyl, heteroaryl, heteroaryl-lower alkyl and the group having the formula $R'_8$—Z(CH$_2$)$_n$—;

wherein Z represents a direct bond or is selected from the group consisting of NH, CH$_2$, CO, SO, SO$_2$ or S;
wherein $R'_8$ is selected from the group consisting of aryl, pyrazolyl, thiazolyl, cyclobutyl, tetrazolyl, pyridyl, indazolyl, pyrazinyl, furanyl, isoxazolyl, pyrrolidinyl, benzimidazolyl, imidazolyl, oxazolyl;
and wherein n is 0, 1, 2 or 3;
$R'_5$ is H, halo, or lower alkyl;
$R'_6$ is lower alkoxy; and
$R'_7$ represents one or more substituents independently selected from the group consisting of H, halo, hydroxyl, lower alkyl, lower alkoxy, amino, cyano, and carbonyl.
2. A compound selected from:
4-Bromo-2-(4-isopropyl-phenyl)-7-methoxy-1-(2-methoxy-ethyl)-1H-benzoimidazole
4-Iodo-2-(4-isopropyl-phenyl)-7-methoxy-1-(2-methoxy-ethyl)-1H-benzoimidazole
4-Iodo-2-(4-isopropyl-phenyl)-7-methoxy-1-(2-methylsulfanyl-ethyl)-1H-benzoimidazole
4-Bromo-2-(4-isopropyl-phenyl)-7-methoxy-1-(2-methylsulfanyl-ethyl)-1H-benzoimidazole
4-Bromo-1-cyclopropylmethyl-2-(4-isopropyl-phenyl)-7-methoxy-1H-benzoimidazole
4-Bromo-1-propyl-2-(4-isopropyl-phenyl)-7-methoxy-1H-benzoimidazole
4-Bromo-1-butyl-2-(4-isopropyl-phenyl)-7-methoxy-1H-benzoimidazole
4-Bromo-1-ethyl-2-(4-isopropyl-phenyl)-7-methoxy-1H-benzoimidazole
{2-[4-Bromo-2-(4-isopropyl-phenyl)-7-methoxy-benzoimidazol-1-yl]ethyl}-dimethyl-amine
4-Chloro-2-(4-isopropyl-phenyl)-7-methoxy-1-(2-methoxy-ethyl)-1H-benzoimidazole
4-Ethynyl-2-(4-isopropyl-phenyl)-7-methoxy-1-(2-methoxy-ethyl)-1H-benzoimidazole
2-(4-Isopropyl-phenyl)-7-methoxy-1-(2-methoxy-ethyl)-4-phenyl-1H-benzoimidazole
3-[2-(4-Isopropyl-phenyl)-7-methoxy-1-(2-methoxy-ethyl)-1H-benzoimidazol-4-yl]-phenol
2-(4-Isopropyl-phenyl)-7-methoxy-4-[3-(2-methoxy-ethoxy)-phenyl]-1-(2-methoxy-ethyl)-1H-benzoimidazole
4-(3,5-Dimethoxy-phenyl)-2-(4-isopropyl-phenyl)-7-methoxy-1-(2-methoxy-ethyl)-1H-benzoimidazole
4-Methyl-2-(4-isopropyl-phenyl)-7-methoxy-1-(2-methoxy-ethyl)-1H-benzoimidazole
4-Ethyl-2-(4-isopropyl-phenyl)-7-methoxy-1-(2-methoxy-ethyl)-1H-benzoimidazole
4-Ethylsulfanyl-2-(4-isopropyl-phenyl)-7-methoxy-1-(2-methoxy-ethyl)-1H-benzoimidazole
4-Bromo-2-(4-cyclopropyl-phenyl)-7-methoxy-1-(2-methoxy-ethyl)-1H-benzoimidazole
4-Bromo-2-(4-cyclopropyl-phenyl)-7-methoxy-1-(2-methylsulfanyl-ethyl)-1H-benzoimidazole
4-Bromo-1-cyclopropylmethyl-2-(4-cyclopropyl-phenyl)-7-methoxy-1H-benzoimidazole
4, 5-Dibromo-2-(4-isopropyl-phenyl)-7-methoxy-1-(2-methoxy-ethyl)-1H-benzoimidazole 4,5-Dibromo-2-(4-cyclopropyl-phenyl)-7-methoxy-1-(2-methoxy-ethyl)-1H-benzoimidazole
4,5-Dibromo-2-(4-isopropyl-2-methoxy-phenyl)-7-methoxy-1-(2-methoxy-ethyl)-1H-benzoimidazole
4-Iodo-5-bromo-2-(4-isopropyl-phenyl)-7-methoxy-1-(2-methoxy-ethyl)-1H-benzoimidazole
5-Bromo-4-iodo-2-(4-isopropyl-2-methoxy-phenyl)-7-methoxy-1-(2-methoxy-ethyl)-1H-benzoimidazole
4-Bromo-2-(4-isopropyl-phenyl)-7-methoxy-1-(2-methoxy-ethyl)-5-trifluoromethyl-1H-benzoimidazole
4-Bromo-1-cyclopropylmethyl-2-(4-isopropyl-phenyl)-7-methoxy-5-trifluoromethyl-1H-benzoimidazole
4-Bromo-5-iodo-2-(4-isopropyl-phenyl)-7-methoxy-1-(2-methoxy-ethyl)-1H-benzoimidazole
5-Bromo-4-ethynyl-2-(4-isopropyl-phenyl)-7-methoxy-1-(2-methoxy-ethyl)-1H-benzoimidazole
4-Bromo-2-(4-isopropyl-phenyl)-7-methoxy-1-(2-methoxy-ethyl)-1H-benzoimidazole-5-carbonitrile
4-Bromo-5-fluoro-2-(4-isopropyl-phenyl)-7-methoxy-1-(2-methoxy-ethyl)-1H-benzoimidazole
5-Benzyl-4-bromo-2-(4-isopropyl-phenyl)-7-methoxy-1-(2-methoxy-ethyl)-1H-benzoimidazole
5-Benzyl-4-iodo-2-(4-isopropyl-phenyl)-7-methoxy-1-(2-methoxy-ethyl)-1H-benzoimidazole
5-Benzyl-4-ethynyl-2-(4-isopropyl-phenyl)-7-methoxy-1-(2-methoxy-ethyl)-1H-benzoimidazole
4-Ethynyl-2-(4-isopropyl-phenyl)-7-methoxy-5-(2-methoxy-benzyl)-1-(2-methoxy-ethyl)-1H-benzoimidazole
4-Bromo-5-ethyl-2-(4-isopropyl-phenyl)-7-methoxy-1-(2-methoxy-ethyl)-1H-benzoimidazole
4-Bromo-5-cyclobutylmethyl-2-(4-isopropyl-phenyl)-7-methoxy-1-(2-methoxy-ethyl)-1H-benzoimidazole
4-Bromo-5-(3-fluoro-benzyl)-2-(4-isopropyl-phenyl)-7-methoxy-1-(2-methoxy-ethyl)-1H-benzoimidazole
4-Bromo-5-(3-chloro-benzyl)-2-(4-isopropyl-phenyl)-7-methoxy-1-(2-methoxy-ethyl)-1H-benzoimidazole
4-Bromo-2-(4-isopropyl-phenyl)-7-methoxy-1-(2-methoxy-ethyl)-5-thiazol-2-ylmethyl-1H-benzoimidazole
4-Bromo-5-(3,5-difluoro-benzyl)-2-(4-isopropyl-phenyl)-7-methoxy-1-(2-methoxy-ethyl)-1H-benzoimidazole
4-Bromo-2-(4-isopropyl-phenyl)-7-methoxy-1-(2-methoxy-ethyl)-5-pyridin-3-ylmethyl-1H-benzoimidazole
4-Bromo-2-(4-isopropyl-phenyl)-7-methoxy-1-(2-methoxy-ethyl)-5-(2-methylsulfanyl-benzyl)-1H-benzoimidazole
4-Bromo-2-(4-isopropyl-phenyl)-5-(2-methanesulfinyl-benzyl)-7-methoxy-1-(2-methoxy-ethyl)-1H-benzoimidazole
4-Bromo-2-(4-isopropyl-phenyl)-5-(2-methanesulfonyl-benzyl)-7-methoxy-1-(2-methoxy-ethyl)-1H-benzoimidazole
4-Bromo-2-(4-isopropyl-phenyl)-7-methoxy-1-(2-methoxy-ethyl)-5-pyridin-2-ylmethyl-1H-benzoimidazole
4-Iodo-2-(4-isopropyl-phenyl)-7-methoxy-5-(2-methoxy-benzyl)-1-(2-methoxy-ethyl)-1H-benzoimidazole
4-Bromo-2-(4-isopropyl-phenyl)-7-methoxy-5-(2-methoxy-benzyl)-1-(2-methoxy-ethyl)-1H-benzoimidazole
4-Bromo-5-(3,4-dimethoxy-benzyl)-2-(4-isopropyl-phenyl)-7-methoxy-1-(2-methoxy-ethyl)-1H-benzoimidazole
4-Bromo-2-(4-isopropyl-phenyl)-7-methoxy-1-(2-methoxy-ethyl)-5-(3-methoxy-pyridin-2-ylmethyl)-1H-benzoimidazole
5-Benzyl-4-ethyl-2-(4-isopropyl-phenyl)-7-methoxy-1-(2-methoxy-ethyl)-1H-benzoimidazole
4-Bromo-2-(4-isopropyl-phenyl)-7-methoxy-5-(3-methoxy-benzyl)-1-(2-methoxy-ethyl)-1H-benzoimidazole
[4-Bromo-2-(4-isopropyl-phenyl)-7-methoxy-1-(2-methoxy-ethyl)-1H-benzoimidazol-5-yl]-(3-methoxy-phenyl)-methanone
[4-Bromo-2-(4-isopropyl-phenyl)-7-methoxy-1-(2-methoxy-ethyl)-1H-benzoimidazol-5-yl]-(2-methoxy-phenyl)-methanone
4-Bromo-2-(4-isopropyl-phenyl)-7-methoxy-1-(2-methoxy-ethyl)-5-(1-phenyl-ethyl)-1H-benzoimidazole
4-Iodo-2-(4-isopropyl-phenyl)-7-methoxy-1-(2-methoxy-ethyl)-1H-benzoimidazole-5-carbonitrile
2-(4-isopropyl-phenyl)-7-methoxy-1-(2-methoxy-ethyl)-1H-benzoimidazole-4-carbonitrile
4-Isobutyl-2-(4-isopropyl-phenyl)-7-methoxy-1-(2-methoxy-ethyl)-1H-benzoimidazole
4-Benzyl-2-(4-isopropyl-phenyl)-7-methoxy-1-(2-methoxy-ethyl)-1H-benzoimidazole
4,7-Dibromo-2-(4-isopropyl-phenyl)-1-(2-methoxy-ethyl)-1H-benzoimidazole
4,7-Dibromo-2-(4-isopropyl-phenyl)-1-(2-ethoxy-ethyl)-1H-benzoimidazole
4-Bromo-2-(4-isopropyl-phenyl)-7-methoxy-1-(2-methoxy-ethyl)-5-phenyl-1H-benzoimidazole
4-Bromo-5-(3,4-dimethoxy-phenyl)-2-(4-isopropyl-phenyl)-7-methoxy-1-(2-methoxy-ethyl)-1H-benzoimidazole
3-[4-Bromo-2-(4-isopropyl-phenyl)-7-methoxy-1-(2-methoxy-ethyl)-1H-benzoimidazol-5-yl]-phenol
4-Bromo-2-(4-isopropyl-phenyl)-7-methoxy-1-(2-methoxy-ethyl)-5-(3-methoxy-phenyl)-1H-benzoimidazole
3-[4-Bromo-2-(4-isopropyl-phenyl)-7-methoxy-1-(2-methoxy-ethyl)-1H-benzoimidazol-5-yl]-benzoic acid ethyl ester
4-[4-Bromo-2-(4-isopropyl-phenyl)-7-methoxy-1-(2-methoxy-ethyl)-1H-benzoimidazol-5-yl]-benzoic acid ethyl ester
4-Bromo-2-(4-isopropyl-phenyl)-7-methoxy-1-(2-methoxy-ethyl)-5-pyridin-3-yl-1H-benzoimidazole
3-[4-Bromo-2-(4-isopropyl-phenyl)-7-methoxy-1-(2-methoxy-ethyl)-1H-benzoimidazol-5-yl]-benzonitrile
1-{5-[4-Bromo-2-(4-isopropyl-phenyl)-7-methoxy-1-(2-methoxy-ethyl)-1H-benzoimidazol-5-yl]-2-methoxy-phenyl}-ethanone
2-[4-Bromo-2-(4-isopropyl-phenyl)-7-methoxy-1-(2-methoxy-ethyl)-1H-benzoimidazol-5-yl]-benzonitrile
4-Iodo-2-(4-isopropyl-phenyl)-7-methoxy-1-(2-methoxy-ethyl)-5-pyridin-4-yl-1H-benzoimidazole
4-Bromo-2-(4-isopropyl-phenyl)-7-methoxy-1-(2-methoxy-ethyl)-5-(4-methyl-pyrazol-1-ylmethyl)-1H-benzoimidazol
4-Bromo-5-imidazol-1-ylmethyl-2-(4-isopropyl-phenyl)-7-methoxy-1-(2-methoxy-ethyl)-1H-benzoimidazole
4-Bromo-5-(4-bromo-5-methyl-pyrazol-1-ylmethyl)-2-(4-isopropyl-phenyl)-7-methoxy-1-(2-methoxy-ethyl)-1H-benzoimidazole
4-Bromo-5-(4-bromo-3-methyl-pyrazol-1-ylmethyl)-2-(4-isopropyl-phenyl)-7-methoxy-1-(2-methoxy-ethyl)-1H-benzoimidazole
4-Bromo-5-(3,5-dimethyl-pyrazol-1-ylmethyl)-2-(4-isopropyl-phenyl)-7-methoxy-1-(2-methoxy-ethyl)-1H-benzoimidazole
1[4-Bromo-1-(2-hydroxy-ethyl)-2-(4-isopropyl-phenyl)-7-methoxy-1H-benzoi midazol-5-ylmethyl]-1H-imidazole-2-carboxylic acid ethyl ester 4-Bromo-2-(4-isopropyl-phenyl)-7-methoxy-1-(2-methoxy-ethyl)-5-(2-methoxymethyl-imidazol-1-ylmethyl)-1H-benzoimidazole 4-Bromo-2-(4-isopropyl-phenyl)-7-methoxy-1-(2-methoxy-ethyl)-5-(2-methylsulfanyl-imidazol-1-ylmethyl)-1H-benzoimidazole 1-[4-Bromo-2-(4-isopropyl-phenyl)-7-methoxy-1-(2-methoxy-ethyl)-1H-benzoimidazol-5-ylmethyl]-1H-benzoimidazol-2-ol 4-Bromo-2-(4-isopropyl-phenyl)-7-methoxy-1-(2-methoxy-ethyl)-5-(2-methylsulfanyl-benzoimidazol-1-ylmethyl)-1H-benzoimidazole 4-Bromo-2-(4-isopropyl-phenyl)-5-(2-methanesulfinyl-benzoimidazol-1-ylmethyl)-7-methoxy-1-(2-methoxy-ethyl)-1H-benzoimidazole 4-Bromo-2-(4-isopropyl-phenyl)-7-methoxy-5-(2-methoxy-benzoimidazol-1-ylmethyl)-1-(2-methoxy-ethyl)-1H-benzoimidazole 3-[4-Bromo-1-(2-hydroxy-ethyl)-2-(4-isopropyl-phenyl)-7-methoxy-1H-benzoimidazol-5-ylmethyl]-3H-imidazole-4-carboxylic acid methyl ester 2-[4-Bromo-5-imidazo[4,5-b]pyridin-3-ylmethyl-2-(4-isopropyl-phenyl)-7-methoxy-benzoimidazol-1-yl]-ethanol 2-[4-Bromo-5-indazol-1-ylmethyl-2-(4-isopropyl-phenyl)-7-methoxy-benzoimidazol-1-yl]-ethanol 2-[4-Bromo-2-(4-isopropyl-phenyl)-7-methoxy-5-(5-methyl-tetrazol-2-ylmethyl)-benzoimidazol-1-yl]-ethanol 4-Bromo-5-(4-bromo-5-methyl-pyrazol-1-ylmethyl)-2-(4-cyclopropyl-phenyl)-7-methoxy-1-(2-methoxy-ethyl)-1H-benzoimidazole 4-Bromo-2-(4-isopropyl-phenyl)-7-methoxy-5-(4-methyl-pyrazol-1-ylmethyl)-1-(2-methylsulfanyl-ethyl)-1H-benzoimidazole 4-Bromo-5-isopropoxymethyl-2-(4-isopropyl-phenyl)-7-methoxy-1-(2-methoxy-ethyl)-1H-benzoimidazole 1-[4-Bromo-2-(4-isopropyl-phenyl)-7-methoxy-1-(2-methoxy-ethyl)-1H-benzoimidazol-5-ylmethyl]-pyrrolidin-2-one 4-Bromo-2-(4-isopropyl-phenyl)-7-methoxy-1-(2-methoxy-ethyl)-5-phenylsulfanyl-1H-benzoimidazole 5-Benzenesulfinyl-4-bromo-2-(4-isopropyl-phenyl)-7-methoxy-1-(2-methoxy-ethyl)-1H-benzoimidazole 5-Benzyl-2-(4-isopropyl-phenyl)-7-methoxy-1-(2-methoxy-ethyl)-4-trifluoromethyl-1H-benzoimidazole 2-(4-Isopropyl-phenyl)-7-methoxy-5-(2-methoxy-benzyl)-1-(2-methoxy-ethyl)-4-trifluoromethyl-1H-benzoimidazole 2-(4-Isopropyl-phenyl)-7-methoxy-1-(2-methoxy-ethyl)-5-pyridin-2-ylmethyl-4-trifluoromethyl-1H-benzoimidazole 2-(4-Isopropyl-phenyl)-7-methoxy-1-(2-methoxy-ethyl)-5-pyrazol-1-ylmethyl-4-trifluoromethyl-1H-benzoimidazole 4-Bromo-2-(4-isopropyl-phenyl)-7-methoxy-1-(2-methoxy-ethyl)-5-phenoxy methyl-1H-benzoimidazole 2-{2-[4-Bromo-2-(4-isopropyl-phenyl)-7-methoxy-1-(2-methoxy-ethyl)-1H-benzoimidazol-5-ylmethoxy]-phenyl}-ethanol 2-{2-[4-Bromo-2-(4-isopropyl-phenyl)-7-methoxy-1-(2-methoxy-ethyl)-1H-benzoimidazol-5-ylmethoxy]-phenoxy}-ethanol {2-[4-Bromo-2-(4-isopropyl-phenyl)-7-methoxy-1-(2-methoxy-ethyl)-1H-benzoimidazol-5-ylmethoxy]-phenyl}-methanol N-{2-[4-Bromo-2-(4-isopropyl-phenyl)-7-methoxy-1-(2-methoxy-ethyl)-1H-benzoimidazol-5-ylmethoxy]-phenyl}-acetamide 2-[4-Bromo-2-(4-isopropyl-phenyl)-7-methoxy-1-(2-methoxy-ethyl)-1H-benzoimidazol-5-ylmethoxy]-benzamide 2-[4-Bromo-2-(4-isopropyl-phenyl)-7-methoxy-1-(2-methoxy-ethyl)-1H-benzoimidazol-5-ylmethoxy]-benzenesulfonamide 2-[4-Bromo-2-(4-isopropyl-phenyl)-7-methoxy-1-(2-methoxy-ethyl)-1H-benzoimidazol-5-ylmethoxy]-phenylamine 1-{2-[4-Bromo-2-(4-isopropyl-phenyl)-7-methoxy-1-(2-methoxy-ethyl)-1H-benzoimidazol-5-ylmethoxy]-phenyl}-ethanone 2-[4-Bromo-2-(4-isopropyl-phenyl)-7-methoxy-1-(2-methoxy-ethyl)-1H-benzoimidazol-5-ylmethoxy]-phenol 2-[4-Bromo-2-(4-isopropyl-phenyl)-7-methoxy-1-(2-methoxy-ethyl)-1H-ben zoimidazol-5-ylmethoxy]-pyridin-3-ol 4-Bromo-2-(4-isopropyl-phenyl)-7-methoxy-1-(2-methoxy-ethyl)-5-(pyridin-2-yloxymethyl)-1H-benzoimidazole 4-Bromo-2-(4-isopropyl-phenyl)-7-methoxy-1-(2-methoxy-ethyl)-5-(2-methoxy-phenoxymethyl)-1H-benzoimidazole {3-[4-Bromo-2-(4-isopropyl-phenyl)-7-methoxy-1-(2-methoxy-ethyl)-1H-benzoimidazol-5-ylmethoxy]-2-methyl-phenyl}-methanol 4-Bromo-2-(4-isopropyl-phenyl)-7-methoxy-1-(2-methoxy-ethyl)-5-(pyridin-3-yloxymethyl)-1H-benzoimidazole 4-Bromo-2-(4-isopropyl-phenyl)-5-(2-methanesulfonyl-phenoxymethyl)-7-methoxy-1-(2-methoxy-ethyl)-1H-benzoimidazole 2-{3-[4-Bromo-2-(4-isopropyl-phenyl)-7-methoxy-1-(2-methoxy-ethyl)-1H-benzoimidazol-5-ylmethoxy]-phenoxy}-ethanol 2-{2-[4-Bromo-2-(4-isopropyl-phenyl)-7-methoxy-1-(2-methoxy-ethyl)-1H-benzoimidazol-5-ylmethoxy]-phenyl}-acetamide 2-{2-[2-(4-Isopropyl-phenyl)-7-methoxy-1-(2-methoxy-ethyl)-4-trifluoromethyl-1H-benzoimidazol-5-ylmethoxy]-phenoxyl}-ethanol 2-{2-[2-(4-Isopropyl-phenyl)-7-methoxy-1-(2-methoxy-ethyl)-4-trifluoromethyl-1H-benzoimidazol-5-ylmethoxy]-phenyl}-ethanol

[4-Bromo-2-(4-isopropyl-phenyl)-7-methoxy-1-(2-methoxy-ethyl)-1H-benzoimidazol-5-ylmethyl]-phenyl-amine

[4-Bromo-2-(4-isopropyl-phenyl)-7-methoxy-1-(2-methoxy-ethyl)-1H-benzoimidazol-5-ylmethyl]-(2-methanesulfonyl-phenyl)-amine

[4-Bromo-2-(4-isopropyl-phenyl)-7-methoxy-1-(2-methoxy-ethyl)-1H-benzoimidazol-5-ylmethyl]-[2-(2-methanesulfonyl-ethyl)-phenyl]-amine 2-(2-{[4-Bromo-2-(4-isopropyl-phenyl)-7-methoxy-1-(2-methoxy-ethyl)-1H-benzoimidazol-5-ylmethyl]-aminol}phenyly)-acetamide 2-{[4-Bromo-2-(4-isopropyl-phenyl)-7-methoxy-1-(2-methoxy-ethyl)-1H-benzoimidazol-5-ylmethyl]-amino}-benzenesulfonic acid

[4-Bromo-2-(4-isopropyl-phenyl)-7-methoxy-1-(2-methoxy-ethyl)-1H-benzoimidazol-5-ylmethyl]-(2-fluoro-phenyl)-amine

[4-Bromo-2-(4-isopropyl-phenyl)-7-methoxy-1-(2-methoxy-ethyl)-1H-benzoimidazol-5-ylmethyl]-pyridin-2-yl-amine 2-{[4-Bromo-2-(4-isopropyl-phenyl)-7-methoxy-1-(2-methoxy-ethyl)-1H-benzoimidazol-5-ylmethyl]-amino}benzoic acid methyl ester

[4-Bromo-2-(4-isopropyl-phenyl)-7-methoxy-1-(2-methoxy-ethyl)-1H-benzoimidazol-5-ylmethyl]-pyridin-3-yl-amine

[4-Bromo-2-(4-isopropyl-phenyl)-7-methoxy-1-(2-methoxy-ethyl)-1H-benzoimidazol-5-ylmethyl]-methyl-phenyl-amine

[4-Bromo-2-(4-isopropyl-phenyl)-7-methoxy-1-(2-methoxy-ethyl)-1H-benzoimidazol-5-ylmethyl]-(3-methanesulfonyl-phenyl)amine 2-(2-{[2-(4-Isopropyl-phenyl)-7-methoxy-1-(2-methoxy-ethyl)-4-trifluoromethyl-1H-benzoimidazol-5-ylmethyl]-aminol}-phenyly)-acetamide

[2-(4-Isopropyl-phenyl)-7-methoxy-1-(2-methoxy-ethyl)-4-trifluoromethyl-1H-benzoimidazol-5-ylmethyl]-(2-methanesulfonyl-phenyl)-amine

[2-(4-Isopropyl-phenyl)-7-methoxy-1-(2-methoxy-ethyl)-4-trifluoromethyl-1H-benzoimidazol-5-ylmethyl]-[2-(2-methanesulfonyl-ethyl)-phenyl]-amine 1-[4-Bromo-2-(4-isopropyl-phenyl)-7-methoxy-1-(2-methoxy-ethyl)-1H-benzoimidazol-5-ylmethyl]-1H-imidazole-2-carboxylic acid methyl ester 1-[4-Bromo-2-(4-isopropyl-phenyl)-7-methoxy-1-(2-methoxy-ethyl)-1H-benzoimidazol-5-ylmethyl]-1H-imidazole-2-carboxylic acid dimethylamide 1-{1-[4-Bromo-2-(4-isopropyl-phenyl)-7-methoxy-1-(2-methoxy-ethyl)-1H-benzoimidazol-5-ylmethyl]-1H-imidazol-2-yl}-ethanone 1-[4-Bromo-2-(4-isopropyl-phenyl)-7-methoxy-1-(2-methoxy-ethyl)-1H-benzoimidazol-5-ylmethyl]-1H-indole-2,3-dione 4-Bromo-2-(4-isopropyl-phenyl)-7-methoxy-1-(2-methoxy-ethyl)-5-oxazol-2-ylmethyl-1H-benzoimidazole 1-[4-Bromo-2-(4-isopropyl-phenyl)-7-methoxy-1-(2-methoxy-ethyl)-1H-benzoimidazol-5-ylmethyl]-1H-imidazole-2-carbonitrile 1-[4-Bromo-2-(4-isopropyl-phenyl)-7-methoxy-1-(2-methoxy-ethyl)-1H-benzoimidazol-5-ylmethyl]-1H-imidazole-2-carboxylic acid methylamide 2-(4-Isopropyl-phenyl)-7-methoxy-1-(2-methoxy-ethyl)-5-bromo-4-trifluoromethyl-1H-benzoimidazole

[2-(4-Isopropyl-phenyl)-7-methoxy-1-(2-methoxy-ethyl)-4-trifluoromethyl-1H-benzoimidazol-5-ylmethyl]-phenyl-amine

[2-(4-Isopropyl-phenyl)-7-methoxy-1-(2-methoxy-ethyl)-4-trifluoromethyl-1H-benzoimidazol-5-ylmethyl]-pyridin-2-yl-amine 2-{[2-(4-Isopropyl-phenyl)-7-methoxy-1-(2-methoxy-ethyl)-4-trifluoromethyl-1H-benzoimidazol-5-ylmethyl]-aminol}-benzenesulfonamide 2-(4-Isopropyl-phenyl)-7-methoxy-1-(2-methoxy-ethyl)-5-phenoxymethyl-4-trifluoromethyl-1H-benzoimidazole 2-(4-Isopropyl-phenyl)-7-methoxy-1-(2-methoxy-ethyl)-5-(pyridin-2-yloxymethyl)-4-trifluoromethyl-1H-benzoimidazole 2-[2-(4-Isopropyl-phenyl)-7-methoxy-1-(2-methoxy-ethyl)-4-trifluoromethyl-1H-benzoimidazol-5-yl-methoxy]-benzenesulfonamide 4-Bromo-2-(4-isopropyl-phenyl)-7-methoxy-1-(2-methoxy-ethyl)-5-(pyridin-2-yloxy)-1H-benzoimidazole.

3. A pharmaceutical composition comprising a compound of formula (I) as defined in claim 1 in association with a pharmaceutically acceptable excipient, diluent or carrier.

4. A pharmaceutical composition according to claim 3 containing 0.03 to 300 mg of the compound of formula (I).

* * * * *